United States Patent
Muzzey et al.

(10) Patent No.: US 12,020,779 B1
(45) Date of Patent: Jun. 25, 2024

(54) NONINVASIVE PRENATAL SCREENING USING DYNAMIC ITERATIVE DEPTH OPTIMIZATION WITH DEPTH-SCALED VARIANCE DETERMINATION

(71) Applicant: MYRIAD WOMEN'S HEALTH, INC., South San Francisco, CA (US)

(72) Inventors: Dale E. Muzzey, San Francisco, CA (US); Kevin R. Haas, Berkeley, CA (US); Jeffrey R. Tratner, San Francisco, CA (US); Kevin M. D'Auria, San Francisco, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 1240 days.

(21) Appl. No.: 16/124,033

(22) Filed: Sep. 6, 2018

Related U.S. Application Data

(60) Provisional application No. 62/572,962, filed on Oct. 16, 2017, provisional application No. 62/554,758, filed on Sep. 6, 2017.

(51) Int. Cl.
*G16B 20/20* (2019.01)
*C12Q 1/6827* (2018.01)
*G16B 20/10* (2019.01)

(52) U.S. Cl.
CPC .......... *G16B 20/20* (2019.02); *C12Q 1/6827* (2013.01); *G16B 20/10* (2019.02)

(58) Field of Classification Search
CPC ....... G16B 20/20; G16B 20/10; C12Q 1/6827
See application file for complete search history.

(56) References Cited

U.S. PATENT DOCUMENTS

| | | | |
|---|---|---|---|
| 8,008,018 B2 | 8/2011 | Quake | |
| 8,700,338 B2 | 4/2014 | Oliphant | |
| 2010/0112575 A1 | 5/2010 | Fan | |
| 2014/0162269 A1 | 6/2014 | Rabinowitz | |

FOREIGN PATENT DOCUMENTS

| | | | |
|---|---|---|---|
| WO | WO-2015184404 A1 * | 12/2015 | ........... C12Q 1/6858 |

OTHER PUBLICATIONS

Bayindir, B., et al., Noninvasive prenatal testing using a novel analysis pipeline to screen for all autosomal fetal aneuploidies improves pregnancy management. European Journal of Human Genetics, 23(10), pp. 1286-1293. (Year: 2015).*
Carreiro, A.V., Anunciação, O., Carriço, J.A. and Madeira, S.C., 2011. Prognostic prediction through biclustering-based classification of clinical gene expression time series. Journal of integrative bioinformatics, 8(3), pp. 73-89. (Year: 2011).*
Yin, A.H., el al., 2015. Noninvasive detection of fetal subchromosomal abnormalities by semiconductor sequencing of maternal plasma DNA. Proceedings of the National Academy of Sciences, 112(47), pp. 14670-14675. (Year: 2015).*
Kim, S.K., Hannum, G., Geis, J., Tynan, J., Hogg, G., Zhao, C., Jensen, T.J., Mazloom, A.R., Oeth, P., Ehrich, M. and van den Boom, D., 2015. Determination of fetal DNA fraction from the plasma of pregnant women using sequence read counts. Prenatal diagnosis, 35(8), pp. 810-815. Supp. Information (Year: 2015).*
Chandrananda D, Thorne NP, Ganesamoorthy D, Bruno DL, Benjamini Y, et al. (2014) Investigating and Correcting Plasma DNA Sequencing Coverage Bias to Enhance Aneuploidy Discovery. PLoS ONE 9(1): e86993. doi:10.1371/journal.pone.0086993, p. 1-14.
Fan HC, Quake SR (2010) Sensitivity of Noninvasive Prenatal Detection of Fetal Aneuploidy from Maternal Plasma Using Shotgun Sequencing Is Limited Only by Counting Statistics. PLoS ONE 5(5): e10439. doi:10.1371/journal.pone.0010439, p. 1-7.
Johansen et al., Open source non-invasive prenatal testing platform and its performance in a public health laboratory, Prenat Diagn. Jun. 2016;36(6):530-6. doi: 10.1002/pd.4819. Epub Apr. 24, 2016, p. 1-24.
Kim et al., Determination of fetal DNA fraction from the plasma of pregnant women using sequence read counts, Prenatal Diagnosis 2015, 35, 810-815.
Meyer et al., Targeted high-throughput sequencing of tagged nucleic acid samples, Nucleic Acids Research, 2007, vol. 35, No. 15 e97, doi:10.1093/nar/gkm566, p. 1-5.
Ryan et al., Validation of an Enhanced Version of a Single-Nucleotide Polymorphism-Based Noninvasive Prenatal Test for Detection of Fetal Aneuploidies, Fetal Diagn Ther 2016;40:219-223, DOI: 10.1159/000442931.
Sparks AB, Struble CA, Wang ET, et al. Noninvasive prenatal detection and selective analysis of cell-free DNA obtained from maternal blood: evaluation for trisomy 21 and trisomy 18. Am J Obstet Gynecol 2012;206:319.e1-9.

(Continued)

*Primary Examiner* — Olivia M. Wise
*Assistant Examiner* — Janna Nicole Schultzhaus
(74) *Attorney, Agent, or Firm* — Foley & Lardner LLP

(57) ABSTRACT

Fetal maternal samples taken from pregnant women include both maternal cell-free DNA and fetal cell-free DNA. Described herein are methods for determining a chromosomal abnormality of a test chromosome in a fetus by analyzing a test maternal sample of a woman carrying said fetus, wherein the test maternal sample comprises fetal cell-free DNA and maternal cell-free DNA. The chromosomal abnormality can be, for example, aneuploidy or the presence of a microdeletion. In some embodiments, the chromosomal abnormality is determined by measuring a dosage of the test chromosome, determining a depth-scaled variation value correlated to an initial number of sequencing reads obtained from an assay of the test maternal sample, and determining an initial value of statistical significance for the test chromosome based on the measured dosage of the test chromosome, an expected dosage of the test chromosome, and the depth-scaled variation value.

15 Claims, 22 Drawing Sheets

(56) References Cited

OTHER PUBLICATIONS

Straver et al., Calculating the fetal fraction for noninvasive prenatal testing based on genome-wide nucleosome profiles, Prenatal Diagnosis 2016, 36, 614-621.
Xu X-P, Gan H-Y, Li F-X, Tian Q, Zhang J, Liang R-L, et al. (2016) A Method to Quantify Cell-Free Fetal DNA Fraction in Maternal Plasma Using Next Generation Sequencing: Its Application in Non-Invasive Prenatal Chromosomal Aneuploidy Detection. PLoS ONE 11(1): e0146997. doi:10.1371/journal.pone.0146997, p. 1-13.
Chim et al., Detection of the placental epigenetic signature of the maspin gene in maternal plasma, PNAS USA, 102:14753-58 (2005).
Zhao et al., Detection of Fetal Subchromosomal Abnormalities by Sequencing Circulating Cell-Free DNA from Maternal Plasma, Clinical Chemistry, vol. 61, pp. 608-616 (2015).

* cited by examiner

NONINVASIVE PRENATAL SCREENING USING DYNAMIC ITERATIVE DEPTH OPTIMIZATION WITH DEPTH-SCALED VARIANCE DETERMINATION

CROSS-REFERENCE TO RELATED APPLICATIONS

This application claims the benefit of U.S. Provisional Application No. 62/554,758, filed Sep. 6, 2017 and titled NONINVASIVE PRENATAL SCREENING USING DYNAMIC ITERATIVE DEPTH OPTIMIZATION WITH DEPTH-SCALED VARIANCE DETERMINATION and of U.S. Provisional Application No. 62/572,962, filed Oct. 16, 2017 and titled NONINVASIVE PRENATAL SCREENING USING DYNAMIC ITERATIVE DEPTH OPTIMIZATION WITH DEPTH-SCALED VARIANCE DETERMINATION, the disclosure of each of which is incorporated by reference herein in its entirety.

FIELD OF THE INVENTION

The present invention relates to the determination of fetal abnormalities by measuring dosages of one or more chromosomes or portions thereof from cell-free DNA.

BACKGROUND

Circulating throughout the bloodstream of a pregnant woman and separate from cellular tissue are small pieces of DNA, often referred to as cell-free DNA (cfDNA). The cfDNA in the maternal bloodstream includes cfDNA from both the mother (i.e., maternal cfDNA) and the fetus (i.e., fetal cfDNA). The fetal cfDNA originates from the placental cells undergoing apoptosis, and constitutes up to 25% of the total circulating cfDNA, with the balance originating from the maternal genome.

Recent technological developments have allowed for noninvasive prenatal screening of chromosomal aneuploidy in the fetus by exploiting the presence of fetal cfDNA circulating in the maternal bloodstream. Noninvasive methods relying on cfDNA sampled from the pregnant woman's blood serum are particularly advantageous over chorionic villi sampling or amniocentesis, both of which risk substantial injury and possible pregnancy loss.

Accurate determination of the fraction of fetal cfDNA taken from a maternal test sample allows for improved screening of fetal aneuploidy. The fetal fraction for male pregnancies (i.e., a male fetus) can be determined by comparing the amount of Y chromosome from the cfDNA, which can be presumed to originate from the fetus, to the amount of one or more genomic regions that are present in both maternal and fetal cfDNA. Determination of the fetal fraction for female pregnancies (i.e., a female fetus) is more complex, as both the fetus and the pregnant mother have similar sex-chromosome dosage and there are few features to distinguish between maternal and fetal DNA. Methylation differences between the fetal and maternal DNA can be used to estimate the fetal fraction of cfDNA, but such methods are often cumbersome. See, for example, Chim et al., PNAS USA, 102:14753-58 (2005). In another method, the fraction of fetal cfDNA can be determined by sequencing polymorphic loci to search for allelic differences between the maternal and fetal cfDNA. See, for example, U.S. Pat. No. 8,700,338. However, as explained in U.S. Pat. No. 8,700,338 (col. 18, lines 28-36), use of polymorphic loci to determine fetal fraction becomes unreliable when the fetal fraction drops below 3%. See also Ryan et al., Fetal Diag. & Ther., vol. 40, pp. 219-223 (Mar. 31, 2016), which describes setting a threshold for "no call" when the fetal fraction is below 2.8%.

The disclosures of all publications referred to herein are each hereby incorporated herein by reference in their entireties. To the extent that any reference incorporated by references conflicts with the instant disclosure, the instant disclosure shall control.

SUMMARY OF THE INVENTION

In one aspect, there is provided a method for determining a chromosomal abnormality in a test chromosome of a fetus by analyzing a test maternal sample of a woman carrying said fetus, wherein the test maternal sample includes fetal cell-free DNA and maternal cell-free DNA. The method may include obtaining an initial number of sequencing reads from the test maternal sample using an initial depth assay; aligning the sequencing reads from an interrogated region of the test maternal sample; binning the aligned sequencing reads from the interrogated region of the test maternal sample in a plurality of bins; counting the number of sequencing reads in each of the plurality of the bins; measuring a dosage of the test chromosome or a portion thereof in the test maternal sample based on the number of sequencing reads in a set of bins corresponding to the test chromosome or the portion thereof; determining a depth-scaled variation value correlated to the initial number of sequencing reads obtained from the test maternal sample; and determining an initial value of statistical significance for the test chromosome or the portion thereof in the test maternal sample based on the measured dosage of the test chromosome or the portion thereof, an expected dosage of the test chromosome or the portion thereof, and the depth-scaled variation value.

In some embodiments, determining the depth-scaled variation value may include calculating the depth-scaled variation value based on a plurality of reference samples assayed at a sequencing depth or range of sequencing depths corresponding to the initial number of sequencing reads obtained from the test maternal sample. In some embodiments, the depth-scaled variation value may be determined based on variation in counts of binned sequencing reads for the test chromosome or the portion thereof of the plurality of reference maternal samples.

In some embodiments, the method may include calling the test chromosome or the portion thereof in the fetal cell-free DNA of the test maternal sample to be abnormal if the absolute value of the initial value of statistical significance is above a predetermined threshold. In some embodiments, the method may include re-measuring the dosage of the test chromosome or the portion thereof in the test maternal sample using a higher depth assay if the absolute value of the scaled value of statistical significance is below a predetermined threshold, and determining a subsequent value of statistical significance for the test chromosome or the portion thereof in the test maternal sample based on the re-measured dosage.

In some embodiments, the method may include measuring a fetal fraction of cell-free DNA in the test maternal sample based on counts of binned sequencing reads from the interrogated region of the test maternal sample, and determining an initial value of likelihood that the test chromosome or the portion thereof in the fetal cell-free DNA of the test maternal sample is abnormal based on the initial value of statistical significance and the measured fetal fraction. In some embodiments, the value of likelihood may be an odds ratio. In some embodiments, the method may include calling the test chromosome or the portion thereof in the fetal cell-free DNA of the test maternal sample to be normal if the scaled value of likelihood is below a predetermined threshold. In some embodiments, the method may include re-measuring the dosage of the test chromosome or the portion thereof in the test maternal sample using a higher depth assay if the scaled value of likelihood is above a predetermined threshold and the absolute value of the scaled value of statistical significance is below a predetermined threshold, and determining a subsequent value of statistical significance for the test chromosome or the portion thereof in the test maternal sample based on the re-measured dosage.

In some embodiments, the depth-scaled variation value may be a standard deviation, an interquartile range, or a variance. In some embodiments, the value of statistical significance may be a Z-score, a p-value, or a probability. In some embodiments, the chromosomal abnormality may be a microdeletion, and the test chromosome or the portion thereof is a putative microdeletion. In some embodiments, the chromosomal abnormality may be aneuploidy, and the test chromosome or the portion thereof may be at least one complete chromosome. In some embodiments, the dosages of a plurality of test chromosomes or portions thereof may be simultaneously measured. In some embodiments, the dosage of the test chromosome or the portion thereof in the test maternal sample may be measured by determining an average number of sequencing reads per bin and a variation of the number of sequencing reads per bin.

In some embodiments, the method may include selecting a plurality of cohort reference maternal samples based on at least one similarity between each of the plurality of cohort reference maternal samples and the test maternal sample. In some embodiments, the at least one similarity between each of the plurality of cohort reference maternal samples and the test maternal sample may include at least one of a similarity in guanine-cytosine (GC) biases, binned sequencing depths, and normalized chromosomal medians between the set of reference maternal samples and the test maternal sample. In some embodiments, the at least one similarity between each of the plurality of cohort reference maternal samples and the test maternal sample may be determined by identifying one or more clusters that each include the test maternal sample and at least one of the plurality of cohort reference maternal samples. In some embodiments, the one or more clusters may be identified based on characteristic values of each of the plurality of cohort reference maternal samples and the test maternal sample. In some embodiments, the one or more clusters may be generated by k-means clustering of a plurality of reference maternal samples that includes the plurality of cohort reference maternal samples. In some embodiments, the at least one similarity between each of the plurality of cohort reference maternal samples and the test maternal sample may be determined by identifying one or more clusters based on at least one characteristic value of the each of each the plurality of cohort reference maternal samples, determining a centroid of each of the one or more clusters, and determining that the at least one characteristic value of the test maternal sample is within a threshold distance of the centroid of each of the one or more clusters. In some embodiments, the initial value of statistical significance for the test chromosome or the portion thereof may be determined by calculating an expected variation value that is based on the depth-scaled variation value and a cohort-based variation value that is determined based on variation in counts of binned sequencing reads for the test chromosome or the portion thereof of the plurality of cohort reference maternal samples.

In some embodiments, the method may include determining the expected dosage of the test chromosome or a portion thereof in the test maternal sample using a robust regression model that is trained based on measured dosages of a plurality of chromosomes or portions thereof of a plurality of reference maternal samples. In some embodiments, the trained regression model may be a maximum likelihood type regression model. In some embodiments, the trained regression model may be a Huber robust regression model. In some embodiments, the interrogated region may include at least a portion of a chromosome other than the test chromosome or the portion thereof. In some embodiments, the interrogated region may include at least a whole chromosome other than the test chromosome. In some embodiments, the robust regression model may be trained by, for each of the plurality of reference maternal samples: aligning sequencing reads from the interrogated region in the plurality of chromosomes or portions thereof, binning the aligned sequencing reads from the interrogated region in a plurality of bins, and counting the number of sequencing reads in each bin, and determining one or more model coefficients based on the number of sequencing reads in each bin for each of the plurality of reference maternal samples. In some embodiments, the trained regression model may utilize a weight function that varies based on at least one of an average number of sequencing reads per bin and a variation of the number of sequencing reads per bin for the plurality of bins. In some embodiments, the method may include normalizing the number of sequencing reads in each bin prior to counting the number of sequencing reads in each bin.

In some embodiments, the method may include determining a predicted value of statistical significance for the test chromosome or the portion of the test maternal sample thereof based on an additional depth-scaled variation value correlated to a higher number of sequencing reads that is higher than the initial number of sequencing reads obtained from the test maternal sample. In some embodiments, determining the additional depth-scaled variation value may include calculating the depth-scaled variation value based on a plurality of reference samples assayed at a higher sequencing depth or range of sequencing depths corresponding to the higher number of sequencing reads.

In another aspect, there is provided a method for determining a chromosomal abnormality in a test chromosome of a fetus by analyzing a test maternal sample of a woman carrying said fetus, wherein the test maternal sample includes fetal cell-free DNA and maternal cell-free DNA. The method may include obtaining an initial number of sequencing reads from the test maternal sample using an initial depth assay; aligning the sequencing reads from an interrogated region of the test maternal sample; binning the aligned sequencing reads from the interrogated region in a plurality of bins; counting the number of sequencing reads in each of the plurality of the bins; measuring a dosage of the test chromosome or a portion thereof in the test maternal sample based on the number of sequencing reads in a set of bins corresponding to the test chromosome or the portion thereof; identifying a plurality of reference maternal samples based on at least one similarity between binned sequencing reads of the plurality of reference maternal samples and the binned sequencing reads of the test maternal sample; determining an expected dosage of the test chromosome or a portion thereof in the test maternal sample based on a measured dosage of the test chromosome or portion thereof in each of the plurality of reference maternal samples; and determining an initial value of statistical significance for the test chromosome or the portion thereof in the test maternal sample based on the measured dosage and the expected dosage of the test chromosome or the portion thereof.

In some embodiments, the method may include measuring a fetal fraction of cell-free DNA in the test maternal sample based on counts of binned sequencing reads from the interrogated region of the test maternal sample and determining an initial value of likelihood that the test chromosome or the portion thereof in the fetal cell-free DNA of the test maternal sample is abnormal based on the initial value of statistical significance and the measured fetal fraction. In some embodiments, the at least one similarity between the binned sequencing reads of the plurality of reference maternal samples and the binned sequencing reads of the test maternal sample may include at least one of a similarity in GC biases, binned sequencing depths, and normalized chromosomal medians between the plurality of reference maternal samples and the test maternal sample determined based on the target sequencing reads. In some embodiments, the at least one similarity between the binned sequencing reads of the plurality of reference maternal samples and the binned sequencing reads of the test maternal sample may be determined by identifying one or more clusters that each include the test maternal sample and at least one of the plurality reference samples based on the binned sequencing reads of the plurality of reference maternal samples and the binned sequencing reads of the test maternal sample. In some embodiments, the one or more clusters may be determined based on characteristic values of the binned sequencing reads of each of the plurality of reference maternal samples and the binned sequencing reads of the test maternal sample. In some embodiments, the at least one similarity between the plurality of reference maternal samples and the test maternal sample may be determined by identifying one or more clusters based on at least one characteristic value of the binned sequencing reads of the plurality of reference maternal samples; determining a centroid of each of the one or more clusters; and determining that the at least one characteristic value of the binned sequencing reads of the test maternal sample is within a threshold distance of the centroid of each of the one or more clusters.

In an additional aspect, there is provided a method for determining a chromosomal abnormality of a test chromosome or a portion thereof in a fetus by analyzing a test maternal sample of a woman carrying said fetus, wherein the test maternal sample includes fetal cell-free DNA and maternal cell-free DNA. The method may include obtaining an initial number of sequencing reads from the test maternal sample using an initial depth assay; aligning the sequencing reads from an interrogated region of the test maternal sample; binning the aligned sequencing reads from the interrogated region in a plurality of bins; counting the number of sequencing reads in each of the plurality of the bins; measuring a dosage of the test chromosome or a portion thereof in the test maternal sample based on the number of sequencing reads in a set of bins corresponding to the test chromosome or the portion thereof; determining an expected dosage of the test chromosome or a portion thereof in the test maternal sample using a robust regression model that is trained based on measured dosages of a plurality of chromosomes or portions thereof of each of a plurality of reference maternal samples; and determining an initial value of statistical significance for the test chromosome or the portion thereof in the test maternal sample based on the measured dosage and the expected dosage of the test chromosome or the portion thereof.

In some embodiments, the trained regression model may be a maximum likelihood type regression model. In some embodiments, the trained regression model may be a Huber robust regression model. In some embodiments, the interrogated region may include at least a portion of a chromosome other than the test chromosome or the portion thereof. In some embodiments, the interrogated region may include at least a whole chromosome other than the test chromosome. In some embodiments, the robust regression model may be trained by, for each of the plurality of reference maternal samples, aligning sequencing reads from the interrogated region in the plurality of chromosomes or portions thereof, binning the aligned sequencing reads from the interrogated region in a plurality of bins, and counting the number of sequencing reads in each bin, and determining one or more model coefficients based on the number of sequencing reads in each bin for each of the plurality of reference maternal samples. In some embodiments, the trained regression model may utilize a weight function that varies based on at least one of an average number of sequencing reads per bin and a variation of the number of sequencing reads per bin for at least one of the plurality of interrogated regions. In some embodiments, the method may include normalizing the number of sequencing reads in each bin prior to counting the number of sequencing reads in each bin.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of example embodiments and are a part of the specification. Together with the following description, these drawings demonstrate and explain various principles of the instant disclosure.

Figure 1A:
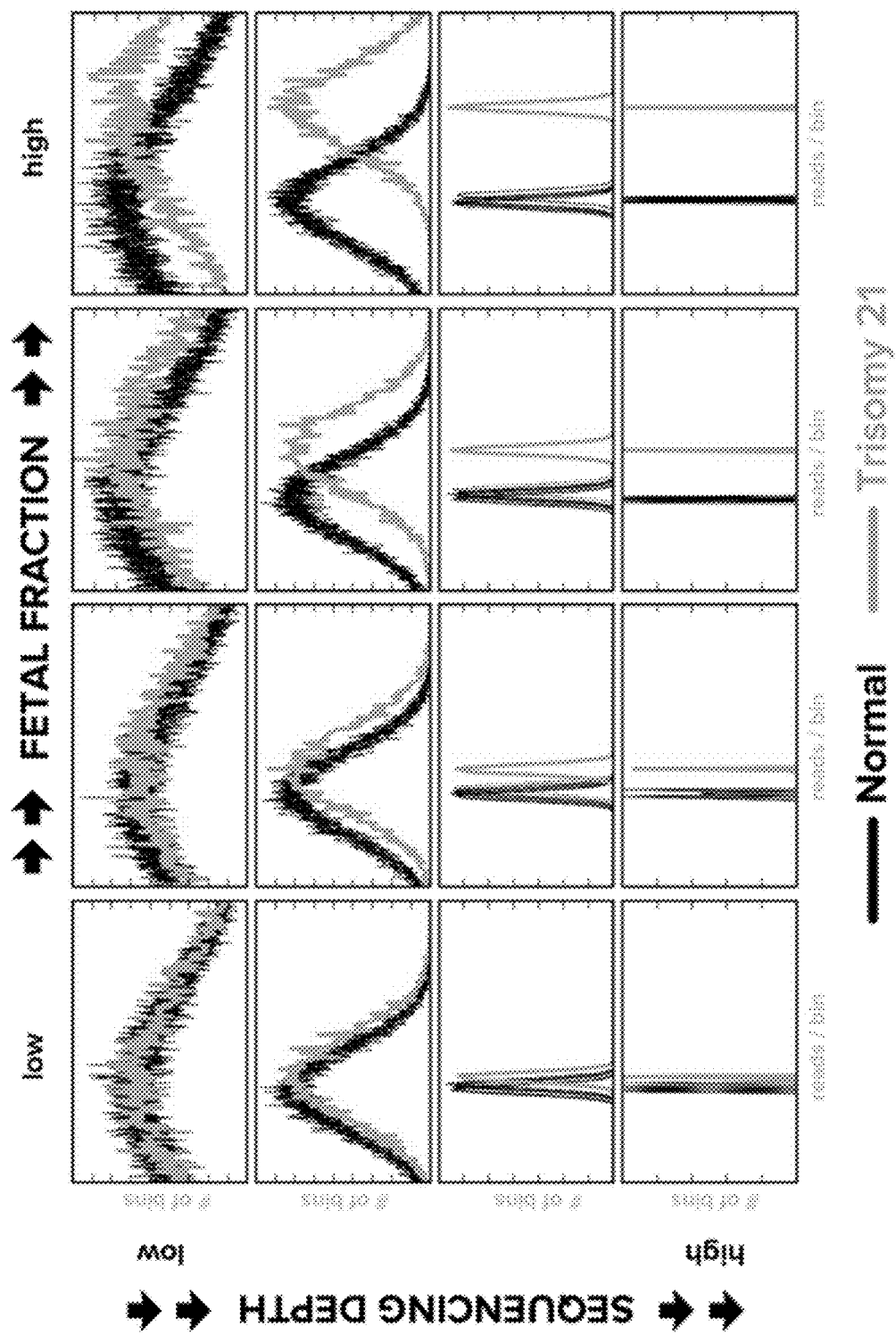
FIG. 1A illustrates the impact of fetal fraction and assay depth (specifically sequencing read depth) on resolving a triploid test chromosome (chromosome 21 in the illustrated example) dosage and an expected test chromosome dosage (which is expected to be diploid).

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION

Provided herein are methods for determining a fetal chromosomal abnormality (such as a microdeletion or chromosomal aneuploidy) in a test chromosome or a portion thereof by analyzing a test maternal sample, the methods including obtaining an initial number of sequencing reads from the test maternal sample using an initial depth assay; aligning the sequencing reads from an interrogated region of the test maternal sample; binning the aligned sequencing reads from the interrogated region of the test maternal sample in a plurality of bins; counting the number of sequencing reads in each of the plurality of the bins; measuring a dosage of the test chromosome or a portion thereof in the test maternal sample based on the number of sequencing reads in a set of bins corresponding to the test chromosome or the portion thereof; determining a depth-scaled variation value correlated to the initial number of sequencing reads obtained from the test maternal sample; and determining an initial value of statistical significance (such as a Z-score) for the test chromosome or the portion thereof in the test maternal sample based on the measured dosage of the test chromosome or the portion thereof, an expected dosage of the test chromosome or the portion thereof, and the depth-scaled variation value.

Noninvasive prenatal screens can be used to determine fetal aneuploidies for one or more test chromosomes using cell-free DNA from a test maternal blood sample. The results of screening can, for example, inform the patient's decision whether to pursue invasive diagnostic testing (such as amniocentesis or chronic villus sampling), which has a small (but non-zero) risk of miscarriage. Aneuploidy detection using noninvasive cfDNA analysis is linked to fetal fraction (that is, the proportion of cfDNA in the test maternal sample attributable to fetal origin). Aneuploidy can manifest in noninvasive prenatal screens that rely on a measured test chromosome dosage as a statistical increase or decrease in the count of quantifiable products (such as sequencing reads) that can be attributed to the test chromosome relative to an expected test chromosome dosage (that is, the count of quantifiable products that would be expected if the test chromosome were disomic). For samples with low fetal fraction, a large number of quantifiable products (e.g., a high read depth) are needed to achieve a statistically significant increase or decrease. Conversely, for samples with high fetal fraction, a smaller number of quantifiable products (e.g., a low read depth) can provide the statistically significant increase or decrease. The methods described herein can also be used to detect microdeletions in a fetal chromosome. Microdeletions are portions of a chromosome (often on the order of 2 million bases to about 10 million bases, but can be larger or smaller), and can cause significant deleterious effects to the fetus.

As further described herein, an initial dosage of a test chromosome or a portion thereof from a test maternal sample can be measured, and a statistical analysis (such as the determination of a value of likelihood that the test chromosome is abnormal or a value of statistical significance) can be performed. The statistical analysis can determine whether a call of normal (such as euploid or no microdeletion) or abnormal (such as aneuploidy or the presence of a microdeletion) for the test chromosome or portion thereof can be made within the desired level of confidence. In some embodiments, if the call cannot be made within the desired level of confidence or likelihood, the chromosome dosage is re-measured using an assay that provides a higher accuracy or precision (for example, by generating a greater number of quantifiable products, such as sequencing reads). The statistical analysis can be repeated, which can reveal whether, given the subsequent statistical results, a call of normal or abnormal for the test chromosome or portion thereof can be made within the desired level of confidence.

FIG. 1A illustrates the impact of fetal fraction and assay depth (specifically sequencing read depth) on resolving a triploid test chromosome (chromosome 21 in the illustrated example) dosage and an expected test chromosome dosage (which is expected to be diploid). In the example illustrated in FIG. 1, the test chromosome dosage is measured by aligning sequencing reads from the test chromosome; binning the aligned sequencing reads in a plurality of bins; counting the number of sequencing reads in each bin, including normalizing the number of sequencing reads in each bin for GC content and mappability; and determining a distribution for the number of reads per bin. The distribution for the aneuploid test chromosome and the expected distribution for the test chromosome (assuming disomy) is plotted (number of bins versus reads per bin). When the fetal fraction of cfDNA is high (right side of the figure), the sequencing depth needed to resolve the measured and expected test chromosomes is relatively low. However, when the fetal fraction of cfDNA is low (left side of figure) the sequencing depth needed to statistically distinguish the measured from the expected test chromosomes is relatively high.

Since the majority of test maternal samples will likely not require re-measurement of the test chromosome dosage, the subsequent assay may only need to be applied to a limited number of samples. By employing these methods, the cost for the noninvasive prenatal screen is more efficient (both in terms of cost and time) by minimizing the average assay depth while also yielding high sensitivity and specificity even at fetal fractions below which other noninvasive methods are able to call a normal or abnormal fetal chromosome within the desired confidence level. Because clinical guidelines recommend offering invasive diagnostic testing in the case of no-call (due to higher rates of aneuploidy in these samples), the reduced no-call rate from the methods provided herein helps reduce patient anxiety, unnecessary invasive procedures, and clinical workload burden.

Fetal fraction is influenced, in part, by the gestational age of the fetus and by the proportional size of the mother relative to the fetus. Pregnant women with a high body mass index (BMI) tend to have a lower fetal fraction at a similar gestational age. For example, women with a BMI greater than 30 are four times as likely to have a low fetal fraction of 2% to 4% (0.35 to 3.8 percentile) as women with a BMI under 30. Previous methods of noninvasive prenatal screening for aneuploidy are thus less likely to be useful for pregnant women with high BMI, or any other pregnant woman with a low fetal fraction of cfDNA. Furthermore, fetuses with chromosomal aneuploidy or certain microdeletions are more often undersized, further decreasing the fetal fraction of cfDNA. The methods described herein are more robust, and can more reliably provide screening for pregnant women with a high BMI, fetus with developmental anomalies, and at a younger gestational age. Additionally, the methods described herein may reduce the reflex rate of tested samples through improved Z-score calculations, improved background sample regressions, and utilization of clustered reference samples.

Moreover, noninvasive prenatal screening using whole-genome sequencing (WGS) identifies fetal chromosomal aneuploidies by measuring larger-than-expected deviations in the depth of sequenced cell-free DNA. A key determinant of test quality, therefore, is an accurate expectation of the disomic depth distribution, such that significant deviations are properly detected. Early implementations of the WGS method calculated expected disomic depth in a simple "one-dimensional" manner, using either the average depth of other "reference" chromosomes in the same sample or the average of the single chromosome of interest across the other 50-100 samples in the batch. These approaches have two drawbacks: (1) limited background observations (e.g., only 23 chromosomes), and (2) insufficient accounting for systematic biases—e.g., GC bias and total depth—between samples and chromosomes. The methods describe herein allow for determining an accurate expected disomic depth that is multidimensional, accounts for sources of bias, uses all chromosomes, and utilizes tens of thousands of samples Definitions As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "average" as used herein refers to either a mean or a median, or any value used to approximate the mean or the median. An "average mean" or "average median" refers to a mean or median (or any value used to approximate the mean or the median) of the means or medians (or approximate means or medians) from a plurality of distributions. An "average variation" refers to a mean or median (or any value used to approximate the mean or the median) of variations from a plurality of distributions. An "average distribution" refers to i) an average mean or an average median, and ii) an average variation, from a plurality of distributions.

A "bin" is an arbitrary genomic region from which a quantifiable measurement can be made. When multiple bins (i.e., a plurality of bins) are subjected to common analysis, the length of each arbitrary genomic region is preferably the same and tiled across a region of interest without overlaps. Nevertheless, the bins can be of different lengths, and can be tiled across the region of interest with overlaps or gaps.

A "chromosome dosage" is a quantitated amount of a chromosome, measured directly or indirectly, or a quantitated amount of an assay product representing a chromosome. The chromosome dosage may be represented as an absolute amount or as a distribution (including a mean or median (or an approximate value representing the mean or the median) and a variation). The chromosome dosage can be an integer (such as an integer number of chromosomes or an integer number of assay products) or a fraction (such as an amount of a chromosome indirectly measured based on a quantitated amount of an assay product representing the chromosome or a normalized amount of the assay product representing the chromosome).

An "expected chromosome dosage" is a chromosome dosage that would be expected if no fetal chromosomal abnormality were present.

A "fetal chromosomal abnormality" is any chromosomal copy number variant of the fetal genome relative to the maternal genome, including a microdeletion or chromosomal aneuploidy.

An "interrogated region" is any portion of a genome, which may be contiguous or non-contiguous, and can include one or more whole chromosomes or any one or more portions of any one or more chromosomes.

A "machine-learning model" is a predictive mathematical model—which may be implemented on a computer system—that uses an observed data set of numerical or categorical data to generate a predicted outcome data set of numerical or categorical data. The model can be "trained" on a plurality of observed data sets, wherein each of the observed data sets has a known outcome data set. Once trained, the model can be applied to a novel observed data set to yield a predicted outcome data set. The term "machine learning model" includes, but is not limited to, a regression model, a linear regression model, a ridge regression model, an elastic-net model, or a random-forest model.

A "mappable" sequencing read is a sequencing read that aligns with a unique location in a genome. A sequencing read that maps to zero or two or more locations in the genome is considered not "mappable."

A "maternal sample" refers to any sample taken from a pregnant mammal which comprises a maternal source and a fetal source of nucleic acids. The term "training maternal sample" refers to a maternal sample that is used to train a machine-learning model.

The term "maternal cell-free DNA" or "maternal cfDNA" refers to a cell-free DNA originating from a chromosome from a maternal cell that is neither placental nor fetal. The term "fetal cell-free DNA" or "fetal cfDNA" refers to a cell-free DNA originating from a chromosome from a placental cell or a fetal cell.

The term "normal" when used to characterize a putative fetal chromosomal abnormality, such as a microdeletion or aneuploidy, indicates that the putative fetal chromosomal abnormality is not present. The term "abnormal" when used to characterize a putative fetal chromosomal abnormality indicates that the putative fetal chromosomal abnormality is present.

A "variation" as used herein refers to any statistical metric that defines the width of a distribution, and can be, but is not limited to, a standard deviation, a variance, or an interquartile range.

A "value of likelihood" refers to any value achieved by directly calculating likelihood or any value that can be correlated to or otherwise indicative of likelihood. The term "value of likelihood" includes an odds ratio.

A "value of statistical significance" is any value that indicates the statistical distance of a tested event or hypothesis from a null or reference hypothesis, such as a Z-score, a p-value, or a probability.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention.

The section headings used herein are for organizational purposes only and are not to be construed as limiting the subject matter described.

Measuring Fetal Fraction

Certain regions of a genome may be over- or under-represented in the amount of fetal cell-free DNA versus maternal cell-free DNA. The amount of the over- or under-representation within these regions is proportional to the fetal fraction of cell-free DNA. Not all regions of the genome are over- or under-represented proportional to the fetal fraction of cfDNA. By binning the genome, or a portion thereof (such as an interrogated region, such as one or more chromosomes or a portion thereof), discreet portions of the genome can be isolated so that those specific regions can independently influence a machine-learning model. Measuring the amount of over- or under-representation of those regions can thus be used to indirectly measure the fetal fraction of cfDNA in a maternal sample by applying a trained machine-learning model.

In some embodiments, the fetal fraction of the cell-free DNA in a maternal sample is measured based on the over- or under-representation of fetal cell-free DNA from a plurality of bins within an interrogated region relative to maternal cell-free DNA. In some embodiments, the over- or under-representation of the fetal cell-free DNA is determined by a count of binned sequencing reads. In some embodiments, the over- or under-representation of the fetal cell-free DNA is determined by a count of binned hybridized probes.

In some embodiments, the fetal fraction of the cell-free DNA in a maternal sample is measured based on a count of binned sequencing reads from an interrogated region in the maternal sample. In some embodiments, the sequencing reads are aligned (for example, using a reference sequence), binned in a plurality of bins after being aligned, and the number of sequencing reads in each bin are counted. In some embodiments, the counted sequencing reads are normalized, for example to account for variations in GC content or mappability of the sequencing reads. Binning of the sequencing reads isolates discrete portions of the genome so that those specific regions can independently influence the trained model.

In some embodiments, the fetal fraction of the cell-free DNA in a maternal sample is measured based on a count of binned hybridized probes from an interrogated region in the maternal sample. In some embodiments, a plurality of probes hybridize to an interrogated region, the interrogated region is binned, and the number (or density) of probes that hybridize in each bin is counted. In some embodiments, the number or density of probes is determined using a fluorescence assay. In some embodiments, the probes are bound to a microarray.

A trained machine-learning model (such as a regression model, for example a linear regression model or a ridge regression model) is used to determine the measured fetal fraction based on the number of counts (e.g., sequencing reads or hybridized probes) in each of the bins. For example, the number of counts in the bin can be used to form a bin-count vector for any given test maternal sample, which is inputted into a trained machine-learning model to determine the fetal fraction. Optionally, the trained machine-model is a ridge regression model corrected by polynomial smoothing and/or an error reduction scaling process.

The machine-learning model can be trained using a training set. The training set includes a plurality of maternal samples (i.e., training maternal samples), wherein each training maternal sample has a known fetal fraction of cell-free DNA. One or more model coefficients can be determined based on the number of counts (such as sequencing reads or hybridized probes) in each bin and the known fetal fraction for each training maternal sample in the plurality of training maternal samples. The trained model can then be applied to the test maternal sample, which can indirectly measure the fetal fraction in the test maternal sample. The known fetal fraction from the training maternal samples can be determined, for example, by relying on the proportion of Y chromosome, the methylation differential between maternal and fetal cell-free DNA, the distribution of cfDNA fragment lengths, by sequencing polymorphic loci, or by any other known method.

In some embodiments, a sequencing library from each of the training maternal samples is prepared using cell-free DNA from the pregnant woman's serum. The cell-free DNA includes both maternal cell-free DNA and fetal cell-free DNA. The sequencing library is then sequenced (for example, using massive parallel sequencing, such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. In some embodiments, the sequencing reads are about 10 to about 1000 bases in length (such as about 10 to about 14 bases in length, about 14 to about 18 bases in length, about 18 to about 22 bases in length, about 22 to about 26 bases in length, about 26 to about 30 bases in length, about 30 to about 38 bases in length, about 38 to about 46 bases in length, about 46 to about 60 bases in length, about 60 to about 100 bases in length, about 100 to about 200 bases in length, about 200 to about 400 bases in length, about 400 to about 600 bases in length, about 600 to about 800 bases in length, or about 800 to about 1000 bases in length). In some embodiments, the sequencing reads are single-end reads and in some embodiments, the sequencing reads are paired-end reads. Sequencing paired end reads allows for the determination of the length of sequenced cell-free DNA. This information can be beneficial in training the machine-learning model, since maternal cell-free DNA is often, on average, longer than fetal cell-free DNA, and this differential can be used to determine fetal fraction. However, it has been found that training the machine-learning model using paired-end reads is not necessary, and substantial information can be gained from single-end reads alone. As single-end reads provide substantial time and cost savings, single-end reads are preferred.

The sequencing reads from an interrogated region from the training maternal samples are then aligned, for example using one or more reference sequences (such as a human reference genome). The interrogated region is those portions of the sequenced genome from the training maternal samples that are used to train the machine-learning model (e.g., the linear regression model or the ridge regression model). In some embodiments, the interrogated region is the whole genome. In some embodiments, the interrogated region excludes the X chromosome or the Y chromosome. In some embodiments, the interrogated region is one or more chromosomes, or one or more portions of one or more chromosomes. For example, the interrogated region can be a plurality of predetermined bins, which may be on the same chromosome or on different chromosomes.

The aligned sequencing reads from the interrogated region are binned in a plurality of bins. The bins are discrete regions along the genome or chromosome. Smaller bins provide higher resolution of the interrogated region. In some embodiments, the bins are about 1 base to about 1 chromosome in length (such as about 1 kilobases to about 200 kilobases in length (such as about 1 kilobases to about 5 kilobases, about 5 kilobases to about 10 kilobases, about 10 kilobases to about 20 kilobases, about 20 kilobases to about 50 kilobases, about 50 kilobases to about 100 kilobases, or about 100 kilobases to about 200 kilobases). In some embodiments, the interrogated region comprises about 100 bins to about 100,000 bins (such as between about 50 bins and about 100 bins, between about 100 bins and about 200 bins, between about 200 bins and about 500 bins, between about 500 bins and about 1000 bins, between about 1000 bins and about 2000 bins, between about 2000 bins and about 5000 bins, between about 5000 bins and about 10,000 bins, between about 10,000 bins and about 20,000 bins, between about 20,000 bins and about 40,000 bins, between about 40,000 bins and about 60,000 bins, between about 60,000 bins and about 80,000 bins, or between about 80,000 bins and about 100,000 bins). Preferably, the bins are of equal size.

The number of sequencing reads in each bin within the interrogated region for each training sample is counted. The counted sequencing reads for each bin are optionally normalized. Normalization can account for variations in GC content or mappability of the reads between the bins. For example, some bins within the interrogated region may have a higher GC content than other bins within the interrogation region. The higher GC content may increase or decrease the sequencing efficiency within that bin, inflating the relative number of sequencing reads for reasons other than fetal fraction. Methods to normalize GC content are known in the art, for example as described in Fan & Quake, PLoS ONE, vol. 5, e10439 (2010). Similarly, the certain bins within the interrogated region may be more easily mappable (or alignable to the reference interrogated region), and a number of sequencing reads may be excluded, thereby deflating the relative number of sequencing reads for reasons other than fetal fraction. Mappability at a given position in the genome can be predetermined for a given read length, k, by segmenting every position within the interrogated region into k-mers and aligning the sequences back to the interrogated region. K-mers that align to a unique position in the interrogated region are labeled "mappable," and k-mers that no not align to a unique position in the interrogated region are labeled "not mappable." A given bin can be normalized for mappability by scaling the number of reads in the bin by the inverse of the fraction of the mappable k-mers in the bin. For example, if 50% of k-mers within a bin are mappable, the number of observed reads from within that bin are scaled by a factor of 2. Normalization can also optionally include scaling the number of sequencing reads in each bin, for example by dividing the number of sequencing reads in each bin by the average of sequencing reads for the bins within the interrogated region.

For each training maternal sample, the numbers of sequencing reads (which may be normalized) for each bin are associated with a known fetal fraction of cell-free DNA for that training sample. The known fetal fraction may be determined using the chromosome dosage of the Y chromosome or the X chromosome (or both) of the training maternal sample. The chromosome dosage may be determined, for example, by aligning sequencing reads from the X or Y chromosome, which may be obtained simultaneously to the sequencing reads used for the interrogated regions. Because males have one Y chromosome and one X chromosome, whereas the pregnant mother has two X chromosomes and no Y chromosomes, the sequencing read density (i.e., reads per bin) of the X chromosome in male pregnancies should be $(1-e/2)$ relative to female pregnancies, wherein e is the fetal fraction of cell-free DNA (conversely, for the Y chromosome, the sequencing read density is $(1+e/2)$). The fetal dosage may be determined, for example, using the methods described in Fan & Quake, PLoS ONE, vol. 5, e10439 (2010) or U.S. Patent App. No. US 2010/0112575. In some embodiments, the sequencing reads for the X chromosome or the Y chromosome are aligned (for example, using a reference X chromosome or reference Y chromosome), the aligned sequencing reads are binned, and the number of sequencing reads in each bin are counted. In some embodiments, the numbers of sequencing reads are normalized, for example to account for variations in GC content or mappability. In some embodiments, the numbers of sequencing reads are scaled, for example by dividing by the average or median number of sequencing reads. In some embodiments, the fetal fraction is determined on the basis of the Y chromosome and the X chromosome separately. In some embodiments, to account for any systematic discrepancies between the calculation of fetal fraction from the X chromosome and the Y chromosome, the general relationship between fetal fraction inferred from the Y chromosome and the fetal fraction inferred from the X chromosome is modeled using a linear fit. The slope and intercept of the linear fit is used to scale the fetal fraction inferred from the X chromosome, and the known fetal fraction is the average of the fetal fraction inferred from the Y chromosome and the scaled fetal fraction inferred from the X chromosome (it works similarly well to perform scaling on fetal fraction estimated from the Y chromosome and then average the scaled Y-chromosome fetal fraction with the X-chromosome fetal fraction). Alternative methods of determining fetal fraction for the training maternal samples include methods relying on differential methylation of the maternal and fetal cell-free DNA or polymorphic loci.

The training maternal samples are preferably derived from male pregnancies (that is, a woman pregnant with a male fetus). In some embodiments, fetal fraction determined from the Y chromosome (i.e., $FF_Y$) and fetal fraction from the X chromosome (i.e., $FF_X$) can be determined separately. Optionally, an inferred fetal fraction from the X chromosome ($FF_{IX}$) is determined. An inferred fetal fraction from the X chromosome is generally preferable because it can provide more accurate fetal fraction determinations. $FF_{IX}$ can be determined by using a linear fit to model the relationship between $FF_Y$ and $FF_X$ for a plurality of the training maternal samples. A slope and intercept can be determined for the linear fit, and $FF_X$ can be used as an independent variable to determine the dependent variable $FF_{IX}$. The average of $FF_Y$ and $FF_{IX}$ (or $FF_Y$ and $FF_X$, if $FF_X$ is not used) can be determined, which can be used as the fetal fraction for the training maternal samples (that is, the observed fetal fraction, $FF_O$, for the training maternal samples). Although the observed fetal fraction is preferably determined using the fetal fraction determined from the X chromosome and the fetal fraction determined from the Y chromosome, in some embodiments the observed fetal fraction is determined only from the X chromosome or only from the Y chromosome.

The machine-learning model can be, for example, a regression model, such as a multivariate linear regression model or a multivariate ridge regression model. The machine-learning model can be trained to determine one or more model coefficients using the training maternal samples, each with a known fetal fraction and a vector including the sequencing read counts (which may be normalized) for the bins in the interrogation region. Exemplary linear regression models include elastic net (Enet) and reduced-rank regression with the rank estimated using the weighted rank selection criterion (WRSC), and further detailed in Kim et al., Prenatal Diagnosis, vol. 35, pp. 810-815 (2015) (including Supporting Information).

The machine-learning model can be trained using the fetal fraction and the bin counts (which may be normalized bin counts, or log 2 normalized bin counts) from the training maternal samples. The machine-learning model can be, for example, a linear model defined by:

$$FF_{i,regressed} = \vec{\beta} * \vec{x}_i + c$$

where $FF_{i,regressed}$ is the fetal fraction determined by the linear model, $\vec{x}_i$ is the bin-count vector for sample i, $\vec{\beta}$ is a regression coefficient vector, and c is the intercept of the model. The regression coefficient and the intercept can be determined by training the machine-learning model on the training maternal samples, for example, by linear regression or ridge regression. For example, the regression coefficient and the intercept can be determined by minimizing the square error with $L_2$ norm regularization with magnitude a according to:

$$\vec{\beta}, c = \operatorname{argmin}_{\beta,c}(FF_{i,regressed} - FF_{i,})^2 + \alpha \|\vec{\beta}\|^2$$

In some embodiments, the process of determining the regression coefficient includes scaling the bin counts ($d_{i,j}$) such that the median is set to 0 and the variance (e.g., the interquartile range) is set to 1 for each bin j across all training maternal samples used to train the machine-learning model (also referred to as a robust scalar transform). In some embodiments, the machine-learning model is trained using ridge regression. The ridge parameter α can be set by the user. Since the machine-learning model is underdetermined (that is, there are more bin count variables than fetal fraction outputs), the confidence in the model coefficients can be determined using a randomized k-fold validation (e.g., 10-fold validation) to iteratively determine the coefficients. For example, 90% of the training maternal samples (randomly selected) can be used for any given iteration, and the coefficients can be determined for 10 iterations with training maternal samples randomly selected for each iteration. In some embodiments, the regression model (such as a ridge regression model) is corrected by polynomial smoothing and/or an error reduction scaling process.

Polynomial smoothing of the trained machine-learning model can further improve the determined fetal fraction. Polynomial smoothing helps remove systematic bias artifacts. In some embodiments, a third-order polynomial is used to correct bias in the trained machine-learning model to arrive at a corrected fetal fraction (e.g., $FF_{corrected}$):

$$FF_{corrected} = c_0 + c_1 FF_{regressed} + c_2 FF_{regressed}^2 + c_3 FF_{regressed}^3$$

In some embodiments, the fetal fraction is corrected using a scalar error reduction process (which may be employed in addition to or in place of the polynomial smoothing of the trained machine-learning model). The machine-learning model may over or under predict the regressed or corrected fetal fraction ($FF_{regressed}$ or $FF_{corrected}$) of male or female pregnancies. To account for this, the regressed or corrected fetal fraction of the male or the female pregnancies can be multiplied by a scalar factor $\eta$. For example, in some embodiments, the fetal fraction for female pregnancies is under-predicted, and an inferred fetal fraction ($FF_{inferred}$) can be determined from the regressed or corrected fetal fraction as follows:

$$FF^{XY}_{inferred} = FF^{XY}_{corrected}$$

$$FF^{XX}_{inferred} = \eta FF^{XX}_{corrected}$$

where:

$$\eta = \frac{\text{average}(FF^{XY}_{corrected})}{\text{average}(FF^{XX}_{corrected})}$$

The average fetal fraction can be a median fetal fraction or a mean fetal fraction.

The trained machine-learning model can be used to estimate the fetal fraction of a test maternal sample. The test maternal sample may be from a woman with a male or female pregnancy. The fetal fraction of cell-free DNA in the test maternal sample is measured based on a count of binned sequencing reads from the interrogated region from the maternal sample. In some embodiments, a sequencing library is formed from the cell-free DNA from the test maternal sample. The sequencing library is then sequenced, for example using massive parallel sequencing (such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. Preferably, the same portions of the genome of the test maternal sample are sequenced as for the training maternal samples. Further, it is preferable that the sequencing reads should be the same length as used to sequence the training maternal samples. The sequencing reads can be paired-end reads or single-end reads, although single-end reads are generally preferred for efficiency.

The sequencing reads from the interrogated region of the test maternal sample are aligned, for example using one or more reference sequences. Preferably, the same reference sequence or sequences are used to align the test maternal sample as the training maternal sample. The aligned sequencing reads from the test maternal sample are binned using the same bin characteristics (that is, number of bins, size of bins, and location of bins).

The number of sequencing reads in each bin within the interrogated region for each test maternal sample is counted. If the counted sequencing reads for each bin are normalized for the training maternal samples, then the counted sequencing reads for the test maternal samples are similarly normalized. Normalization can account for variations in GC content or mappability of the reads between the bins. Normalization can also include scaling the number of sequencing reads in each bin, for example by dividing the number of sequencing reads in each bin by the mean or median number of sequencing reads for the bins within the interrogated region.

The number of sequencing reads in each bin of the interrogated region of the test maternal sample (which may be normalized) can then be received by the trained machine-learning model (e.g., the linear regression model or the ridge regression model), which outputs the indirectly measured fetal fraction for the test maternal sample. The measured fetal fraction of the test maternal sample can be corrected using the polynomial smoothing process (e.g., the third-order polynomial determined) or the scalar error reduction using the predetermined scalar factor $\eta$. In some embodiments, the measured fetal fraction of the test sample can be the regressed fetal fraction, the corrected fetal fraction, or the inferred fetal fraction.

Accurate fetal fraction for the test maternal sample can be measured at low sequencing depth. In some embodiments, the test maternal sample is sequenced at a genome-wide sequencing depth of about 6 million sequencing reads or more (such as about 7 million sequencing reads or more, about 8 million sequencing reads or more, about 9 million sequencing reads or more, about 10 million sequencing reads or more, about 11 million sequencing reads or more, about 12 million sequencing reads or more, about 13 million sequencing reads or more, about 14 million sequencing reads or more, or about 15 million sequencing reads or more). In some embodiments, the training maternal samples are sequenced at an average genome-wide sequencing depth of about 6 million sequencing reads or more (such as about 7 million sequencing reads or more, about 8 million sequencing reads or more, about 9 million sequencing reads or more, about 10 million sequencing reads or more, about 11 million sequencing reads or more, about 12 million sequencing reads or more, about 13 million sequencing reads or more, about 14 million sequencing reads or more, or about 15 million sequencing reads or more). Genome-wide sequencing depth refers to the number of sequencing reads that are generated when the full genome is sequenced. That is, if less than the full genome is sequenced (for example, an interrogated region of only predetermined regions), then the sequencing depth can be proportionately reduced.

The machine-learning model can be trained from a database of training maternal samples. The database of training maternal samples can be static, or additional training maternal samples can be added to the database over time (for example, as further maternal samples are sequenced). The training maternal samples can also be simultaneously assayed along with the test maternal sample, for example by massive parallel sequencing of the plurality of maternal samples (including the training maternal samples and the test maternal samples). For example, a plurality of maternal samples can be sequenced in parallel. The fetal fraction of maternal samples taken from women with male pregnancies can be determined based on the dosage of the Y chromosome or X chromosome. Those maternal samples from women with male pregnancies can then be used to train a machine-learning model that is used to determine the fetal fraction of remaining maternal samples taken from women with female pregnancies. By regularly retraining the machine-learning model, the model is controlled for fluctuations in laboratory conditions.

Measuring Chromosome Dosage

The dosage of the test chromosome or a test portion of a chromosome in the test maternal sample can be measured and compared to an expected dosage for the test chromosome (or test portion of the chromosome), where the expected dosage is the dosage if the test chromosome or portion thereof were normal (e.g., euploid or no microdeletion). Chromosome dosage can be measured, for example, using an assay that generates a plurality of quantifiable products (such as sequencing reads or PCR (such as digital PCR) products originating from the test chromosome), wherein the number of quantifiable products indicates the measured test chromosome dosage.

In some embodiments, the test chromosome or a test portion of the chromosome is selected from the maternal sample prior to generating the quantifiable products (i.e., selectively isolated from the maternal sample prior to generating the quantifiable products). Such methods for selection include, for example, selective capture (such as hybridization). In some embodiments, the quantifiable products used to measure the chromosome dosage can be selected after being generated, for example by filtering sequencing reads. In some embodiments, the quantifiable products are generated simultaneously to selecting the test chromosome or test portion of the chromosome, for example by selective PCR amplification.

The original source (i.e., fetal or maternal test chromosome) of the quantifiable products need not be distinguished, as the measured test chromosome dosage is used in conjunction with the measured fetal fraction, as explained below. Solely by way of example, if the test chromosome were chromosome 21, sequencing reads can be generated from both fetal chromosome 21 and maternal chromosome 21 in the test maternal sample. The generated sequencing reads can be treated identically and without regard to whether the origin of any particular sequencing read is fetal chromosome 21 or maternal chromosome 21.

Exemplary methods for determining chromosome dosage are described in Fan & Quake, PLoS ONE, vol. 5(5), e10439 (2010) and U.S. Pat. No. 8,008,018. Briefly, an assay can be performed to generate a plurality of quantifiable products from the test chromosome. As the fetal fraction in a maternal sample is usually relatively low, the majority of the quantifiable products that are generated will originate from the maternal cfDNA. However, a portion of the quantifiable products will originate from the fetal cfDNA. If, for example, the test chromosome from the fetal cfDNA is trisomic for the test chromosome, the number of resulting sequencing quantifiable products will be greater than would be expected if the fetal cfDNA were disomic for the test chromosome.

In some embodiments, a test portion of a chromosome is selected as a putative microdeletion. A microdeletion is a segment of chromosomal DNA missing in at least one fetal chromosome. Exemplary microdeletions include 22q11.2 deletion syndrome, 1p36 deletion syndrome, 15q11.2 deletion syndrome, 5p deletion syndrome, and 4p deletion syndrome The dosage of the portion of the chromosome with a microdeletion will be less than the expected dosage (that is, without the microdeletion). However, assuming a euploid chromosome, the remaining portions of chromosome with the putative microdeletion will have a measured dosage that is not statistically different from the expected dosage. The expected dosage can be determined, for example, from portions of the chromosome other than the putative region, or from other chromosomes or portions of other chromosomes in the genome. The microdeletion can be detected, for example, using circular binary segmentation techniques or by using a hidden Markov model search algorithm. See, for example, Zhao et al., Detection of Fetal Subchromosomal Abnormalities by Sequencing Circulating Cell-Free DNA from Maternal Plasma, Clinical Chemistry, vol. 61, pp. 608-616 (2015). For example, a sliding window along a chromosome can select a putative microdeletion and the chromosome dosage can be measured within the selected window (for example, a reads-per-bin distribution within any given window). The measured chromosome dosage of the putative microdeletion is compared to an expected dosage, and a value of likelihood of a microdeletion or a value of statistical significance can be determined, as further explained below. In some embodiments, the microdeletion is about 500,000 bases to about 15 million bases in length (for example, about 1 million to about 2 million bases in length, about 2 million to about 4 million bases in length, about 4 million to about 6 million bases in length, about 6 million to about 8 million bases in length, about 8 million to about 10 million bases in length, about 10 million to about 12 million bases in length, or about 12 million bases to about 15 million bases in length). In some embodiments, the microdeletion is more than about 15 million bases in length.

In some embodiments, the measured dosage is compared to an expected dosage (assumed normal) using statistical analysis. The statistical analysis can be used to evaluate the measured test chromosome dosage to determine a value of statistical significance (such as a Z-score, a p-value, or a probability) and/or value of likelihood that the test chromosome or portion thereof is abnormal.

In some embodiments, the dosage of the test chromosome (or portion thereof) is measured by aligning a plurality of sequencing reads from the test chromosome (or portion) in the maternal sample, binning the aligned sequencing reads in a plurality of bins, counting the number of sequencing reads in each bin, and determining a distribution for the number of reads per bin. The sequencing reads can be generated, for example, using massive parallel sequencing techniques. In some embodiments, the sequencing reads are generated using the same assay used to measure the fetal fraction of the maternal sample (that is, the sequencing reads used to measure the chromosome dosage are generated simultaneously as the sequencing reads used to measure the fetal fraction).

The sequencing reads generated from the test chromosome (or portion thereof) are aligned, for example using a reference sequence (such as a chromosome or portion from a human reference genome). The sequencing reads are then binned in a plurality of bins. In some embodiments, the bins are about 1 base to about one chromosome in length (such as about 1 kilobase to about 200 kilobases in length such as about 1 kilobases to about 5 kilobases, about 5 kilobases to about 10 kilobases, about 10 kilobases to about 20 kilobases, about 20 kilobases to about 50 kilobases, about 50 kilobases to about 100 kilobases, or about 100 kilobases to about 200 kilobases). In some embodiments, the interrogated region comprises about 1000 bins to about 100,000 bins (such as between about 1000 bins and about 2000 bins, between about 2000 bins and about 5000 bins, between about 5000 bins and about 10,000 bins, between about 10,000 bins and about 20,000 bins, between about 20,000 bins and about 40,000 bins, between about 40,000 bins and about 60,000 bins, between about 60,000 bins and about 80,000 bins, or between about 80,000 bins and about 100,000 bins). Preferably, the bins are of equal size.

The number of sequencing reads in each bin along the test chromosome is counted. Optionally, the counted sequencing reads for each bin are normalized, for example by accounting for variations in GC content or mappability of the reads between the bins. Normalization can also optionally include scaling the number of sequencing reads in each bin, for example by dividing the number of sequencing reads in each bin by the mean or median number of sequencing reads for the bins within the interrogated region.

A distribution of the number of reads per bin can be determined for the measured dosage. The distribution for the measured dosage can include, for example, an average (mean or median, or a value approximating a mean or a median), $\mu_{test}$, and a variation, $\sigma_{test}$ of the number of reads per bin. The variation can be, for example, a standard deviation or an interquartile range.

As chromosomal abnormality (such as aneuploidy or a microdeletion) is a relatively rare event compared to chromosomal normality (such as euploidy or no microdeletion), it can be assumed that the average dosage of each chromosome or portion thereof in a sufficiently large plurality of maternal samples reflects the expected dosage (i.e., normal for each chromosome or portion thereof). In some embodiments, the plurality of maternal samples comprises a plurality of external maternal samples. In some embodiments, the plurality of maternal samples comprises a plurality of external maternal samples and the test maternal sample.

The expected dosage (that is, assuming the test chromosome is normal) for the test maternal sample can be determined based on the measured dosage of one or more external maternal samples (that is, maternal samples other than the test maternal sample) and/or the test maternal sample. For example, in some embodiments, the measured dosage of one or more chromosomes (or portions thereof) other than the test chromosome (or portion thereof) from the test maternal sample is used to determine the expected dosage of the test maternal sample (or portion thereof). In some embodiments, the measured dosage of the test chromosome (or a portion thereof) from one or more external samples is used to determine the expected dosage of the test chromosome (or portion thereof) in the test maternal sample. In some embodiments, the measured dosage of the test chromosome (or a portion thereof) from one or more external samples and the measured dosage of the test chromosome (or portion thereof) from the test maternal sample is used to determine the expected dosage of the test chromosome (or portion thereof) in the test maternal sample. In some embodiments, the measured chromosome dosage of one or more chromosomes or portion thereof (which may or may not comprise the test chromosome or portion thereof) from one or more external maternal samples is used to determine the expected dosage of the test chromosome (or portion thereof) from the test maternal sample. In some embodiments, the measured chromosome dosage of one or more chromosomes or portion thereof (which may or may not comprise the test chromosome or portion thereof) from one or more external maternal samples and the measured chromosome dosage of one or more chromosomes or portion thereof (which may or may not comprise the test chromosome thereof) from the test maternal sample is used to determine the expected dosage of the test chromosome (or portion thereof) from the test maternal sample. In some embodiments, the one or more external maternal samples are the same as one or more of the training maternal samples used to train the machine-learning model used to determine the fetal fraction of the test maternal sample.

In some embodiments, the measured dosage includes an average number of reads per bin and a variation of the number of reads per bin. In some embodiments, the expected dosage of the test chromosome or the portion thereof is the measured dosage of the chromosome or the portion thereof other than the test chromosome or the portion thereof. Preferably, if the dosage of a portion of a chromosome is measured, the portion of the chromosome is on a different chromosome than the test chromosome portion.

In some embodiments, the expected dosage of a test chromosome or a portion thereof in a test maternal sample is determined by measuring the dosages of two or more chromosomes or portions thereof other than the test chromosome or the portion thereof in the test maternal sample. That is, the expected dosage is determined using a plurality of measured dosages (other than the test chromosome or portion thereof) internal to the test maternal sample. Each measured dosage can include an average number of reads per bin and a variation of the number of reads per bin. In some embodiments, an average distribution (or average mean or average median and an average variation) of the two or more measured dosages is determined. In some embodiments, the average distribution (or average mean or average median and average variation) is the expected dosage of the test chromosome or portion thereof. In some embodiments, the average distribution (or average mean or average median and average variation) of two or more, three or more, four or more, five or more, six or more, seven or more, eight or more, nine or more, or ten or more chromosomes or portions thereof other than the test chromosome or portion thereof is the expected chromosome dosage of the test chromosome or portion thereof. In some embodiments, the two or more chromosomes include all chromosomes other than the test chromosome or portion thereof or all autosomal chromosomes other than the test chromosome or portion thereof. In some embodiments, the test chromosome or portion thereof is further included in the average distribution to determine the expected dosage of the test chromosome or portion thereof.

In some embodiments, the expected dosage of the test chromosome or portion thereof in the test maternal sample is determined by measuring the dosage of the test chromosome or portion thereof in one or more external samples. For example, the measured dosage of the test chromosome (or portion thereof) from each of the external maternal samples can be averaged to obtain an average distribution (or average mean or average median and average variation). The average distribution determined from the measured dosages of the test chromosome from the plurality of external maternal samples can be used as the expected dosage of the test chromosome from the test maternal sample.

In some embodiments, the expected dosage of one or more chromosomes (such as a test chromosome) or a portion thereof for the test maternal sample is determined by measuring the dosage of one or more chromosomes from one or more external samples. For example, in some embodiments, the expected dosage of a test chromosome or a portion thereof for the test maternal sample is determined by training a machine-learning model using a plurality of external samples, and applying the machine-learning model to the measured dosage of one or more chromosomes or a portion thereof from the test sample. The one or more chromosomes or a portion thereof used to determine the expected dosage of the test chromosome or a portion thereof in the test sample can be all chromosomes in the genome, all autosomal chromosomes, all chromosomes in the genome excluding the test chromosome, all autosomal chromosomes excluding the test chromosome, or any portion thereof.

In some embodiments, a sequencing library from each of the training maternal samples is prepared using cell-free DNA from the pregnant woman's serum. The cell-free DNA includes both maternal cell-free DNA and fetal cell-free DNA. The sequencing library is then sequenced (for example, using massive parallel sequencing, such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. In some embodiments, the sequencing reads are about 10 to about 1000 bases in length (such as about 10 to about 14 bases in length, about 14 to about 18 bases in length, about 18 to about 22 bases in length, about 22 to about 26 bases in length, about 26 to about 30 bases in length, about 30 to about 38 bases in length, about 38 to about 46 bases in length, about 46 to about 60 bases in length, about 60 to about 100 bases in length, about 100 to about 200 bases in length, about 200 to about 400 bases in length, about 400 to about 600 bases in length, about 600 to about 800 bases in length, or about 800 to about 1000 bases in length). In some embodiments, the sequencing reads are single-end reads and in some embodiments, the sequencing reads are paired-end reads. Sequencing paired end reads allows for the determination of the length of sequenced cell-free DNA. This information can be beneficial in training the machine-learning model, since maternal cell-free DNA is often, on average, longer than fetal cell-free DNA, and this differential can be used to determine fetal fraction. However, it has been found that training the machine-learning model using paired-end reads is not necessary, and substantial information can be gained from single-end reads alone. As single-end reads provide substantial time and cost savings, single-end reads are preferred.

The sequencing reads from an interrogated region from the training maternal samples are then aligned, for example using one or more reference sequences (such as a human reference genome). The interrogated region may include those portions of the sequenced genome from the training maternal samples that are used to train the machine-learning model. In some embodiments, the interrogated region may include the whole genome. In some embodiments, the interrogated region may exclude the X chromosome or the Y chromosome. In some embodiments, the interrogated region may be one or more chromosomes, or one or more portions of one or more chromosomes. For example, the interrogated region can be a plurality of predetermined bins, which may be on the same chromosome or on different chromosomes.

The aligned sequencing reads from the interrogated region may be binned in a plurality of bins. The bins are discrete regions along the genome or chromosome. Smaller bins provide higher resolution of the interrogated region. In some embodiments, the bins are about 1 base to about 1 chromosome in length (such as about 1 kilobases to about 200 kilobases in length (such as about 1 kilobases to about 5 kilobases, about 5 kilobases to about 10 kilobases, about 10 kilobases to about 20 kilobases, about 20 kilobases to about 50 kilobases, about 50 kilobases to about 100 kilobases, or about 100 kilobases to about 200 kilobases). In some embodiments, the interrogated region comprises about 100 bins to about 100,000 bins (such as between about 50 bins and about 100 bins, between about 100 bins and about 200 bins, between about 200 bins and about 500 bins, between about 500 bins and about 1000 bins, between about 1000 bins and about 2000 bins, between about 2000 bins and about 5000 bins, between about 5000 bins and about 10,000 bins, between about 10,000 bins and about 20,000 bins, between about 20,000 bins and about 40,000 bins, between about 40,000 bins and about 60,000 bins, between about 60,000 bins and about 80,000 bins, or between about 80,000 bins and about 100,000 bins). Preferably, the bins are of equal size.

The number of sequencing reads in each bin within the interrogated region for each training sample is counted. The counted sequencing reads for each bin are optionally normalized. Normalization can account for variations in GC content or mappability of the reads between the bins. For example, some bins within the interrogated region may have a higher GC content than other bins within the interrogation region. The higher GC content may increase or decrease the sequencing efficiency within that bin, inflating the relative number of sequencing reads for reasons other than fetal fraction. Methods to normalize GC content are known in the art, for example as described in Fan & Quake, PLoS ONE, vol. 5, e10439 (2010). Similarly, the certain bins within the interrogated region may be more easily mappable (or alignable to the reference interrogated region), and a number of sequencing reads may be excluded, thereby deflating the relative number of sequencing reads for reasons other than fetal fraction. Mappability at a given position in the genome can be predetermined for a given read length, k, by segmenting every position within the interrogated region into k-mers and aligning the sequences back to the interrogated region. K-mers that align to a unique position in the interrogated region are labeled "mappable," and k-mers that no not align to a unique position in the interrogated region are labeled "not mappable." A given bin can be normalized for mappability by scaling the number of reads in the bin by the inverse of the fraction of the mappable k-mers in the bin. For example, if 50% of k-mers within a bin are mappable, the number of observed reads from within that bin are scaled by a factor of 2. Normalization can also optionally include scaling the number of sequencing reads in each bin, for example by dividing the number of sequencing reads in each bin by the average of sequencing reads for the bins within the interrogated region.

Background Regression Modelling

In some embodiments, a machine-learning model (e.g., a robust regression model) may be trained using a measured dosage of a test chromosome or portion thereof and a measured dosage of at least one chromosome or portion thereof other than the test chromosome or portion thereof in a plurality of reference maternal samples, and the machine learning model may be applied to the measured dosage of the at least one chromosome or portion thereof other than the test chromosome or portion thereof in a test maternal sample to determine the expected chromosome dosage of the test chromosome or portion thereof in the test maternal sample. For example, the machine-learning model may be trained using measured dosages of a plurality of chromosomes or all chromosomes (or portions thereof) in the plurality of reference maternal samples.

The trained model may be applied to a dosage distribution vector comprising the dosages from each of the at least one chromosome or portion thereof other than the test chromosome or portion thereof from the test maternal sample to obtain the expected dosage of the test chromosome or portion thereof. In some embodiments, the dosage distribution vector may include an average (mean or median) dosage vector and a variation dosage vector (for example, the average reads per bin can be determined independently from the variation of the number of reads per bin). In some embodiments, the plurality of maternal samples may include the test maternal sample. In some embodiments, the plurality of maternal samples may exclude the test maternal sample. In some embodiments, the at least one chromosome or portion thereof other than the test chromosome or portion thereof may include all chromosomes other than the test chromosome or portion thereof or all autosomal chromosomes other than the test chromosome or portion thereof. In some embodiments, the at least one chromosome or portion thereof other than the test chromosome may further include the test chromosome.

The machine-learning model can be trained using a training set. The training set includes a plurality of maternal samples (i.e., reference maternal samples or training maternal samples), wherein each reference maternal sample has a known dosage for a plurality of chromosomes or all chromosomes (or portions thereof) in the reference maternal sample. One or more model coefficients can be determined based on the number of counts (such as sequencing reads or hybridized probes) in each bin. The trained model can then be applied to the test maternal sample determine the dosage of the test chromosome (or portion thereof) in the test maternal sample.

The machine-learning model can be, for example, a robust regression model that is robust against outliers, such as a maximum likelihood type regression model (e.g., M-estimation or Huber regression model), a least trimmed squares regression model, a MM-estimation regression model, or any other suitable robust regression model, without limitation. The machine-learning model can be trained to determine one or more model coefficients using the reference maternal samples (i.e., training maternal sample), each with a known vector including the sequencing read counts (which may be normalized) for the bins in the interrogation region.

The machine-learning model can be trained using the bin counts (which may be normalized bin counts, or $\log_2$ normalized bin counts) from the reference maternal samples. The machine-learning model can be, for example, based on a linear model defined by:

$$\mu_i = \sum_{j \neq i} \beta_j x_j$$

where $\mu_i$ is the mean or median for the expected dosage distribution of a test chromosome of a sample i determined by the regression model, $x_j$ is the bin vector for the test chromosome of sample j, and $\beta_j$ is a regression coefficient for the test chromosome of sample j. The machine-learning model may utilize a weight function that varies based on at least one of an average number of sequencing reads per bin and a variation of the number of sequencing reads per bin for portions of the interrogated region, such as portions corresponding to particular chromosomes (or portions thereof), and the regression coefficient can be determined by minimizing the square error with $L_2$ norm regularization with a magnitude parameter $\alpha$ according to:

$$\ell(\vec{\beta}) = \alpha \|\vec{\beta}\|^2 + \sum_{samples} \begin{cases} (x-\mu)^2 & \text{if } \frac{x-\mu}{\sigma} < 3 \\ |x-\mu| & \text{if } \frac{x-\mu}{\sigma} \geq 3 \end{cases}$$

In some embodiments, the magnitude parameter $\alpha$ can be set by the user. In some embodiments, the regression model may be corrected by polynomial smoothing and/or an error reduction scaling process.

The trained machine-learning model can be used to estimate the mean or median for an expected dosage distribution of a test chromosome of a test maternal sample. The test maternal sample may be from a woman with a male or female pregnancy. In some embodiments, a sequencing library may be formed from the cell-free DNA from the test maternal sample. The sequencing library then be sequenced, for example using massive parallel sequencing (such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. The same portions of the genome of the test maternal sample may be sequenced as for the training maternal samples. Further, the sequencing reads may be the same length as used to sequence the reference maternal samples utilized to train the machine-learning model. The sequencing reads can be paired-end reads or single-end reads, although single-end reads are generally preferred for efficiency.

The sequencing reads from the interrogated region of the test maternal sample may be aligned, for example using one or more reference sequences. The same reference sequence or sequences may be used to align the test maternal sample as the training maternal sample. The aligned sequencing reads from the test maternal sample may be binned using the same bin characteristics (that is, number of bins, size of bins, and location of bins).

The number of sequencing reads in each bin within the interrogated region for each test maternal sample may be counted. If the counted sequencing reads for each bin are normalized for the reference maternal samples, then the counted sequencing reads for the test maternal samples may be similarly normalized. Normalization can account for variations in GC content or mappability of the reads between the bins. Normalization can also include scaling the number of sequencing reads in each bin, for example by dividing the number of sequencing reads in each bin by the mean or median number of sequencing reads for the bins within the interrogated region. The number of sequencing reads in each bin of the interrogated region of the test maternal sample (which may be normalized) can then be received by the trained machine-learning model (e.g., the linear regression model or the ridge regression model), which outputs an expected dosage for the test chromosome (or portion thereof) for the test maternal sample.

Depth-Scaled Statistical Analysis

A statistical test (such as a Z-test) can be used to determine whether the measured dosage is statistically different from the expected dosage (i.e., the normal chromosome null hypothesis). To conduct the statistical test, a value of statistical significance is determined and compared to a predetermined threshold. If the value of statistical significance is above the predetermined threshold, the null hypothesis (that is, that the test chromosome is normal) can be rejected.

In some embodiments, the value of statistical significance is a Z-score. In some embodiments, the Z-score is determined using the following formula:

$$Z = \frac{x_{test} - \mu_{exp}}{\sigma_{exp}}$$

where $x_{test}$ is the mean or median for the measured dosage distribution of the test chromosome (or portion thereof), $\mu_{exp}$ is the mean or median for the expected dosage distribution, and $\sigma_{exp}$ is the variation (such as standard deviation or interquartile range) for the expected dosage distribution.

The value of statistical significance is highly correlated with fetal fraction for an aneuploid test chromosome in the test maternal sample. That is, among maternal samples that are abnormal for the test chromosome (or portion thereof), those maternal samples with a higher fetal fraction of cfDNA will have a higher absolute value of statistical significance. However, for those maternal samples with normal test chromosome, the value of statistical significance does not substantially change for differences in fetal fraction. Thus, maternal samples having low fetal fraction and abnormal test chromosome (or portion thereof) may have a value of statistical significance near those maternal samples having a normal test chromosome (or portion thereof), particularly when the sequencing depth is low. Thus, a value of likelihood that the fetal cell-free DNA is abnormal for the test chromosome can be determined based on the measured test chromosome dosage and the expected test chromosome dosage (for example, by using the Z-score), as well as the fetal fraction. This value of likelihood can be expressed as, for example an odds ratio that the test chromosome (or portion thereof) is abnormal versus normal. See, for example, U.S. Pat. No. 8,700,338.

Figure 1B:
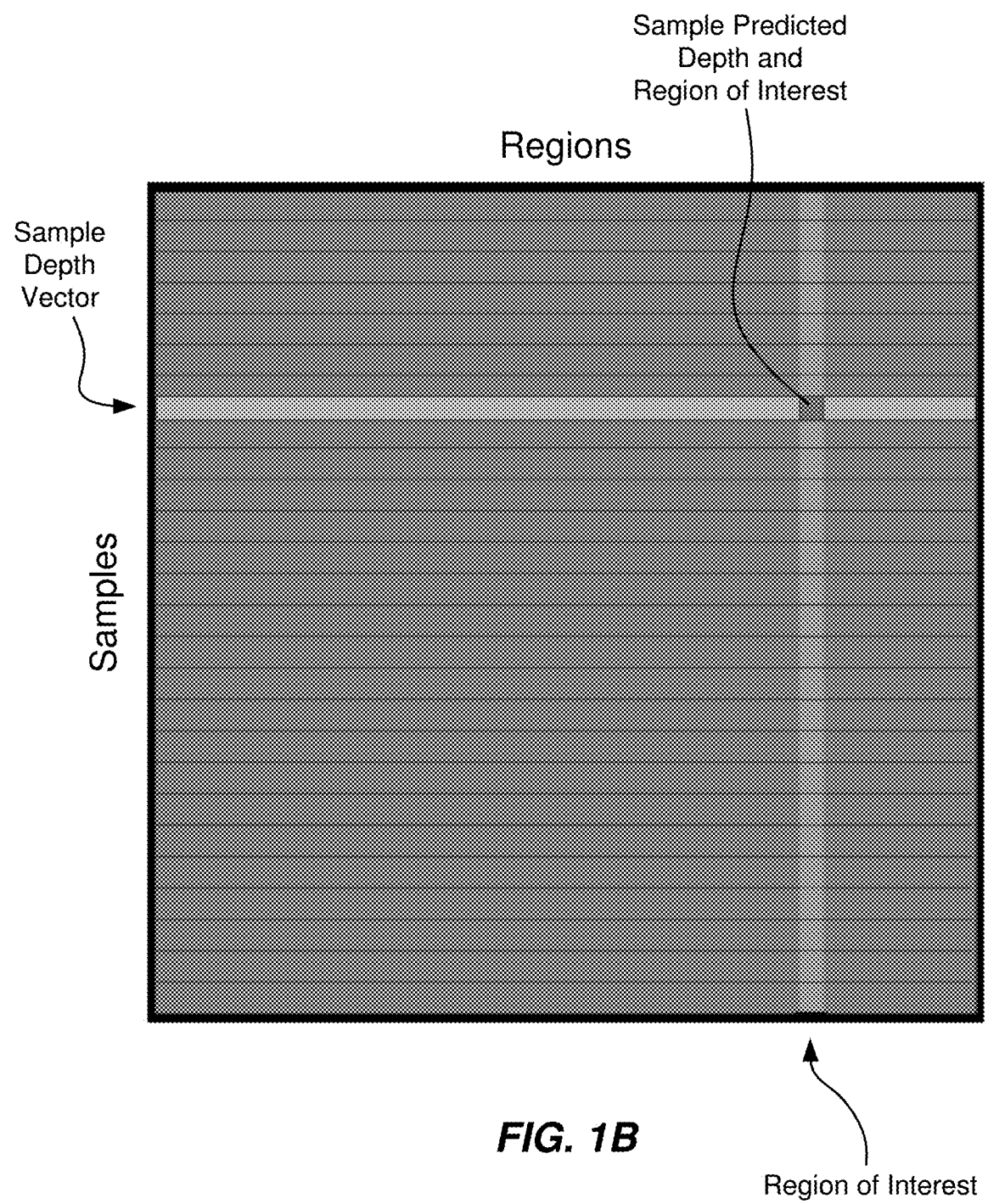
FIG. 1B illustrates utilization of a regression model for background prediction for a sample and region of interest.

The Z-score for a sample may vary with assay sampling depth. For example, a variation used to calculate the Z-score may decrease with increasing sampling depth, resulting in lower Z-scores for test maternal samples assayed at a lower sampling depth. As illustrated in FIG. 1B, in Z-score calculation for a sample and region of interest, the disomic normalized depth may be predicted by (1) training a regression model where other samples' depth vectors are regressed onto the region of interest, and (2) applying the regression to the sample's depth vector to yield a predicted depth. To reduce risk of an aneuploid region in the depth vector compromising the regression, robust regression methods, such as those described above, are preferred.

The background used for determining the variation $\sigma_{exp}$ for the expected dosage distribution may also affect the Z-score. In some embodiments, the Z-score may be determined by calculating a depth-scaled variation $\sigma_d$ that is correlated to the sampling depth of the test maternal sample. Additionally or alternatively, the Z-score may be determined by calculating a cohort-based variation $\sigma_c$ using a plurality of cohort reference maternal samples that are selected based on one or more similarities between the cohort reference maternal samples and the test maternal sample.

In some embodiments, the Z-score may be determined for a test chromosome of a test maternal sample using a model that takes into account both depth-scaled variation $\sigma_d$ and cohort-based variation $\sigma_c$. For example, the Z-score may be determined according to the following formula:

$$\sigma_{exp}^2 = \sigma_c^2 + \frac{\sigma_d^2}{d}$$

where $\sigma_c$ is the cohort-based variation (such as standard deviation or interquartile range) for the plurality of cohort reference maternal samples, $\sigma_d$ is the depth-scaled variation (such as standard deviation or interquartile range) for a population of reference maternal samples assayed at a particular sequencing depth or range of sequencing depths, and d is the sequencing depth of the test maternal sample.

In some embodiments, $\sigma_{exp}$ may be determined for the test chromosome (or portion thereof) based on a maximum likelihood parameter estimation model. For example, $\sigma_c$ may be determined from the measurements of the cohort reference maternal samples according to:

$$\sigma_c^2 = \frac{1}{N} \sum_{i \in cohort} (x_i - \mu_i)^2 \frac{1 - d_i \langle d_i^{-1} \rangle}{1 - \langle d_i \rangle \langle d_i^{-1} \rangle}$$

where $x_i$ is the mean or median for the measured dosage distribution of reference maternal sample i of the plurality of cohort reference maternal samples, $\mu_i$ is the mean or median for the expected dosage distribution of sample i, and $d_i$ is the measured sequencing depth of sample i. Because the plurality of cohort reference maternal samples is selected based on similarities in characteristics of the test maternal sample and reference maternal samples of the plurality of cohort reference maternal samples, $\sigma_c$ may be more closely correlated to each individual test maternal sample and may vary from test maternal sample to test maternal sample based on the corresponding plurality of cohort reference maternal samples selected. In at least one embodiment, $\sigma_c$ may be determined based on variations calculated for the plurality of cohort reference maternal samples, regardless of the sequencing depths to which the cohort reference maternal samples were assayed.

In some embodiments, $\sigma_d$ may be determined for a particular sequencing depth from a population of reference maternal samples according:

$$\sigma_d^2 = \frac{1}{N} \sum_i (x_i - \mu_i)^2 \frac{d_i - \langle d_i \rangle}{1 - \langle d_i \rangle \langle d_i^{-1} \rangle}$$

where $x_i$ is the mean or median for the measured dosage distribution of sample i, $\mu_i$ is the mean or median for the expected dosage distribution of sample i, and $d_i$ is the measured sequencing depth of sample i. The population of reference maternal samples used to calculate $\sigma_d$ may be larger than the plurality of cohort reference maternal samples used to calculate $\sigma_c$ and may include some or all of the reference maternal samples included in the plurality of cohort reference maternal samples.

In some embodiments, $\sigma_d$ may be calculated in advance for various chromosomes at each of a plurality of depths. For example, a large population of reference maternal samples (e.g., thousands of references samples, tens of thousands of reference maternal samples, or more) measured at various depths may be used to calculate $\sigma_d$ for one or more test chromosomes (or portions thereof) at a plurality of leaching depths. As an example, Table 1 summarizes a plurality of exemplary predetermined $\sigma_d$ values corresponding to various chromosomes and sequencing depths.

TABLE 1

Exemplary $\sigma_d$ values determined for chromosomes 13-22 at various sequencing depths.

| Chromosome | Sequencing Depth | | |
|---|---|---|---|
| | 15 mil | 30 mil | 45 mil |
| chr13 | 0.003766 | 0.003251 | 0.003061 |
| chr14 | 0.003405 | 0.002996 | 0.002846 |
| chr15 | 0.004173 | 0.003922 | 0.003835 |
| chr16 | 0.004274 | 0.003637 | 0.003397 |
| chr17 | 0.006049 | 0.005819 | 0.00574 |
| chr18 | 0.00412 | 0.003533 | 0.003314 |

TABLE 1-continued

Exemplary $\sigma_d$ values determined for chromosomes 13-22 at various sequencing depths.

| Chromosome | Sequencing Depth | | |
|---|---|---|---|
| | 15 mil | 30 mil | 45 mil |
| chr20 | 0.004252 | 0.003781 | 0.00361 |
| chr21 | 0.005442 | 0.004444 | 0.004057 |
| chr22 | 0.006158 | 0.005603 | 0.005405 |

In some embodiments, an expected variation determined based on $\sigma_c$ and $\sigma_d$ may be utilized to determine a Z-score for a test chromosome of a test maternal sample assayed at a particular sequencing depth or range of sequencing depths with greater accuracy. For example, the Z-score for the test chromosome may be determined based on an expected variation value that is calculated using a $\sigma_d$ that is correlated to a number of sequencing reads obtained from an assay of the test maternal sample and a $\sigma_c$ that is calculated based on a plurality of cohort reference maternal samples having one or more similarities to the test maternal sample.

In at least one embodiment, the expected variation determined based on $\sigma_c$ and $\sigma_d$ may be utilized to determine the effect on the Z-score of increasing the assay depth for a test maternal sample. For example, correlations between expected variations at different sequencing depths for a test chromosome may be used to predict a resulting Z-score for a test maternal sample if the test maternal sample were sequenced using a higher depth assay. In some examples, a predicted Z-score for the test chromosome or the portion thereof of the test maternal sample may be determined based on an additional depth-scaled variation value $\sigma_d$ that is correlated to a higher number of sequencing reads that is higher than a number of sequencing reads obtained from the test maternal sample.

Reference Sample Clustering

In some embodiments, reference maternal samples utilized in chromosomal abnormality determinations, as described herein, may be selected based on similarities between the reference maternal samples and the test maternal samples. For example, out of a broader population of reference maternal samples, a group of reference maternal samples that are most like the test maternal sample may be utilized in analysis of the test maternal sample. Similarities in one or more characteristics of the test maternal sample and the reference maternal samples may be used to identify a suitable sub-set of reference maternal samples (i.e., cohort reference maternal samples). Reference maternal samples selected in this manner may be used for determining any suitable manner for chromosomal abnormality determinations according to any of the methods described herein. In some embodiments, values of statistical significance (such as Z-scores) may be determined, at least in part, for a test maternal sample using reference maternal samples selected based on similarities to the test maternal sample. In at least one embodiment, cohort reference maternal samples for a test maternal sample may be identified based on similarities to the test maternal sample and may be utilized to calculate a cohort-based variation value, $\sigma_c$, used in the calculation of expected variation value, $\sigma_{exp}$, used in the calculation of Z-scores. In some embodiments, cohort reference samples may be utilized in robust regression modeling to determine a mean or median, $\mu_{exp}$, for the expected dosage distribution.

In some embodiments, a broad population of reference maternal samples may be analyzed and clustered (e.g., k-means clustering or hierarchical clustering) to generate a number of clusters that each include a plurality of reference maternal samples. In some embodiments, reference maternal samples may be clustered through k-means clustering based on identified characteristics of reference maternal samples. In some embodiments, a predetermined number of clusters may be generated from a population of reference maternal samples and the clusters may each include a specified number of reference maternal samples. In some embodiments, centroids of the clusters may be identified. For each of the clusters, a specified number of reference maternal samples closest to a centroid of the cluster may be determined to be in the cluster. In some embodiments, at least some reference maternal samples may be located within more than one cluster. In some embodiments, clusters utilized in analysis of a test maternal sample may be selected based on the proximity of the centroids for the clusters to the test maternal sample. For example, clusters may be selected based on proximities of the clusters to the test maternal sample and/or based on one or more clusters being located closest to the test maternal sample.

Any suitable characteristics of reference maternal samples may be utilized in clustering the reference maternal samples. For example, characteristics of sequencing reads obtained from each of the reference maternal samples may be used to generate clusters. In some embodiments, k-means clusters may be generated based on Z-scores of various measurable metrics for the reference maternal samples. In at least one embodiment, clusters may be generated based on Z-scores of values for the reference maternal samples related to GC bias, binned sequencing depth, normalized chromosomal median, and/or any other suitable metrics. Reference maternal samples may be clustered once or periodically. In some embodiments, reference maternal samples may be clustered dynamically during testing of test maternal samples.

Likelihood Determinations

A value of likelihood that the fetal cell-free DNA in the test maternal sample is abnormal (for example, aneuploid or has a microdeletion) for the test chromosome or test portion thereof can be determined based on the measured dosage of the test chromosome or portion thereof, the expected dosage of the test chromosome, and the measured fetal fraction. In some embodiments, the value of likelihood is determined by determining a value of statistical significance (such as a Z-score) for the test chromosome (or portion thereof) based on the measured dosage and the expected dosage; and then determining the value of likelihood of abnormality based on the value of statistical significance and the measured fetal fraction.

The value of likelihood of an abnormal chromosome (or portion thereof) can be determined using a model assuming a normal fetal test chromosome (or portion thereof) and/or a model assuming an abnormal fetal test chromosome (or portion thereof). The models can be developed, for example, using a Monte Carlo simulation to estimate the difference between the measured test chromosome dosage and the expected chromosome dosage (which may be, for example, expressed as $(\mu_{test} - \mu_{exp})$ or a value of statistical significance) for randomly generated maternal samples drawn from empirical samples. The empirical samples can include, for example, samples taken from verified abnormal maternal samples with known fetal fraction and samples taken from non-pregnant women (where the fetal fraction is defined as 0 and the measured test chromosome dosage equals the expected dosage). The models provide a distribution of estimated difference between the measured test chromosome dosage and the expected chromosome dosage for a specified fetal fraction.

In some embodiments, the value of likelihood for an abnormal test chromosome from the test maternal sample is expressed as an odds ratio:

$$\frac{P(x_i|A)}{P(x_i|E)}$$

wherein $P(x_i|A)$ is the probability that the difference between the measured test chromosome or portion thereof (i) dosage (which, for example, may be expressed as ($\mu_{test}-\mu_{exp}$) or a Z-score), $x_i$, can be attributed to aneuploidy, A, and $P(x_i|E)$ is the probability that the difference between the measured test chromosome dosage (which, for example, may be expressed as ($\mu_{test}-\mu_{exp}$) or a Z-score), $x_i$, can be attributed to euploidy, E.

In some embodiments, the value of likelihood that the fetal cell-free DNA is abnormal for the test chromosome accounts for the probability that the measured fetal proportion is reflective of a true fetal fraction. When the fetal fraction is measured using any known method or the method described herein, there is some probability that the measured fetal fraction is reflective of the true fetal fraction. The value of likelihood that the fetal test chromosome from the test maternal is abnormal can be determined using the abnormal model and/or the normal model at any given fetal fraction, but this value of likelihood can also be adjusted using a weighted average across a spectrum of possible fetal fractions, wherein the probability of aneuploidy for a given fetal fraction is weighted by the probability that the measured fetal fraction reflects the true fetal fraction. This accounting can be reflected as follows:

$$P(A_i|FF_m, x_i) = \int_{FF_t} P(A_i|FF_t, x_i) \times P(FF_t|FF_m)$$

wherein $FF_m$ is the measured fetal fraction and $FF_t$ is the true fetal fraction. The term $P(A_i|FF_t, x_i)$ represents the probability of aneuploidy relative to the summed probability of euploidy and aneuploidy. Specifically:

$$P(A_i|FF_t, x_i) = \frac{P(z_i|\mu_{i,aneuploid}, \sigma_{i,aneuploid})}{P(z_i|\mu_{i,aneuploid}, \sigma_{i,aneuploid}) + P(z_i|\mu_{i,euploid}, \sigma_{i,euploid})}$$

where $\mu_{i,euploid}=0$, $\sigma_{i,euploid}=1$ ($\sigma$ achieves a normalized value of 1 after dividing all un-normalized values of statistical significance (e.g., Z-scores) by the standard deviation of un-normalized statistical significance (e.g., Z-scores)), and $\mu_{aneuploid}$, and $\sigma_{aneuploid}$ are functions of fetal fraction (e.g., a linear model can be fit to a set of aneuploidy samples where both the fetal fraction and Z-score are known; thus, the mean and standard deviation of Z-scores for a particular fetal fraction can be inferred from the linear model). The probabilities themselves are calculated by noting that the values of statistical significance (e.g., Z-score) distributions are Gaussian—thus completely characterized by the mean, $\mu$, and standard deviation, $\sigma$—and using the Gaussian probability-density function to calculate the probability of a given z-score. The probability that the measured fetal proportion is reflective of a true fetal fraction can be determined, for example, by modeling a Gaussian distribution centered on the measured fetal fraction, with the distribution determined from maternal samples with known fetal fractions. The Gaussian is fit to the distribution of observed differences between the true fetal fraction and the measured fetal fraction for a plurality of samples. The difference between the true fetal fraction and the measured fetal fraction can be measured by applying the trained machine-learning model on a set of maternal samples with known fetal fraction (such as from maternal samples with male pregnancies). The distribution of differences between the true fetal fraction and the measured fetal fraction for the set of maternal samples with male pregnancies can be fit by a Gaussian model to yield mean, $\mu$, and standard deviation, $\sigma_{FF}$; which is then applied to the test maternal sample. Thus, to calculate $P(FF_t|FF_m)$, the Gaussian probability density function can be used where the mean, $\mu$, is set to $FF_m$ and the standard deviation is $\sigma_{FF}$. In some embodiments, the maternal samples used to generate the model distribution comprise the training maternal samples.

Abnormal Chromosome Calling and Dynamic Iterative Depth Optimization

In some embodiments, the test chromosome is called as abnormal (e.g., aneuploid or microdeletion) or normal (e.g., euploid or no microdeletion) using an initially determined value of statistical significance (such as a Z-score) and/or value of likelihood of abnormality. In some embodiments, the test chromosome (or portion thereof) is not called as abnormal or normal using the initially determined value of statistical significance or value of likelihood, and the test chromosome dosage is re-measured and a subsequent value of statistical significance and/or subsequent value of likelihood is determined. The re-measured dosage of the test chromosome (or portion thereof) is re-measured using a higher accuracy assay. For example, the dosage of the test chromosome (or portion thereof) can be measured by analyzing a greater number of quantifiable products (such as sequencing reads).

In some embodiments, if the initial value of statistical significance is above a predetermined threshold, the test chromosome (or portion thereof) from the test maternal sample is called as abnormal (e.g., aneuploid or microdeletion) for the fetal cfDNA. It should be noted that when evaluating the value of statistical significance (such as a Z-score) against a predetermined threshold, the absolute value of the value is preferably considered. This is because, in some instances, the aneuploid test chromosome has only a single copy (i.e., monoploid) originating from the fetal cfDNA, whereas the test chromosome would be expected to have two copies (i.e., diploid). An example of this is Turner syndrome, wherein the fetus has monosomy X. The measured test chromosome dosage would thus be less than the expected chromosome dosage, and the Z-score could be computed as a negative value. Similarly, in the circumstance of a microdeletion, an abnormal chromosome with a microdeletion would result in a lower measured dosage than a normal chromosome without the microdeletion. Thus, it is equivalent to call the test chromosome (or portion thereof) as abnormal for the fetal cfDNA when a positive value of statistical significance (e.g., Z-score) is above a positive predetermined threshold as it is to call the test chromosome as abnormal for the fetal cfDNA when a negative value of statistical significance is below a negative predetermined threshold. However, when making a specific call of fewer copies of the test chromosome (or portion thereof) in the fetal cfDNA than the expected number of copies, such as in the case of monosomy X or a microdeletion, then the call can be made when the value of statistical significance is below a negative predetermined threshold.

When the absolute value of the statistical significance is above the predetermined threshold, the measured dosage of the test chromosome (or portion thereof) is sufficiently above (or below, the case of a negative predetermined threshold) the expected dosage that the call of abnormality (such as aneuploidy or microdeletion) can be made with the desired confidence level. The desired confidence level can be used to set the predetermined threshold. In some embodiments, the desired one-tailed confidence level (a) is about 0.05 or lower (such as about 0.025 or lower, about 0.01 or lower, about 0.005 or lower, or about 0.001 or lower). In some embodiments, the predetermined threshold for the Z-score is about 2 or higher (such as about 2.5 or higher, about 3 or higher, about 3.5 or higher, about 4 or higher, about 4.5 or higher, or about 5 or higher).

When the absolute value of the value of statistical significance is below the predetermined threshold, the measured dosage of the test chromosome or portion thereof is not sufficiently above (or below in the case of a negative predetermined threshold) the expected test chromosome dosage that the call of abnormality (e.g., aneuploidy or microdeletion) cannot be made with the desired confidence level. This might occur, for example, when the test chromosome is euploid for the fetal cfDNA, but may also occur when the test chromosome is aneuploid for the cfDNA and the accuracy or precision of the measured test chromosome dosage is not sufficient to distinguish the measured test chromosome dosage from the expected test chromosome dosage. The accuracy or precision may not be sufficient, for example, if the fetal fraction of cfDNA in the test maternal sample is low and the sequencing depth is low.

In some embodiments, a value of likelihood that the fetal cell-free DNA is abnormal (e.g., aneuploid or microdeletion) for the test chromosome (or portion thereof) is determined based on the measured dosage of the test chromosome (or portion thereof), the expected dosage, and the measured fetal fraction. The value of likelihood can be, for example, odds ratio that the test chromosome for the fetal cfDNA is abnormal versus normal. In some embodiments, if the value of likelihood that the test chromosome is abnormal is below a predetermined threshold, then the test chromosome (or portion thereof) is called as normal. If, however, the value of likelihood is above the predetermined threshold, the test chromosome (or portion thereof) is not called as normal (and may be called as abnormal if the absolute value of the value of statistical significance is above the predetermined threshold). If the test chromosome (or portion thereof) is not called as normal and is not called as abnormal (for example, if the value of statistical significance is below a predetermined threshold and the value of likelihood of abnormality is above a predetermined threshold), it is generally because the measured test chromosome dosage is not sufficiently resolved from the expected test chromosome dosage. In some embodiments, if the test chromosome is not called as abnormal or normal from the initially determined value of likelihood and/or value of statistical significance, the test chromosome dosage is re-measured by analyzing a greater number of quantifiable assay products, such as sequencing reads. In some embodiments, the predetermined threshold that that the odds ratio that the test chromosome for the fetal cfDNA is abnormal versus normal is about 0.05 or higher, about 0.1 or higher, about 0.15 or higher, about 0.20 or higher, about 0.25 or higher, or about 0.3 or higher.

As an example, the determination of a call for the test chromosome or portion thereof as normal (e.g., euploid or no microdeletion) or abnormal (e.g., aneuploid or with a microdeletion) can summarized in Table 2, wherein the arrow indicates whether the indicated value is above or below the predetermined threshold.

TABLE 2

Abnormal Test Chromosome (or Portion) Calling Logic

| Value of Statistical Significance | Value of Likelihood of Abnormality | Call |
| --- | --- | --- |
| ↑ | n.d. | Abnormal |
| ↓ | ↑ | No call |
| ↓ | ↓ | Normal |

"n.d." indicates that the value of likelihood of aneuploidy need not be determined if the value of statistical significance is above the predetermined threshold.

If no call is made (for example, because the value of statistical significance is too low and the value of likelihood of an abnormality is too high), the test maternal sample can be reflexed (that is, the test chromosome is re-measured) with a greater assay depth. Optionally, if the test maternal sample is reflexed, the fetal fraction can also be re-measured with a greater assay depth.

In some embodiments, the test chromosome (or portion thereof) of the fetal cfDNA is called as abnormal (e.g., aneuploid or having a microdeletion) if the value of statistical significance (e.g., Z-score) is above a predetermined threshold. In some embodiments, the test chromosome (or portion thereof) of the fetal cfDNA is called as abnormal (e.g., aneuploid or having a microdeletion) only if the value of statistical significance (e.g., Z-score) is above a predetermined threshold. In some embodiments, the test chromosome of the fetal cfDNA is called as abnormal (e.g., aneuploid or having a microdeletion) only if the fetal fraction is above a predetermined threshold.

In some embodiments, the test chromosome (or portion thereof) of the fetal cfDNA is called as normal (e.g., euploid or no microdeletion) if the value of likelihood of an abnormality is below a predetermined threshold. In some embodiments, the test chromosome (or portion thereof) of the fetal cfDNA is called as normal (e.g., euploid or no microdeletion) only if the value of likelihood of an abnormality is below a predetermined threshold. In some embodiments, the test chromosome (or portion thereof) of the fetal cfDNA is called as normal (e.g., euploid or no microdeletion) if the value of likelihood of an abnormality is below a predetermined threshold and the value of statistical significance is below a predetermined threshold. In some embodiments, the test chromosome (or portion thereof) of the fetal cfDNA is called as normal (e.g., euploid or no microdeletion) only if the value of likelihood of an abnormality is below a predetermined threshold and the value of statistical significance is below a predetermined threshold. In some embodiments, the test chromosome (or portion thereof) of the fetal cfDNA is called as normal (e.g., euploid or no microdeletion) only if the fetal fraction is above a predetermined threshold.

In some embodiments, the dosage of the test chromosome (or portion thereof) is re-measured if the value of likelihood of an abnormality is above a predetermined threshold and the value of statistical significance (such as a Z-score) is below a predetermined threshold. In some embodiments, the dosage of the test chromosome (or portion thereof) is re-measured only if the value of likelihood of an abnormality is above a predetermined threshold and the value of statistical significance (such as a Z-score) is below a predetermined threshold.

In some embodiments, the dosage of the test chromosome (or portion thereof) is re-measured using a subsequent assay that generates a subsequent plurality of quantifiable products (such as sequencing reads or PCR products) from the test chromosome. In some embodiments, the fetal fraction is also re-measured using the subsequent plurality of quantifiable products. The subsequent plurality of quantifiable products can be separately analyzed, or the quantifiable products can be analyzed in combination with the plurality of quantifiable products formed from the initial assay. The number of quantifiable products in the subsequent plurality (or the number of quantifiable products in the combination of the subsequent plurality and the initial plurality) is preferably greater than the number of quantifiable products in the initial assay. By generating a large number of quantifiable products, the accuracy and/or precision of the measured chromosome dosage can be enhanced. A subsequent value of likelihood that the fetal cell-free DNA is aneuploid for the chromosome and/or a subsequent value of statistical significance can then be determined based on the re-measured chromosome dosage.

When the dosage of the test chromosome or portion thereof is re-measured, for example by using an assay that generates a subsequent plurality of quantifiable products, wherein the number of quantifiable products used to determine the re-measured dosage is greater than the number of quantifiable products used to determine an initially measured dosage, the expected chromosome dosage is adjusted to account for the increase in the number of quantifiable products. In some embodiments, the expected chromosome dosage is re-determined using the methods described herein, but with the greater number of quantifiable products.

By way of example, the number of quantifiable products (such as sequencing reads) in the initial assay used to determine the initial test chromosome dosage (and/or fetal fraction) can be about 6 million reads or more (such as about 7 million reads or more, about 8 million reads or more, about 9 million reads or more, about 10 million reads or more, about 11 million reads or more, about 12 million reads or more, about 13 million reads or more, about 14 million reads or more, about 15 million reads or more, about 16 million reads or more, or about 17 million reads or more). The number of reads is based on genome-wide sequencing, and the number of reads can be reduced by the proportion of the genome that is actually sequenced. The number of quantifiable products used to determine the subsequent dosage of the test chromosome or portion thereof (which can be, for example, the combination of the quantifiable products from the initial assay and the subsequent assay, or from the subsequent assay alone) can be, for example, about 18 million reads or more (such as about 20 million reads or more, about 25 million reads or more, about 30 million reads or more, about 35 million reads or more, about 40 million reads or more, about 45 million reads or more, about 50 million reads or more, about 60 million reads or more, about 70 million reads or more, about 80 million reads or more, about 90 million reads or more, or about 100 million reads or more). As the cost of an assay generally increases with the number of reads, it is generally preferable to minimize the number of reads necessary in an initial or subsequent assay. By performing the initial assay for all test maternal samples and only performing the subsequent assay for those test maternal samples for which no call (either aneuploid or euploid) can be made, excess and unnecessary assays are minimized.

Calls of normal or abnormal test chromosome can be made using the subsequently determined value of statistical significance (e.g., Z-score) and/or value of likelihood of abnormality in a similar manner as for the initially determined value of statistical significance and/or value of likelihood of abnormality, except the determination is based on the re-measured dosage. Because the re-measured dosage of the test chromosome or portion thereof is determined using a larger number of quantifiable products, the accuracy of the re-measured dosage and the expected dosage is greater, and the magnitude of the expected variance is less.

In some instances, the absolute value of the subsequently determined value of statistical significance (e.g., Z-score) is below the predetermined threshold and the subsequent value of likelihood of an abnormality is above the predetermined threshold. Optionally, a no-call can be made for those samples. Alternatively, the test maternal sample can be again reflexed (that is, the dosage of the test chromosome (or a portion thereof) can be again re-measured and value of statistical significance and/or value of likelihood of an abnormality re-determined). In some embodiments, test maternal samples are reflexed one or more times, two or more times, three or more times, or four or more times.

Computing Systems

Figure 2:
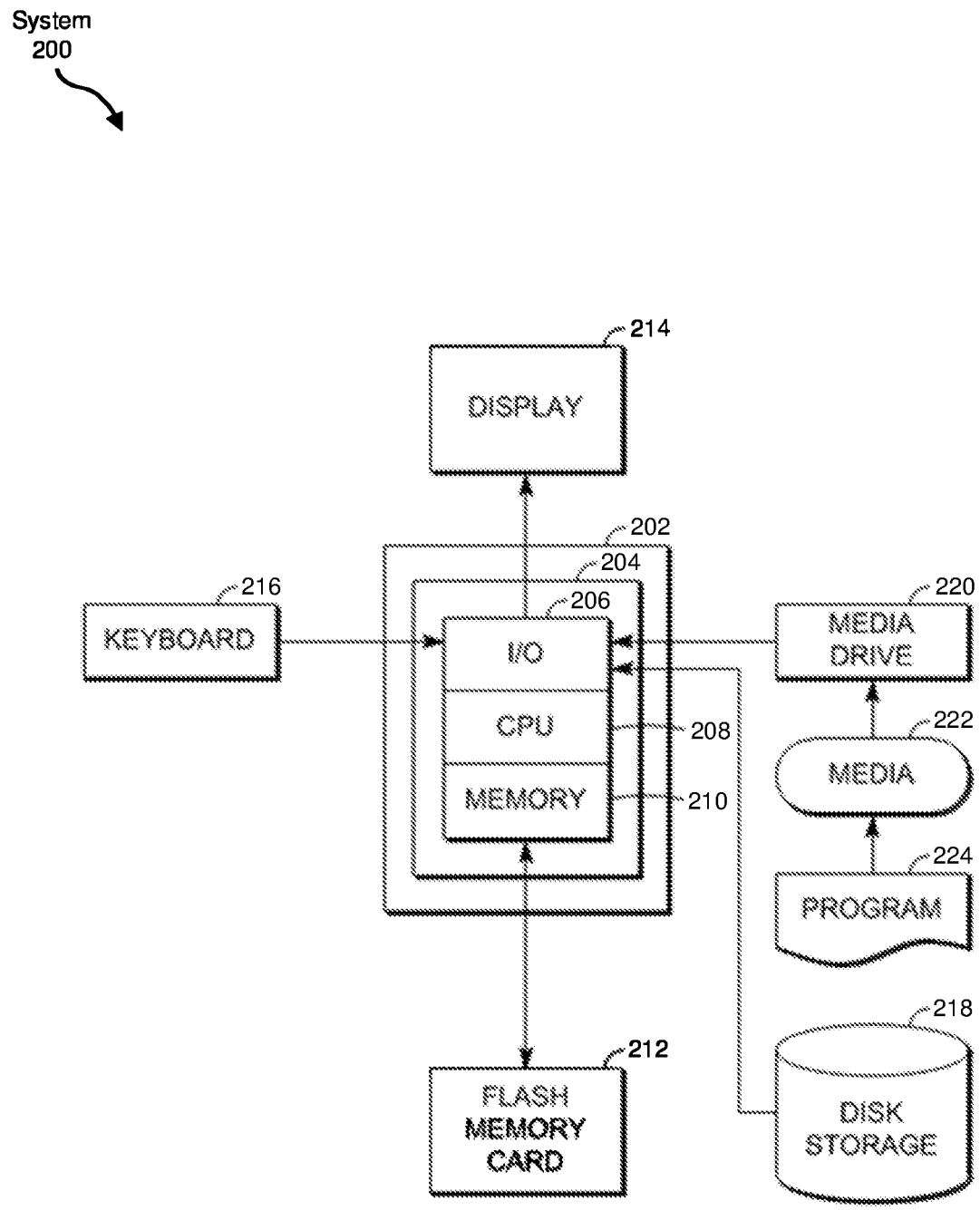
FIG. 2 depicts an exemplary computing system configured to perform processes described herein, including the various exemplary methods for determining a fetal chromosomal abnormality in a test chromosome or a portion thereof by analyzing a test maternal sample.

In some embodiments, the methods described herein are implemented by a program executed on a computer system. FIG. 2 depicts an exemplary computing system 200 configured to perform any one of the above-described processes, including the various exemplary methods for determining a fetal chromosomal abnormality in a test chromosome or a portion thereof by analyzing a test maternal sample. The computing system 200 may include, for example, a processor, memory, storage, and input/output devices (e.g., monitor, keyboard, disk drive, Internet connection, etc.). The computing system 200 may include circuitry or other specialized hardware for carrying out some or all aspects of the processes. For example, in some embodiments, the computing system includes a sequencer (such as a massive parallel sequencer). In some operational settings, computing system 200 may be configured as a system that includes one or more units, each of which is configured to carry out some aspects of the processes either in software, hardware, or some combination thereof.

FIG. 2 depicts computing system 200 with a number of components that may be used to perform the above-described processes. The main system 202 includes a motherboard 204 having an input/output ("I/O") section 206, one or more central processing units ("CPU") 208, and a memory section 210, which may have a flash memory card 212 related to it. The I/O section 206 is connected to a display 214, a keyboard 216, a disk storage unit 218, and a media drive unit 220. The media drive unit 220 can read/write a computer-readable medium 222, which can contain programs 224 and/or data.

At least some values based on the results of the above-described processes can be saved for subsequent use. Additionally, a non-transitory computer-readable medium can be used to store (e.g., tangibly embody) one or more computer programs for performing any one of the above-described processes by means of a computer. The computer program may be written, for example, in a general-purpose programming language (e.g., Pascal, C, C++, Java, Python, JSON, etc.) or some specialized application-specific language.

Exemplary Methods

Figure 3:
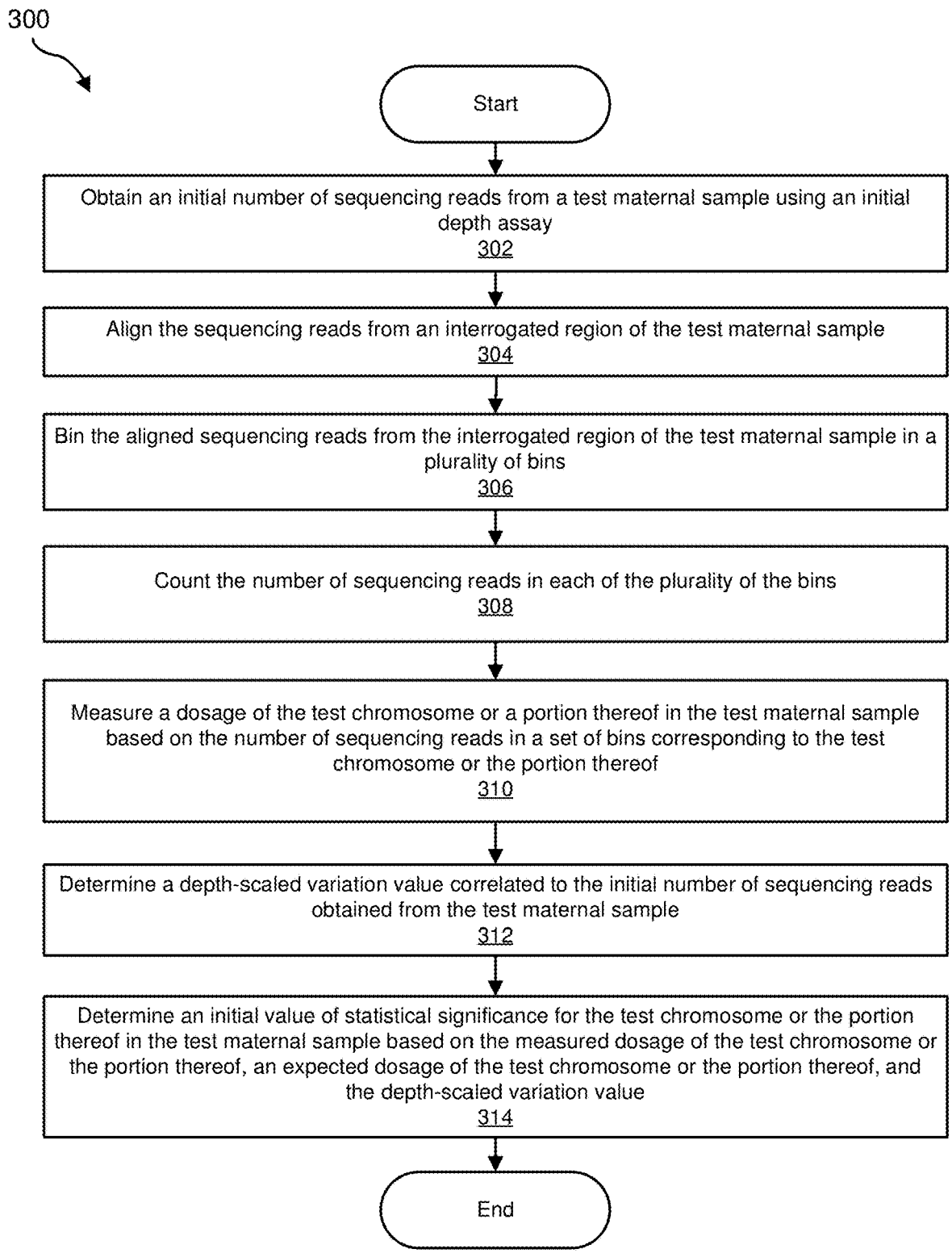
FIG. 3 is a flow diagram of an exemplary method for determining a chromosomal abnormality in a test chromosome of a fetus by analyzing a test maternal sample.

FIG. 3 is a flow diagram of an exemplary method 300 for determining a chromosomal abnormality in a test chromosome of a fetus by analyzing a test maternal sample of a woman carrying said fetus, wherein the test maternal sample includes fetal cell-free DNA and maternal cell-free DNA. Some of the steps shown in FIG. 3 may be performed by any suitable computer-executable code and/or computing system, including system 200 in FIG. 2. In one example, some of the steps shown in FIG. 3 may represent an algorithm whose structure includes and/or is represented by multiple sub-steps, examples of which will be provided in greater detail below.

As illustrated in FIG. 3, at step 302, an initial number of sequencing reads may be obtained from the test maternal sample using an initial depth assay. At step 304, the sequencing reads from an interrogated region of the test maternal sample may be aligned. At step 306, the aligned sequencing reads from the interrogated region of the test maternal sample may be binned in a plurality of bins. At step 308, the number of sequencing reads in each of the plurality of the bins may be counted. At step 310, the dosage of the test chromosome or a portion thereof in the test maternal sample may be measured based on the number of sequencing reads in a set of bins corresponding to the test chromosome or the portion thereof. At step 312, a depth-scaled variation value correlated to the initial number of sequencing reads obtained from the test maternal sample may be determined. At step 314, an initial value of statistical significance for the test chromosome or the portion thereof in the test maternal sample may be determined based on the measured dosage of the test chromosome or the portion thereof, an expected dosage of the test chromosome or the portion thereof, and the depth-scaled variation value.

In some embodiments, determining the depth-scaled variation value may include calculating the depth-scaled variation value based on a plurality of reference samples assayed at a sequencing depth or range of sequencing depths corresponding to the initial number of sequencing reads obtained from the test maternal sample. In some embodiments, the depth-scaled variation value may be determined based on variation in counts of binned sequencing reads for the test chromosome or the portion thereof of the plurality of reference maternal samples.

In some embodiments, the method may include calling the test chromosome or the portion thereof in the fetal cell-free DNA of the test maternal sample to be abnormal if the absolute value of the initial value of statistical significance is above a predetermined threshold. In some embodiments, the method may include re-measuring the dosage of the test chromosome or the portion thereof in the test maternal sample using a higher depth assay if the absolute value of the scaled value of statistical significance is below a predetermined threshold, and determining a subsequent value of statistical significance for the test chromosome or the portion thereof in the test maternal sample based on the re-measured dosage.

In some embodiments, the method may include measuring a fetal fraction of cell-free DNA in the test maternal sample based on counts of binned sequencing reads from the interrogated region of the test maternal sample, and determining an initial value of likelihood that the test chromosome or the portion thereof in the fetal cell-free DNA of the test maternal sample is abnormal based on the initial value of statistical significance and the measured fetal fraction. In some embodiments, the value of likelihood may be an odds ratio. In some embodiments, the method may include calling the test chromosome or the portion thereof in the fetal cell-free DNA of the test maternal sample to be normal if the scaled value of likelihood is below a predetermined threshold. In some embodiments, the method may include re-measuring the dosage of the test chromosome or the portion thereof in the test maternal sample using a higher depth assay if the scaled value of likelihood is above a predetermined threshold and the absolute value of the scaled value of statistical significance is below a predetermined threshold, and determining a subsequent value of statistical significance for the test chromosome or the portion thereof in the test maternal sample based on the re-measured dosage.

In some embodiments, the depth-scaled variation value may be a standard deviation, an interquartile range, or a variance. In some embodiments, the value of statistical significance may be a Z-score, a p-value, or a probability. In some embodiments, the chromosomal abnormality may be a microdeletion, and the test chromosome or the portion thereof is a putative microdeletion. In some embodiments, the chromosomal abnormality may be aneuploidy, and the test chromosome or the portion thereof may be at least one complete chromosome. In some embodiments, the dosages of a plurality of test chromosomes or portions thereof may be simultaneously measured. In some embodiments, the dosage of the test chromosome or the portion thereof in the test maternal sample may be measured by determining an average number of sequencing reads per bin and a variation of the number of sequencing reads per bin.

In some embodiments, the method may include selecting a plurality of cohort reference maternal samples based on at least one similarity between each of the plurality of cohort reference maternal samples and the test maternal sample. In some embodiments, the at least one similarity between each of the plurality of cohort reference maternal samples and the test maternal sample may include at least one of a similarity in guanine-cytosine (GC) biases, binned sequencing depths, and normalized chromosomal medians between the set of reference maternal samples and the test maternal sample. In some embodiments, the at least one similarity between each of the plurality of cohort reference maternal samples and the test maternal sample may be determined by identifying one or more clusters that each include the test maternal sample and at least one of the plurality of cohort reference maternal samples. In some embodiments, the one or more clusters may be identified based on characteristic values of each of the plurality of cohort reference maternal samples and the test maternal sample. In some embodiments, the one or more clusters may be generated by k-means clustering of a plurality of reference maternal samples that includes the plurality of cohort reference maternal samples. In some embodiments, the at least one similarity between each of the plurality of cohort reference maternal samples and the test maternal sample may be determined by identifying one or more clusters based on at least one characteristic value of the each of each the plurality of cohort reference maternal samples, determining a centroid of each of the one or more clusters, and determining that the at least one characteristic value of the test maternal sample is within a threshold distance of the centroid of each of the one or more clusters. In some embodiments, the initial value of statistical significance for the test chromosome or the portion thereof may be determined by calculating an expected variation value that is based on the depth-scaled variation value and a cohort-based variation value that is determined based on variation in counts of binned sequencing reads for the test chromosome or the portion thereof of the plurality of cohort reference maternal samples.

In some embodiments, the method may include determining the expected dosage of the test chromosome or a portion thereof in the test maternal sample using a robust regression model that is trained based on measured dosages of a plurality of chromosomes or portions thereof of a plurality of reference maternal samples. In some embodiments, the trained regression model may be a maximum likelihood type regression model. In some embodiments, the trained regression model may be a Huber robust regression model. In some embodiments, the interrogated region may include at least a portion of a chromosome other than the test chromosome or the portion thereof. In some embodiments, the interrogated region may include at least a whole chromosome other than the test chromosome. In some embodiments, the robust regression model may be trained by, for each of the plurality of reference maternal samples: aligning sequencing reads from the interrogated region in the plurality of chromosomes or portions thereof, binning the aligned sequencing reads from the interrogated region in a plurality of bins, and counting the number of sequencing reads in each bin, and determining one or more model coefficients based on the number of sequencing reads in each bin for each of the plurality of reference maternal samples. In some embodiments, the trained regression model may utilize a weight function that varies based on at least one of an average number of sequencing reads per bin and a variation of the number of sequencing reads per bin for the plurality of bins. In some embodiments, the method may include normalizing the number of sequencing reads in each bin prior to counting the number of sequencing reads in each bin.

In some embodiments, the method may include determining a predicted value of statistical significance for the test chromosome or the portion of the test maternal sample thereof based on an additional depth-scaled variation value correlated to a higher number of sequencing reads that is higher than the initial number of sequencing reads obtained from the test maternal sample. In some embodiments, determining the additional depth-scaled variation value may include calculating the depth-scaled variation value based on a plurality of reference samples assayed at a higher sequencing depth or range of sequencing depths corresponding to the higher number of sequencing reads.

Figure 4:
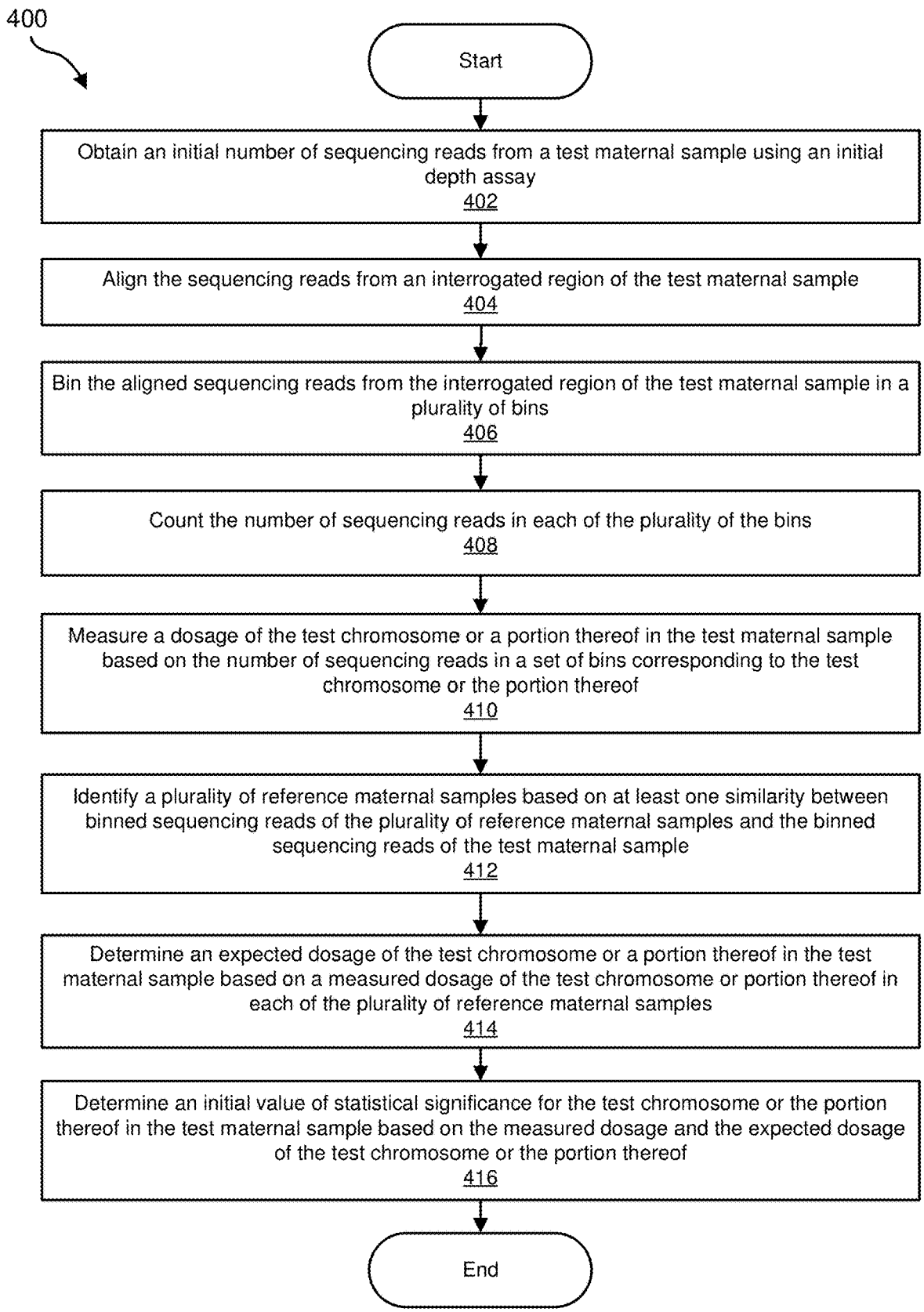
FIG. 4 is a flow diagram of an exemplary method for determining a chromosomal abnormality in a test chromosome of a fetus by analyzing a test maternal sample.

FIG. 4 is a flow diagram of an exemplary method 400 for determining a chromosomal abnormality in a test chromosome of a fetus by analyzing a test maternal sample of a woman carrying said fetus, wherein the test maternal sample includes fetal cell-free DNA and maternal cell-free DNA. Some of the steps shown in FIG. 4 may be performed by any suitable computer-executable code and/or computing system, including system 200 in FIG. 2. In one example, some of the steps shown in FIG. 4 may represent an algorithm whose structure includes and/or is represented by multiple sub-steps, examples of which will be provided in greater detail below.

As illustrated in FIG. 4, at step 402, an initial number of sequencing reads may be obtained from the test maternal sample using an initial depth assay. At step 404, the sequencing reads from an interrogated region of the test maternal sample may be aligned. At step 406, the aligned sequencing reads from the interrogated region of the test maternal sample may be binned in a plurality of bins. At step 408, the number of sequencing reads in each of the plurality of the bins may be counted. At step 410, the dosage of the test chromosome or a portion thereof in the test maternal sample may be measured based on the number of sequencing reads in a set of bins corresponding to the test chromosome or the portion thereof. At step 412, a plurality of reference maternal samples may be identified based on at least one similarity between binned sequencing reads of the plurality of reference maternal samples and the binned sequencing reads of the test maternal sample. At step 414, an expected dosage of the test chromosome or a portion thereof in the test maternal sample may be determined based on a measured dosage of the test chromosome or portion thereof in each of the plurality of reference maternal samples. At step 416, an initial value of statistical significance for the test chromosome or the portion thereof in the test maternal sample may be determined based on the measured dosage and the expected dosage of the test chromosome or the portion thereof.

Figure 5:
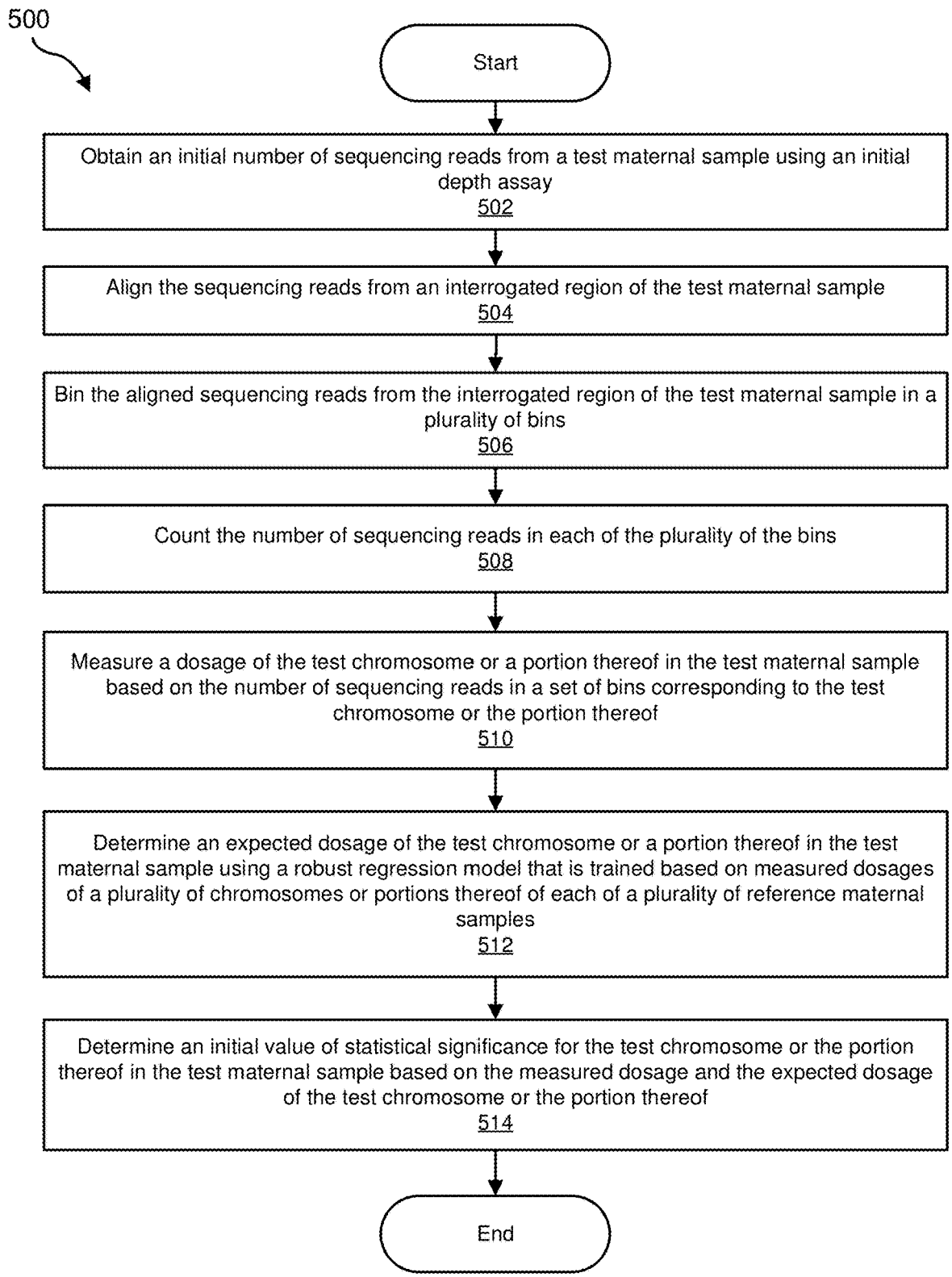
FIG. 5 is a flow diagram of an exemplary method for determining a chromosomal abnormality in a test chromosome of a fetus by analyzing a test maternal sample.

FIG. 5 is a flow diagram of an exemplary method 500 for determining a chromosomal abnormality in a test chromosome of a fetus by analyzing a test maternal sample of a woman carrying said fetus, wherein the test maternal sample includes fetal cell-free DNA and maternal cell-free DNA. Some of the steps shown in FIG. 5 may be performed by any suitable computer-executable code and/or computing system, including system 200 in FIG. 2. In one example, some of the steps shown in FIG. 5 may represent an algorithm whose structure includes and/or is represented by multiple sub-steps, examples of which will be provided in greater detail below.

As illustrated in FIG. 5, at step 502, an initial number of sequencing reads may be obtained from the test maternal sample using an initial depth assay. At step 504, the sequencing reads from an interrogated region of the test maternal sample may be aligned. At step 506, the aligned sequencing reads from the interrogated region of the test maternal sample may be binned in a plurality of bins. At step 508, the number of sequencing reads in each of the plurality of the bins may be counted. At step 510, the dosage of the test chromosome or a portion thereof in the test maternal sample may be measured based on the number of sequencing reads in a set of bins corresponding to the test chromosome or the portion thereof. At step 512, an expected dosage of the test chromosome or a portion thereof in the test maternal sample may be determined using a robust regression model that is trained based on measured dosages of a plurality of chromosomes or portions thereof of each of a plurality of reference maternal samples. At step 514, an initial value of statistical significance for the test chromosome or the portion thereof in the test maternal sample may be determined based on the measured dosage and the expected dosage of the test chromosome or the portion thereof.

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art, each of the individual variations described and illustrated herein has discrete components and features that may be readily separated from or combined with the features of any of the other several embodiments without departing from the scope or spirit of the various embodiments. All such modifications are intended to be within the scope of claims associated with this disclosure.

The following non-limiting examples further illustrate the methods of the present invention. Those skilled in the art will recognize that several embodiments are possible within the scope and spirit of this invention. While illustrative of the invention, the following examples should not be construed in any way limiting its scope.

EXAMPLES

Example 1: Comparison of Z-Score Calculations

Cell-free DNA of 34,012 test maternal samples taken from pregnant women was sequenced, aligned using a reference genome, and binned in a plurality of bins, and the number of sequencing reads in each bin was counted. Z-scores (i.e., depth-scaled Z-scores) were determined for each of the test maternal samples for chromosomes 13, 18, 21 and X using a depth-scaled calculation for expected variation determined based on both a depth-scaled variation and a cohort-based variation based on reference maternal samples according to the equation:

$$\sigma_{exp}^2 = \sigma_c^2 + \frac{\sigma_d^2}{d}$$

where $\sigma_{exp}$ is the variation for the expected dosage distribution for the test chromosome of the test maternal sample, $\sigma_c$ is a cohort-based variation for a plurality of cohort reference maternal samples selected for the test maternal sample through based on k-means clustering, $\sigma_d$ is a depth-scaled variation for a broader population of reference maternal samples assayed at a sequencing depth corresponding to the test sample, and d is the sequencing depth of the test maternal sample. A maximum likelihood parameter estimation model was used to determine values for each of $\sigma_c^2$ and $\sigma_d^2$ according to:

$$\sigma_c^2 = \frac{1}{N} \sum_{i \in cohort} (x_i - \mu_i)^2 \frac{1 - d_i \langle d_i^{-1} \rangle}{1 - \langle d_i \rangle \langle d_i^{-1} \rangle}$$

$$\sigma_d^2 = \frac{1}{N} \sum_i (x_i - \mu_i)^2 \frac{d_i - \langle d_i \rangle}{1 - \langle d_i \rangle \langle d_i^{-1} \rangle}$$

where $x_i$ is the mean or median for the measured dosage distribution of reference maternal sample i of the plurality of reference maternal samples, $\mu_i$ is the mean or median for the expected dosage distribution of reference maternal sample i, and $d_i$ is the measured sequencing depth of reference maternal sample i. The depth-scaled Z-scores for each test maternal sample were determined according to:

$$Z = \frac{x_{test} - \mu_{exp}}{\sigma_{exp}}$$

where $x_{test}$ is the mean or median for the measured dosage distribution of the test chromosome and $\mu_{exp}$ is the mean or median for the expected dosage distribution, and $\sigma_{exp}$ is the variation (such as standard deviation or interquartile range) for the expected dosage distribution.

The $\mu_{exp}$ for the test chromosome of each test maternal sample was determined using a Huber robust regression model according to:

$$\mu_i = \sum_{j \neq i} \beta_j x_j$$

where $\mu_i$ is the mean or median for the expected dosage distribution of the test chromosome of a test maternal sample i determined by the regression model, $x_j$ is the bin vector for the test chromosome of reference maternal sample j, and $\beta_j$ is a regression coefficient for the test chromosome of reference maternal sample j. The regression coefficient was determined by minimizing the square error with $L_2$ norm regularization with a magnitude parameter $\alpha$ according to:

$$\ell(\vec{\beta}) = \alpha \|\vec{\beta}\|^2 + \sum_{samples} \begin{cases} (x - \mu)^2 & \text{if } \frac{x - \mu}{\sigma} < 3 \\ |x - \mu| & \text{if } \frac{x - \mu}{\sigma} \geq 3 \end{cases}$$

For purposes of comparison, the depth-scaled Z-scores for each of chromosomes 13, 18, 21 and X was plotted against Z-scores (i.e., non-depth-scaled Z-scores) for each of the test maternal samples using a non-depth-scaled calculation for expected variation. The non-depth-scaled calculation did not utilize a depth-scaled variation or a cohort-based variation parameters, nor was the mean for the expected dosage distribution determined using a Huber robust regression model. Rather, the expected variation used for the non-depth-scaled Z-scores for each of the test maternal samples was determined from a plurality of reference samples according to:

$$\sigma_{exp}^2 = \left\langle (\delta d_i)^2 \right\rangle_{chr}$$

where $\delta d_i$ is the difference in measured sequencing depth of the test chromosome of reference sample i from a mean or median sequencing depth for the test chromosome of the plurality of reference samples.

Figure 6A:
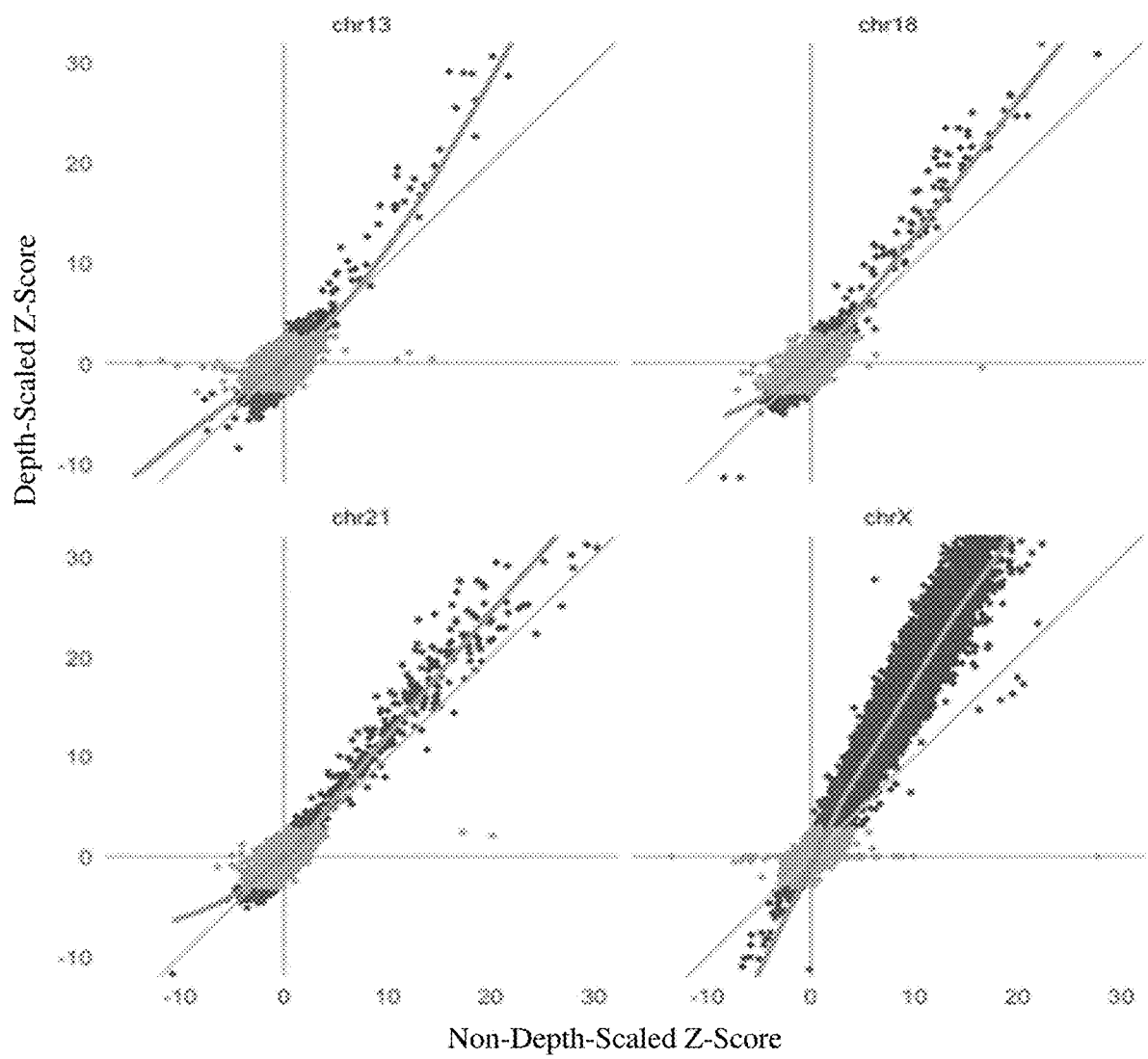
FIG. 6A illustrates Z-score comparison plots for a plurality of samples.

The plotted results are shown in FIG. 6A. A threshold absolute Z-Score of 3 was utilized to identify changes in positive or negative calls for a fetal abnormality between the two types of Z-score calculations. The depth-scaled Z-score calculation demonstrated improvements over the non-depth-scaled Z-score calculation, with a significant number of abnormality calls being changed from negative to positive or from positive to negative. Results showing numbers of changed and unchanged abnormality calls for chromosomes 13, 18, and 21 of the measured test maternal samples are summarized in Table 3.

TABLE 3

Changed and unchanged abnormality calls between non-depth-scaled Z-score calculation and depth-scaled Z-score calculation.

| Chromosome | neg->neg | pos->pos | neg->pos | pos->neg |
|---|---|---|---|---|
| chr13 | 33330 | 127 | 388 | 167 |
| chr18 | 33395 | 168 | 320 | 129 |
| chr21 | 33217 | 350 | 328 | 117 |

Figure 6B:
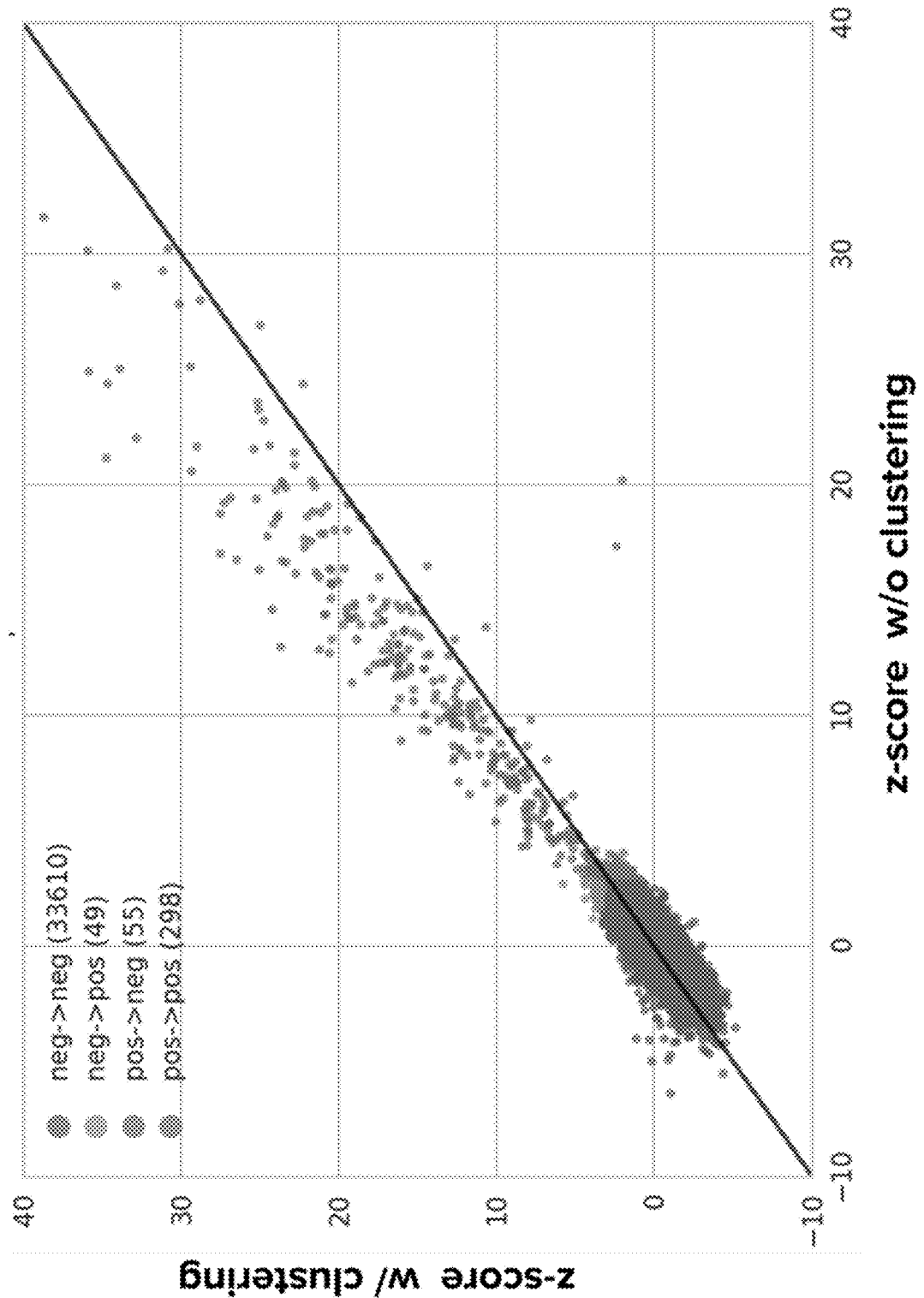
FIG. 6B illustrates a Z-score comparison plot for a plurality of samples.

FIG. 6B shows a comparison of Z-scores for the 34,012 test maternal samples determined using different calculation methodologies. As shown in FIG. 6B, Z-scores calculated for the test maternal samples using K-means clustering and robust regression were plotted against Z-scores calculated without clustering or robust regression for chromosome 21. Using K-means clustering and robust regression, the Z-scores for trisomy 21 positive samples increased without a conspicuous change in Z-scores for euploid samples (similar results were observed for chr13, chr18, and chrX). As Z-scores scale linearly with fetal fraction, a slope greater than one in the scatter plot is consistent with higher sensitivity at low fetal fraction for the algorithm incorporating clustering and robust regression (y-axis).

Example 2: Depth-Scaled Variation Determination

Standard deviations were measured based on sequencing reads obtained from assays of a plurality of test maternal samples taken from pregnant women as described in Example 1. The test maternal samples were assayed at various sequencing depths ranging from about 10,000,000 to 55,000,000 sequencing reads. Standard deviation values (x–μ) were calculated for each of the test maternal samples.

Figure 7A:
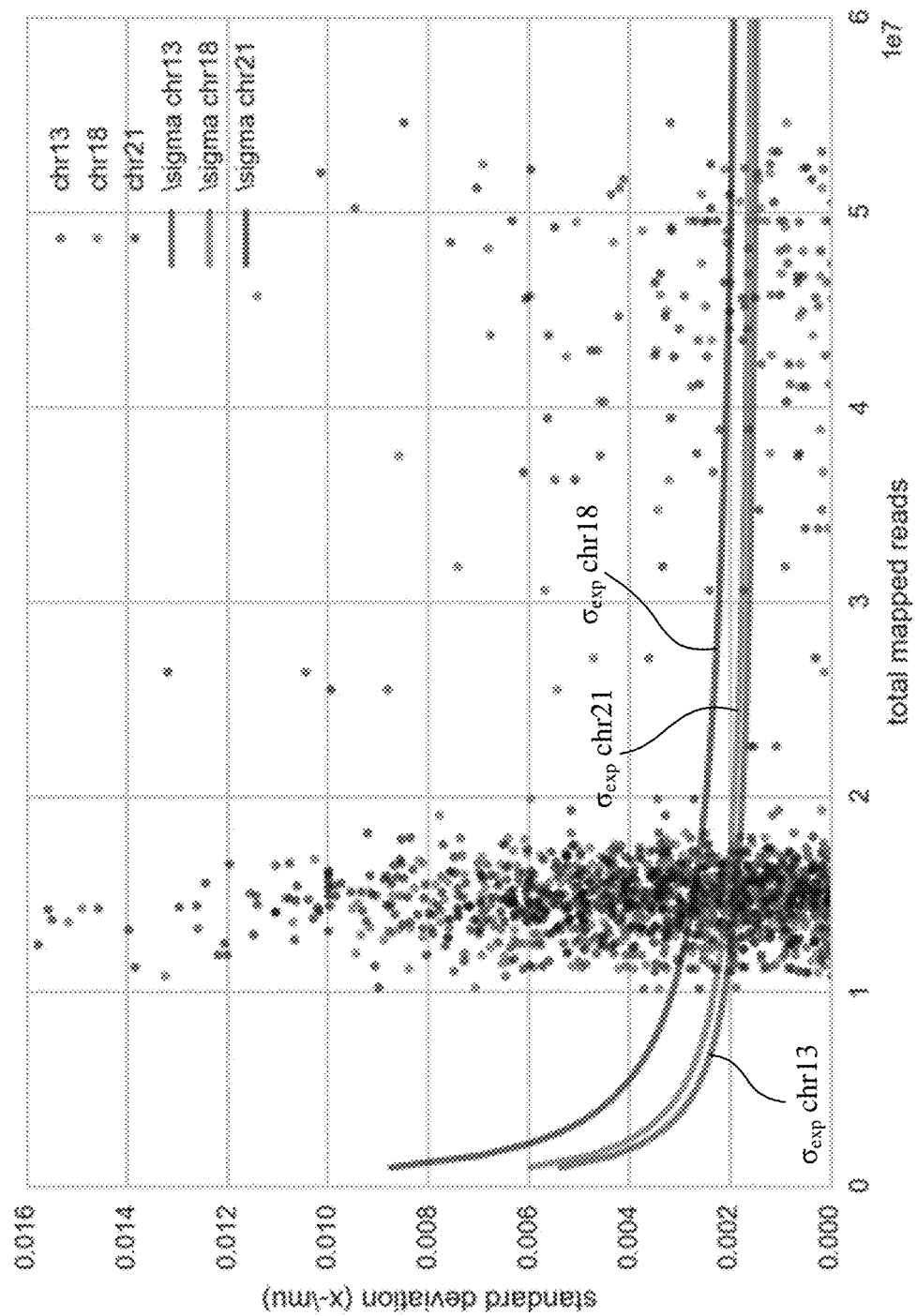
FIG. 7A illustrates standard deviations measured for each of chromosomes 13, 18, and 21 and plotted over a range of sequencing depths.

FIG. 7A shows the plotted standard deviations measured for each of chromosomes 13, 18, and 21 plotted over the range of sequencing depths. Based on the measured standard deviations, $\sigma_{exp}$ values were calculated for each of chromosomes 13, 18, and 21 according to the maximum likelihood parameter estimation model used to for the depth-scale Z-score calculation described in Example 1. As shown in FIG. 7A, $\sigma_{exp}$ for each of chromosomes 13, 18, and 21 decreased with increasing read depth.

Figure 7B:
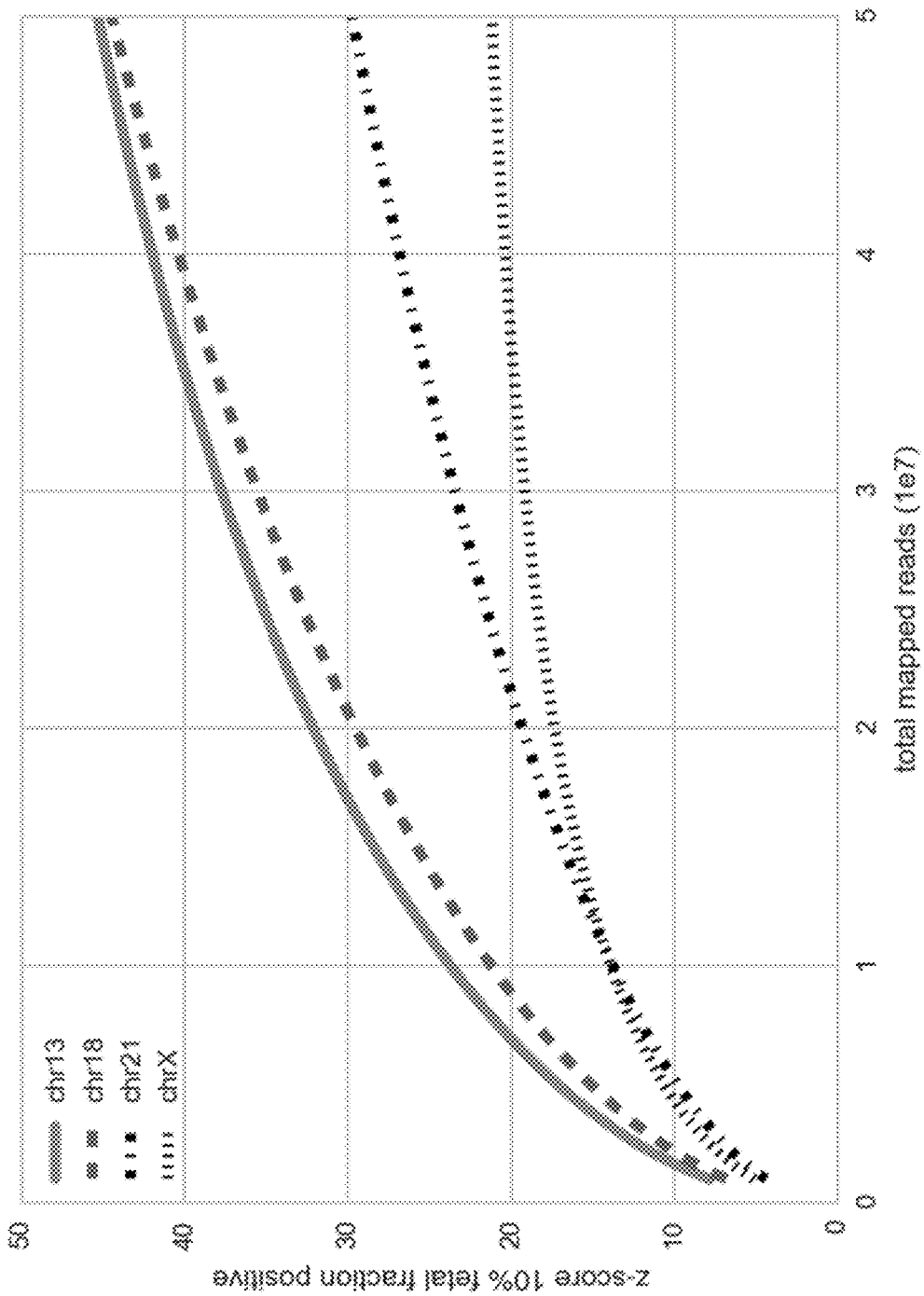
FIG. 7B illustrates exemplary hypothetical Z-scores for a true positive aneuploidy calculated for each of chromosomes 13, 18, 21, and X at 10% fetal fraction plotted as a function of sequencing depth.

FIG. 7B shows exemplary hypothetical Z-scores for a true positive aneuploidy calculated for each of chromosomes 13, 18, 21, and X at 10% fetal fraction plotted over a range of sequencing depths.

Example 3: Z-Score Interquartile Range Comparisons

Figure 8:
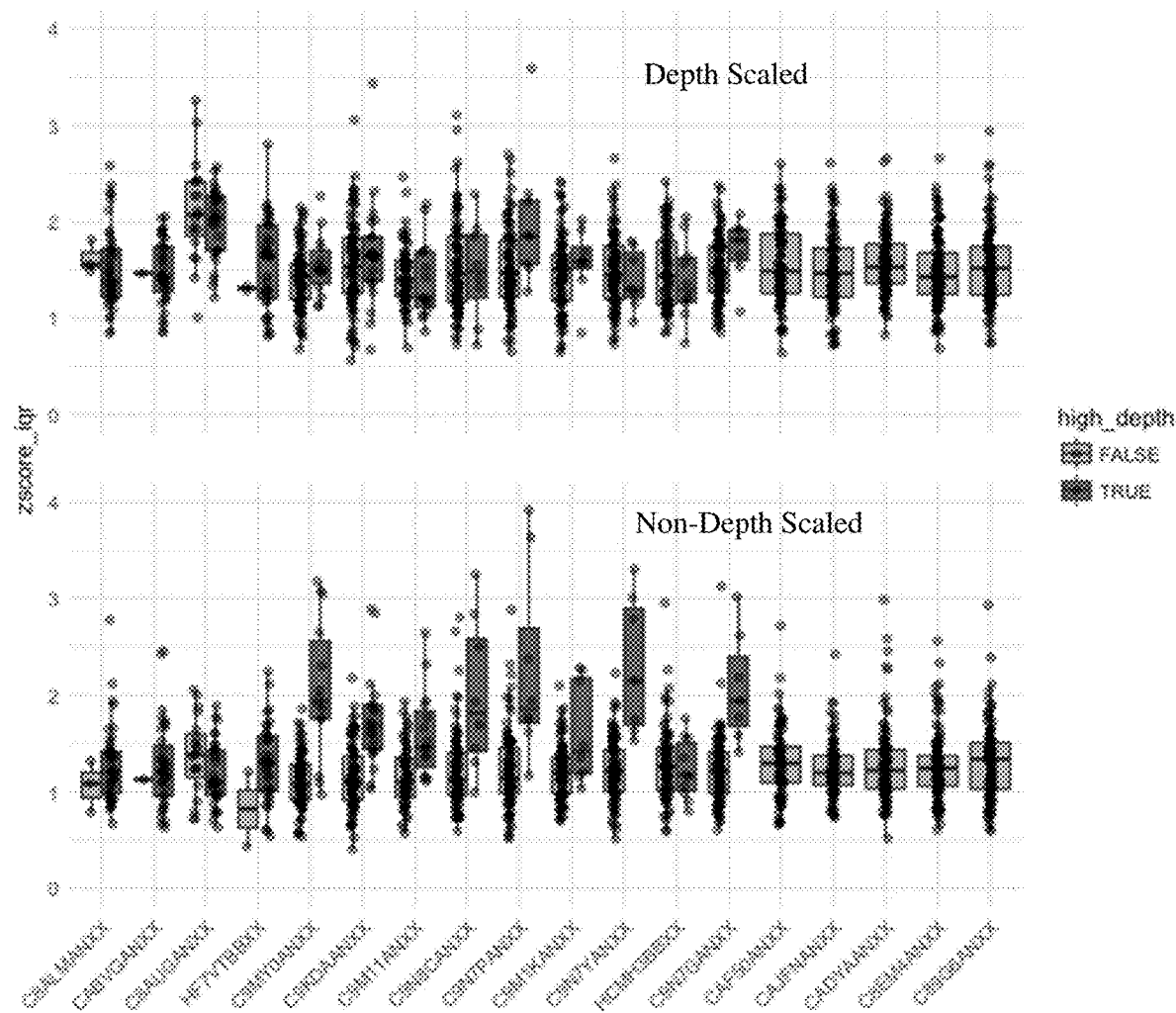
FIG. 8 illustrates interquartile ranges of depth-scaled Z-scores and non-depth-scaled Z-scores plotted for a plurality of mixed flowcells.

Interquartile ranges of Z-scores were determined based on sequencing reads obtained from assays of a plurality of test maternal samples taken from pregnant women as described in Example 1. For comparison, depth-scaled Z-scores and non-depth-scaled Z-scores were determined for each of the samples in the manner described in Example 1. The interquartile ranges of the Z-scores were plotted for a plurality of mixed flowcells as shown in FIG. 8. The interquartile ranges for the depth-scaled Z-scores showed significantly less variation than the interquartile ranges for the non-depth-scaled Z-scores.

Figure 9:
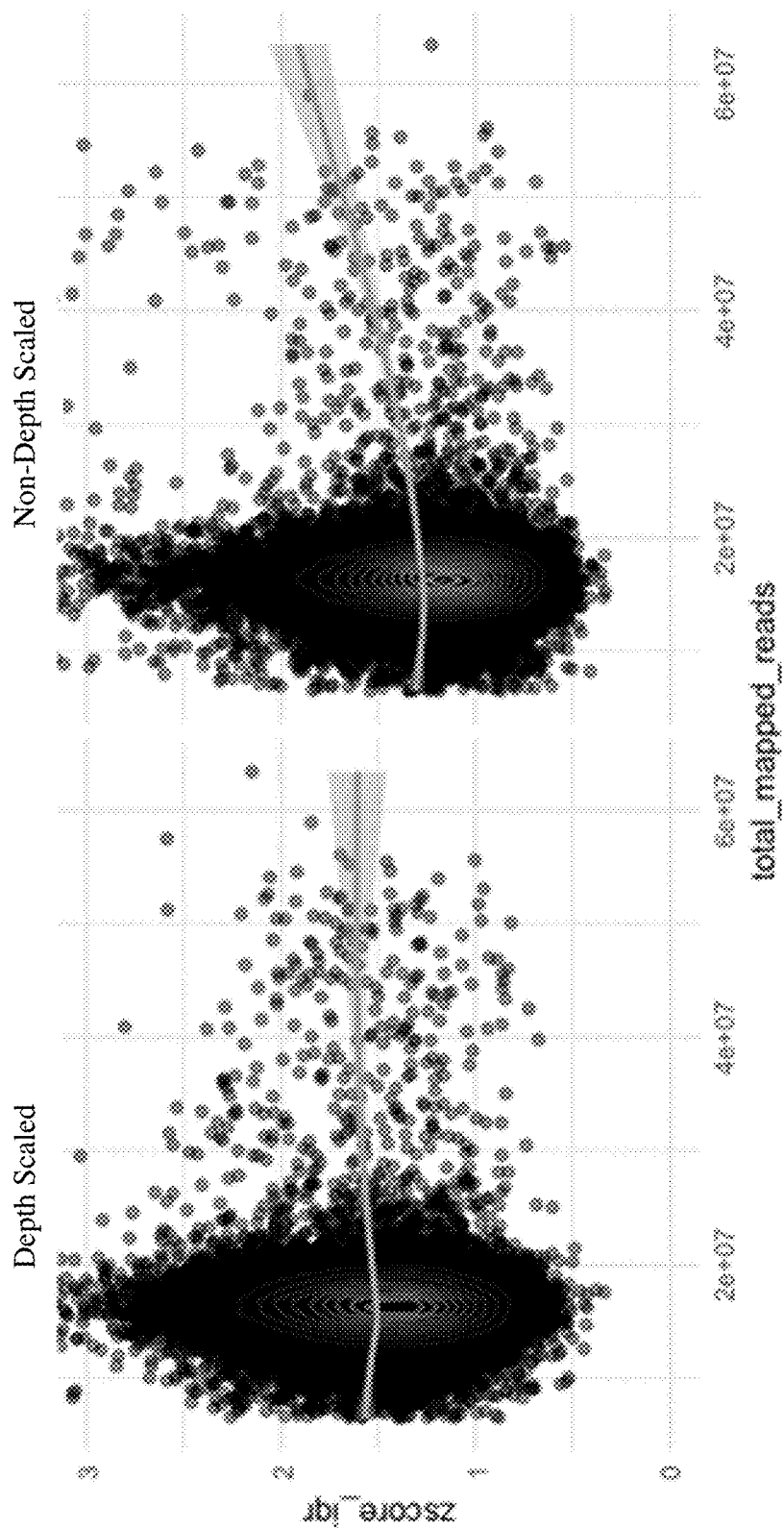
FIG. 9 illustrates interquartile ranges of depth-scaled Z-scores and non-depth-scaled Z-scores plotted for various sequencing read depths.

FIG. 9 shows interquartile ranges of each of the depth-scaled Z-scores and the non-depth-scaled Z-scores for the test maternal samples plotted against sequencing read depths of the test maternal samples. The interquartile ranges for the depth-scaled Z-scores showed less variation than the interquartile ranges for the non-depth-scaled Z-scores over the range of sequencing read depths.

Figure 10A:
FIG. 10A shows a comparison of interquartile values of each of a plurality of non-depth-scaled Z-scores determined for a plurality of test maternal samples.
Figure 10B:
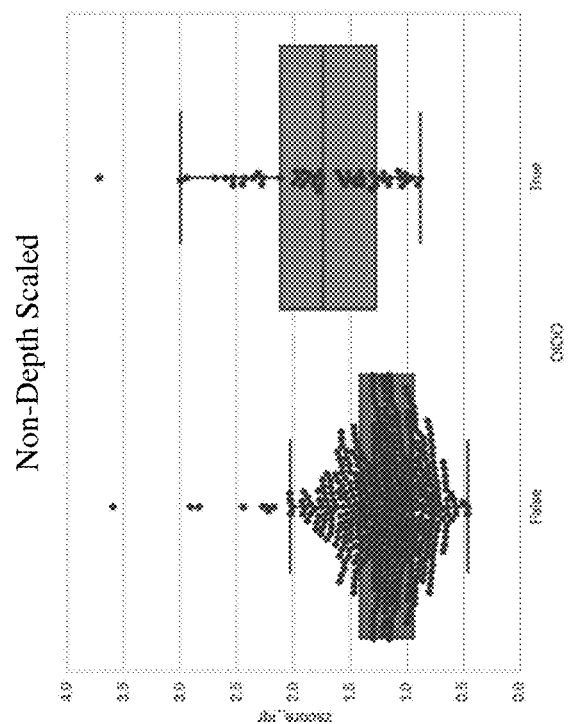
FIG. 10B shows a comparison of interquartile values of each of a plurality of depth-scaled Z-scores determined for a plurality of test maternal samples.

FIGS. 10A and 10B show comparisons of interquartile values of each of a plurality of non-depth-scaled Z-scores and depth-scaled Z-scores respectively determined for a plurality of test maternal samples. The "false" regions correspond to samples not sequenced at a high read depth and the "true" regions correspond to samples sequenced at high read depths. As shown in FIGS. 10A and 10B, the interquartile ranges for the depth-scaled Z-scores for the test maternal samples sequenced at high read depths showed less variation than the interquartile ranges for the corresponding non-depth-scaled Z-scores.

Example 4: Fold Change Interquartile Range Comparison

Figure 11B:
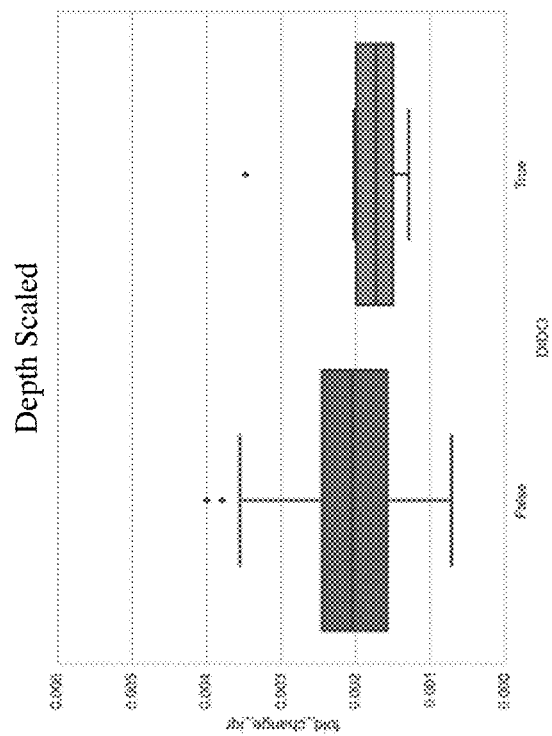
FIG. 11B shows a comparison of interquartile ranges of fold change values determined for each of a plurality of depth-scaled Z-scores determined for a plurality of test maternal samples.
Figure 11A:
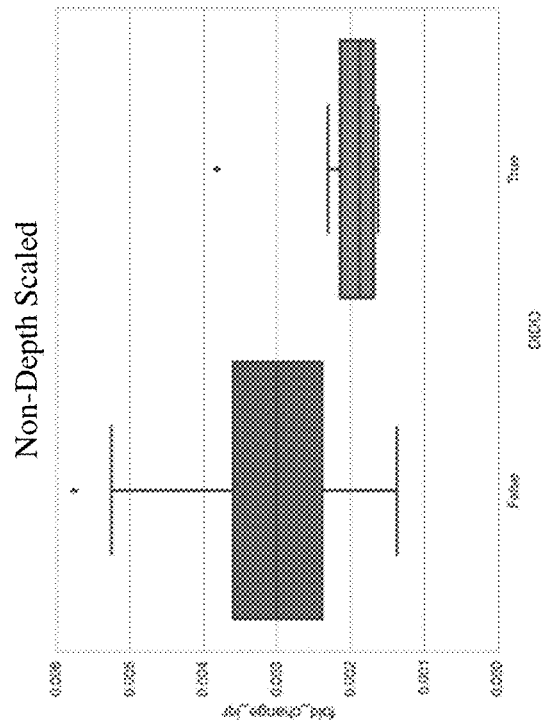
FIG. 11A shows a comparison of interquartile ranges of fold change values determined for each of a plurality of non-depth-scaled Z-scores determined for a plurality of test maternal samples.
Figure 12A:
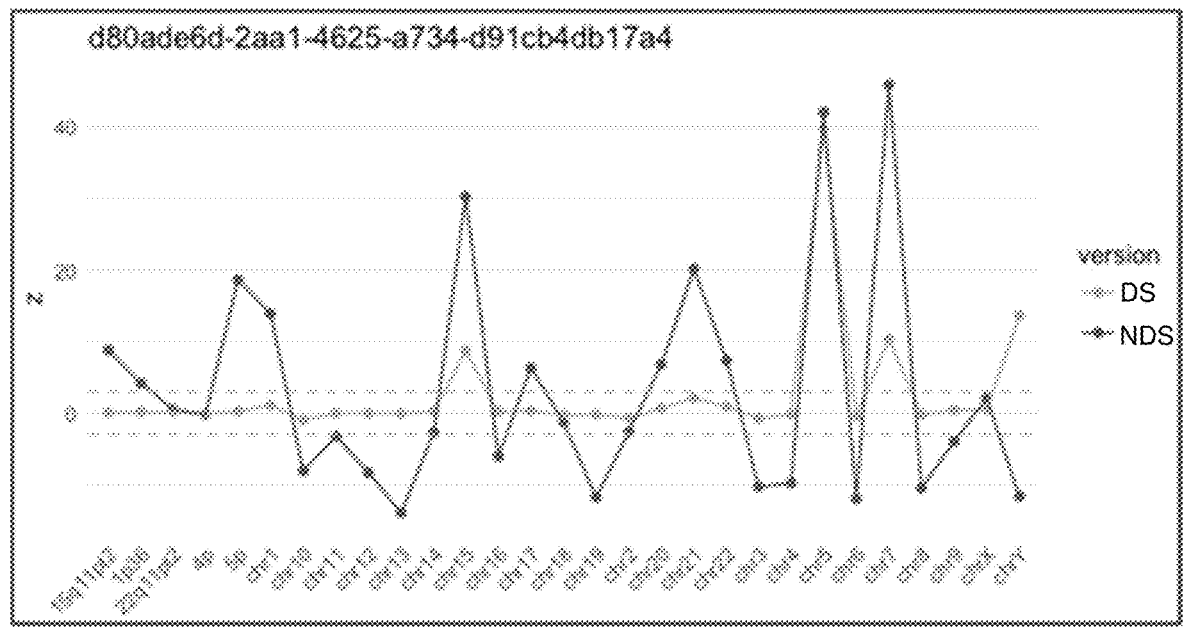
FIG. 12A shows depth-scaled Z-scores and non-depth-scaled Z-scores determined for chromosomes of an individual test maternal sample.
Figure 12B:
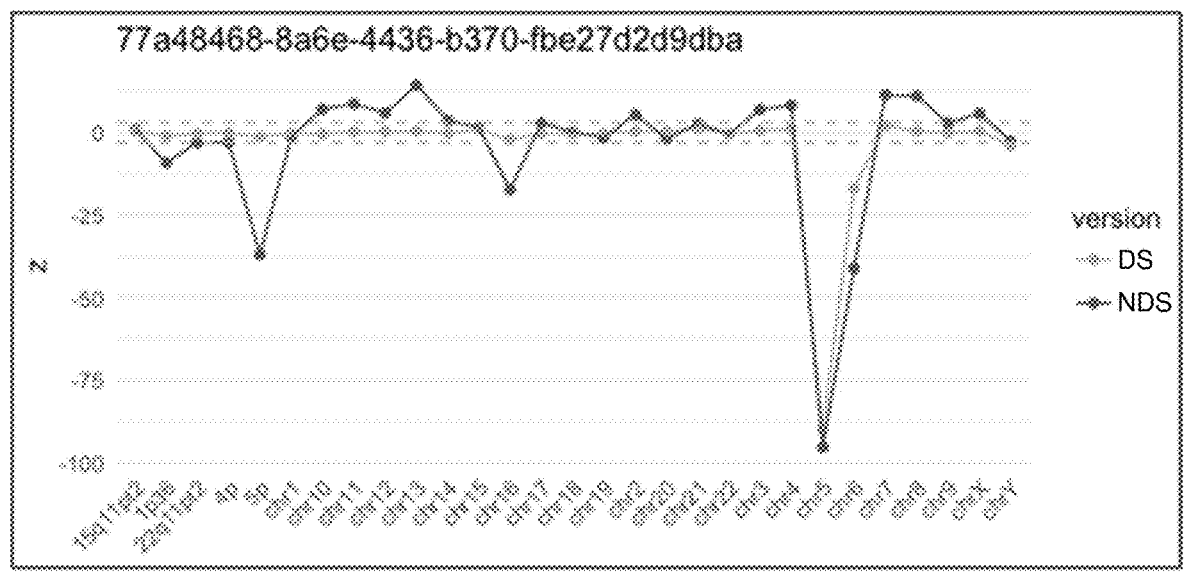
FIG. 12B shows depth-scaled Z-scores and non-depth-scaled Z-scores determined for chromosomes of an individual test maternal sample.
Figure 12C:
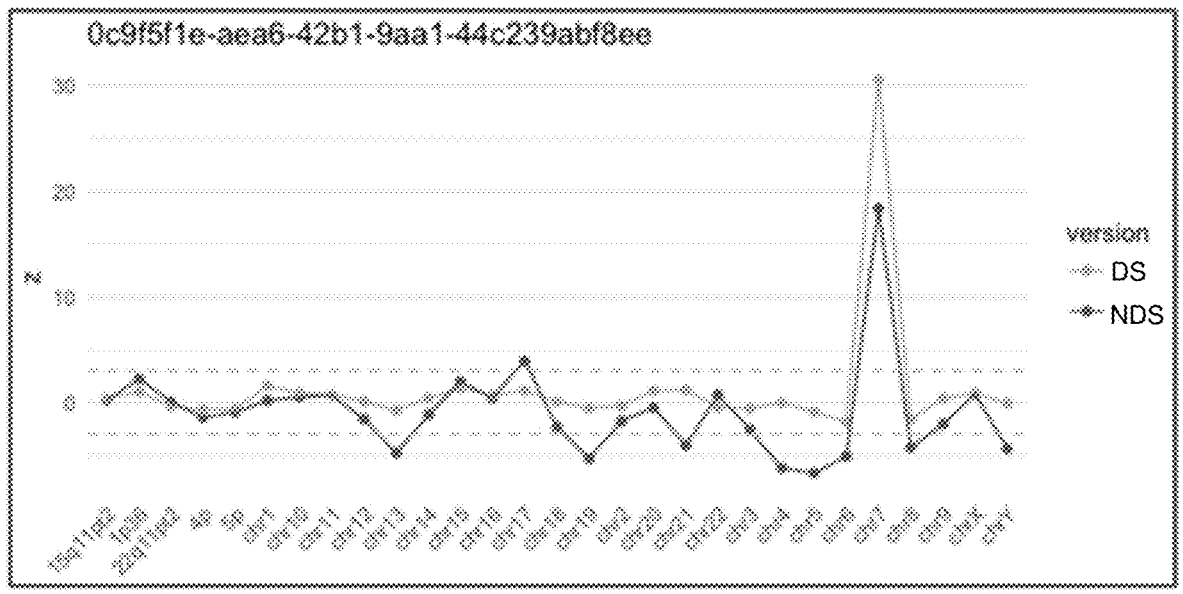
FIG. 12C shows depth-scaled Z-scores and non-depth-scaled Z-scores determined for chromosomes of an individual test maternal sample.
Figure 12D:
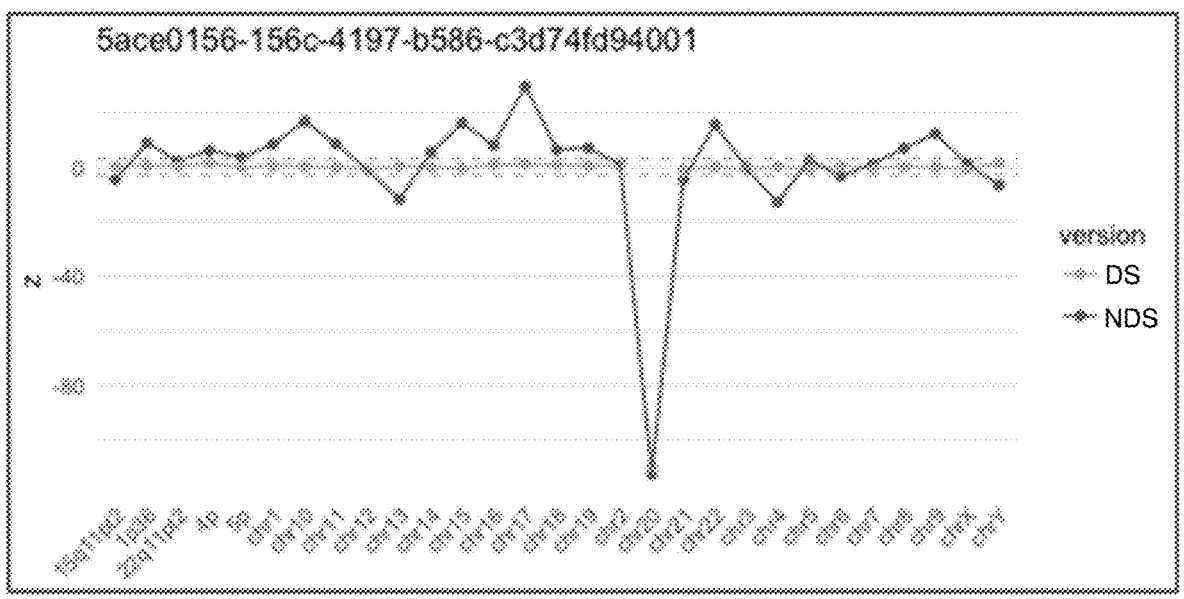
FIG. 12D shows depth-scaled Z-scores and non-depth-scaled Z-scores determined for chromosomes of an individual test maternal sample.

FIGS. 11A and 11B show comparisons of interquartile ranges of fold change values determined for each of a plurality of non-depth-scaled Z-scores and depth-scaled Z-scores respectively determined for a plurality of test maternal samples. The "false" regions correspond to samples not sequenced at a high read depth and the "true" regions correspond to samples sequenced at high read depths. As shown in FIGS. 11A and 11B, the interquartile ranges of fold change values for the depth-scaled Z-scores for the test maternal samples sequenced at low read depths showed less variation than the interquartile ranges of fold change values for the corresponding non-depth-scaled Z-scores.

Example 5: Z-Score Comparison Over Multiple Chromosomes

Z-scores for several test maternal samples were determined based on sequencing reads obtained from assays of the test maternal samples taken from pregnant women as described in Example 1. For comparison, depth-scaled Z-scores and non-depth-scaled Z-scores were determined for multiple chromosomes of each of the samples in the manner described in Example 1. As illustrated in FIGS. 12A-12D, the depth-scaled Z-scores (DS) showed significantly less variability than the non-depth-scaled Z-scores (NDS) for the test chromosomes of each of the test maternal samples.

The dashed lines in FIGS. 12A-12D indicate Z-scores of –3 and 3, which are exemplary predetermined upper and lower thresholds for calling aneuploidy. Depth-scaled Z-scores for several chromosomes of the test maternal samples exceeded the aneuploidy thresholds, demonstrating the capability of the depth-scaled Z-scores in aneuploidy calling. Non-depth-scaled Z-scores for a number of other chromosomes of the samples exceeded the aneuploidy call threshold, whereas the depth-scaled Z-scores for these chromosomes did not exceed the aneuploidy call threshold, indicating robustness of the depth-scaled Z-score determination against outliers and a significant reduction in false-positive calls for the test maternal samples using the depth-scaled Z-scores.

Figure 13A:
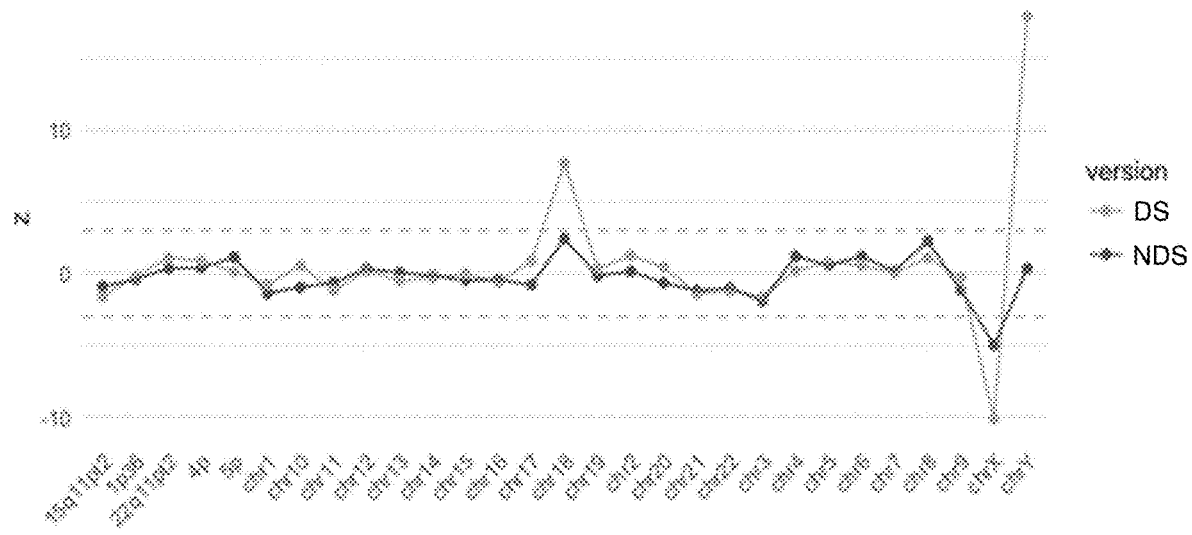
FIG. 13A shows depth-scaled Z-scores and non-depth-scaled Z-scores determined for chromosomes of an individual test maternal sample.
Figure 13B:
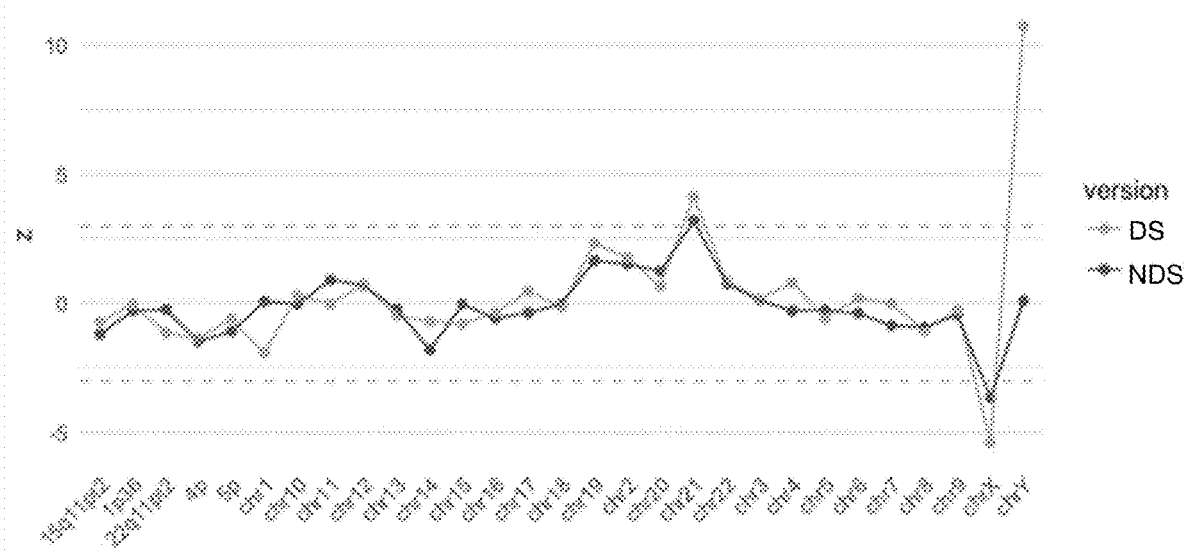
FIG. 13B shows depth-scaled Z-scores and non-depth-scaled Z-scores determined for chromosomes of an individual test maternal sample.
Figure 13C:
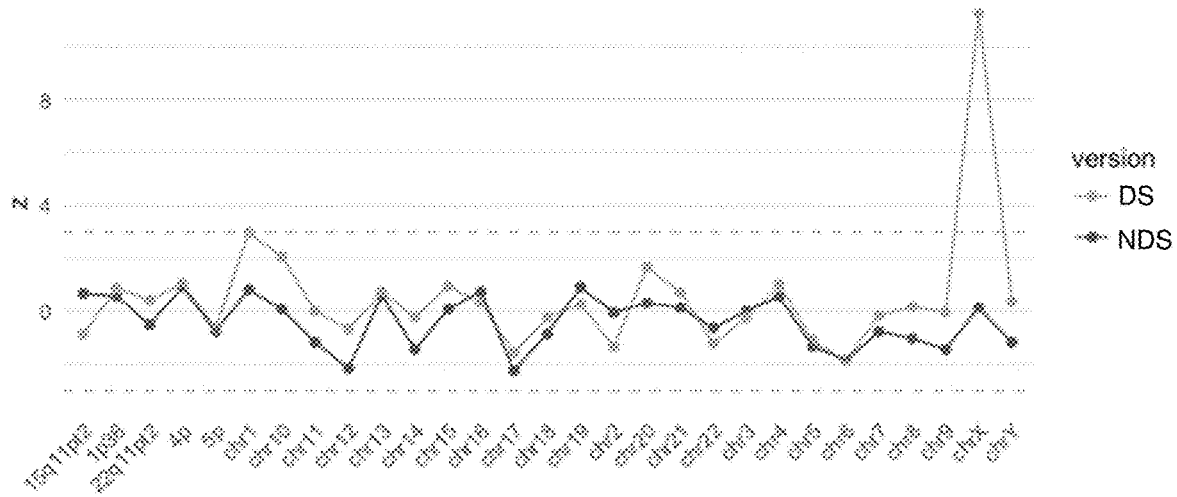
FIG. 13C shows depth-scaled Z-scores and non-depth-scaled Z-scores determined for chromosomes of an individual test maternal sample.
Figure 13D:
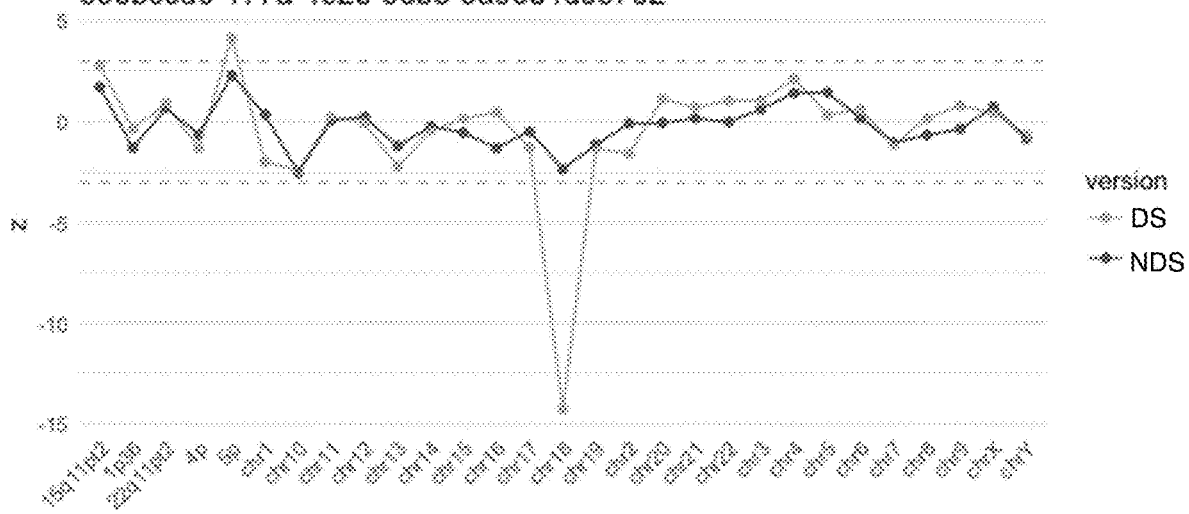
FIG. 13D shows depth-scaled Z-scores and non-depth-scaled Z-scores determined for chromosomes of an individual test maternal sample.

FIGS. 13A-13D show examples of test maternal samples for which determined non-depth-scaled Z-scores would result in false-negative aneuploidy calls. The dashed lines in FIGS. 13A-13D indicate Z-scores of –3 and 3, which are exemplary predetermined upper and lower thresholds for calling aneuploidy. With respect to the test maternal sample shown in FIG. 13A, a false-negative determination would be made for chromosome 18 based on the calculated non-depth-scaled Z-score being below the upper Z-score threshold. In contrast, the depth-scaled Z-score exceeds the upper Z-score threshold for chromosome 18 of the sample shown in FIG. 13A, demonstrating the improved capability of the depth-scaled Z-score calculation for identifying aneuploidies. Likewise, as shown in FIG. 13B, the depth-scaled Z-score exceeds the upper Z-score threshold for chromosome 21, while the non-depth-scaled Z-score is below the upper Z-score threshold. As shown in FIG. 13C, the depth-scaled Z-score exceeds the upper Z-score threshold for chromosome X, while the non-depth-scaled Z-score is below the upper Z-score threshold. As shown in FIG. 13D, the depth-scaled Z-score exceeds the lower Z-score threshold for chromosome 18, while the non-depth-scaled Z-score is above the lower Z-score threshold. Accordingly, the depth-scaled Z-score determination further demonstrates a reduction in false-negative calls for the test maternal samples.

Figure 14:
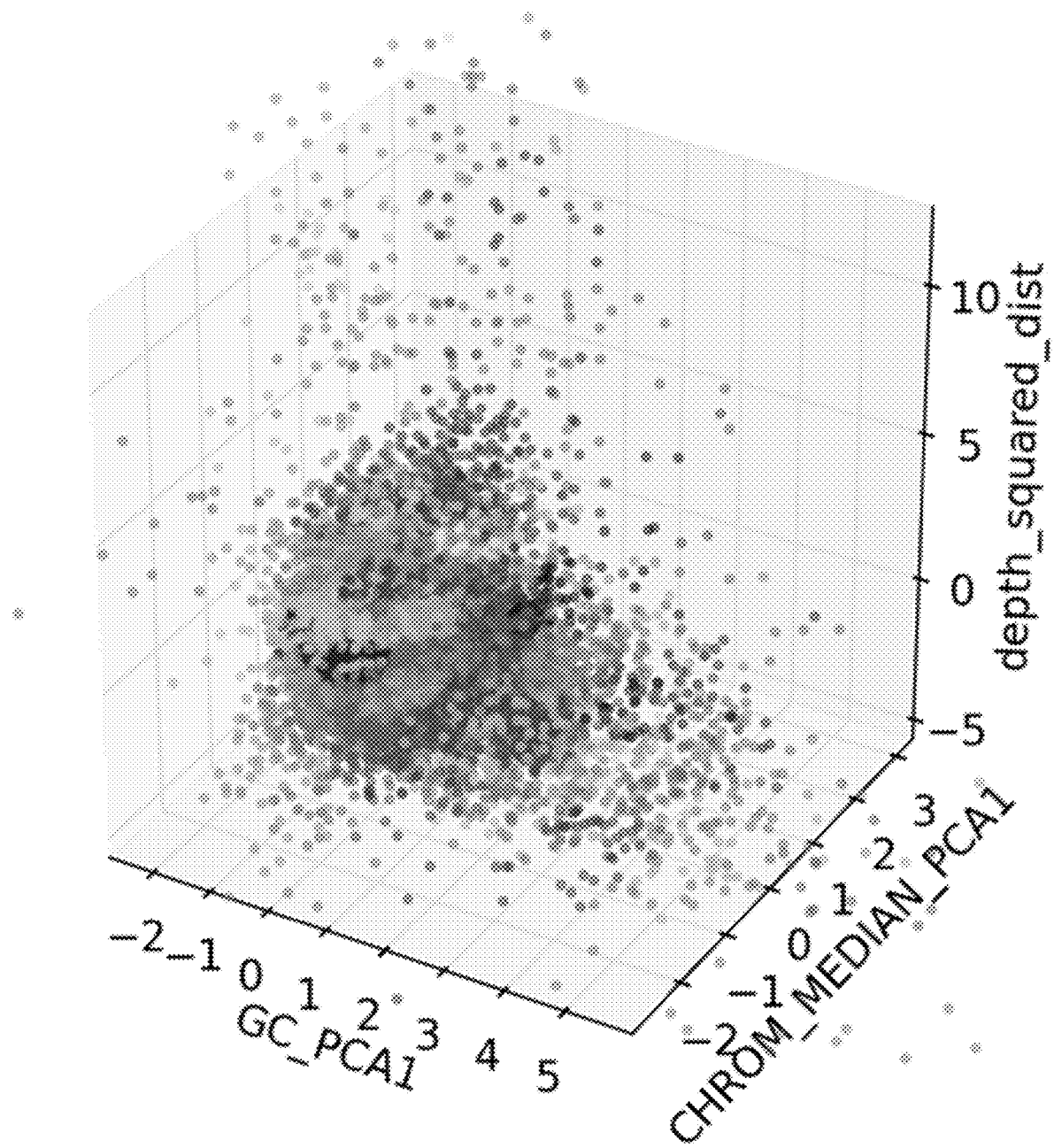
FIG. 14 shows maternal samples plotted according to various clustering Z-scores determined for the maternal samples.

Example 6: Sample Clustering 200 k-means clusters were generated for a population of sequenced maternal samples. The k-means clusters were generated based on Z-scores of metrics for GC bias, normalized chromosome median, and sequencing read depth for each of the maternal samples. The GC bias Z-score for each maternal sample was determined from a first principal component analysis (PCA) component on a GC-bias vector for the maternal sample. The normalized chromosome median Z-score for each maternal sample was determined from a PCA component on a vector of autosomal median linear bin counts for the maternal sample. The sequencing read depth Z-score for each maternal sample was determined based on a squared distance of the measured read depth for the maternal sample from a read depth of 17 million reads. FIG. 14 shows the maternal samples plotted according to the clustering Z-scores.

Figure 15A:
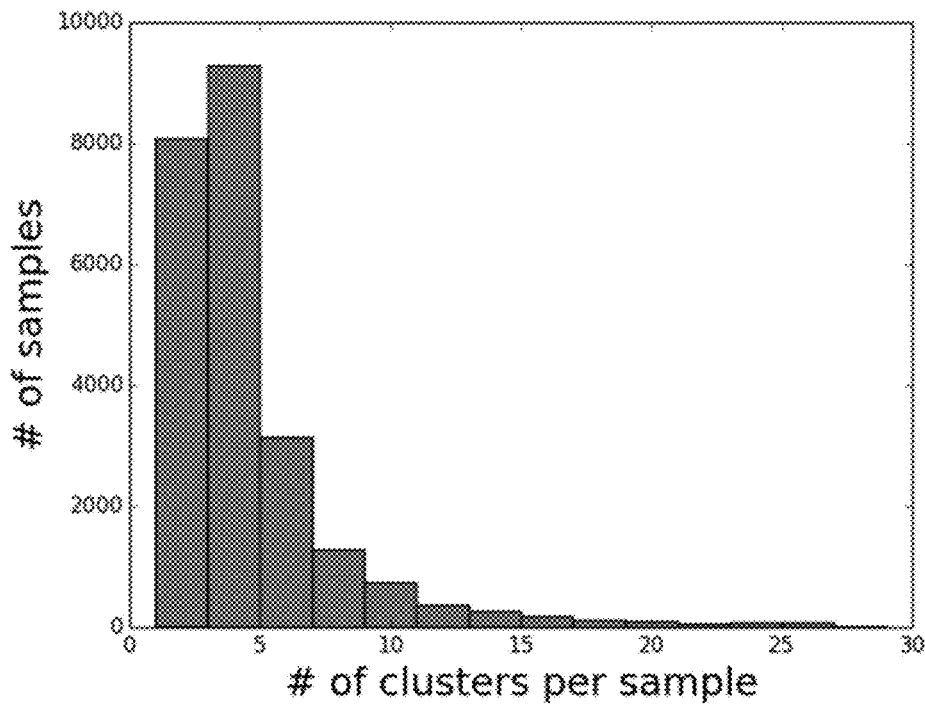
FIG. 15A illustrates a histogram showing relationships between clusters and test maternal samples utilized with the clusters during analyses of test maternal samples.

Each cluster was analyzed by identifying, out of the total population of sequenced maternal samples, 500 maternal samples that were closest to the centroid of the cluster, and assigning the 500 maternal samples to the cluster. This resulted in many samples being assigned to more than one cluster. FIG. 15A shows a histogram of ranges of numbers of clusters per sample (i.e., number of cluster each sample was assigned to) and corresponding numbers of samples for each of the ranges. The k-means clustering resulted in 75% of the maternal samples being assigned to more than one cluster. In contrast, maternal samples clustered through hierarchical clustering resulted in approximately 33% of the maternal samples being assigned to more than one cluster, and maternal samples clustered using a calibration table resulted in only 1.5% of the maternal samples being assigned to more than one cluster.

Figure 15B:
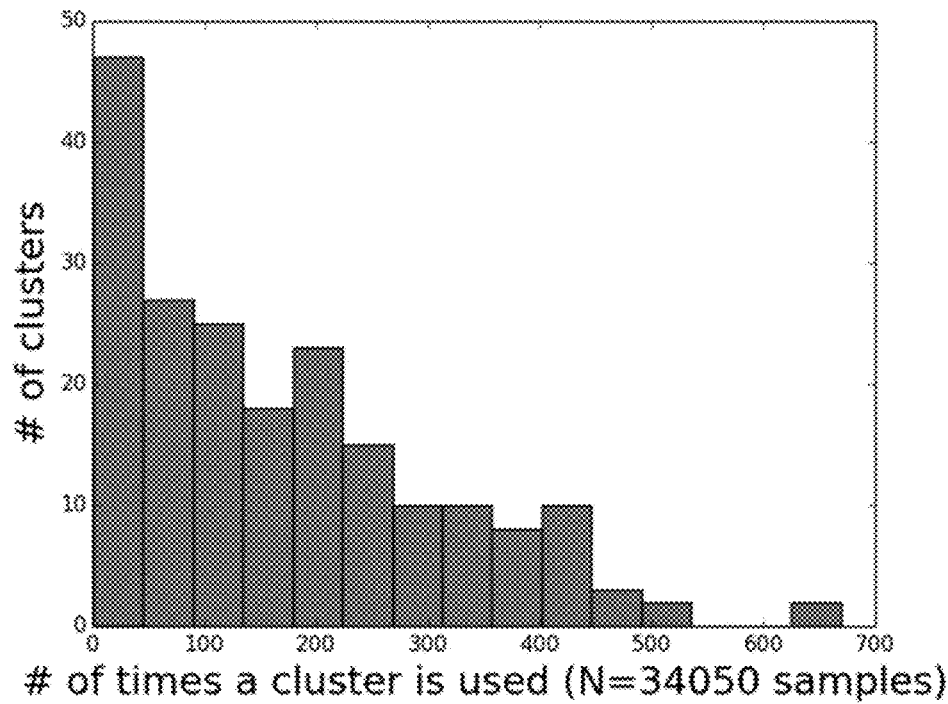
FIG. 15B illustrates a histogram showing relationships between clusters and the numbers of times the clusters were used during analyses of test maternal samples.

FIG. 15B shows a histogram of ranges of numbers of times clusters were used in analyzing test maternal samples (out of a population of 34,050 analyzed test maternal samples) and corresponding numbers of clusters for each of the ranges. The 200 k-means clusters were each used in the analyses of the test maternal samples. The k-means clusters were utilized a median of 136 times per cluster in the analyses of the 34,050 test maternal samples, with a maximum cluster use of 669 times for a cluster.

Figure 16:
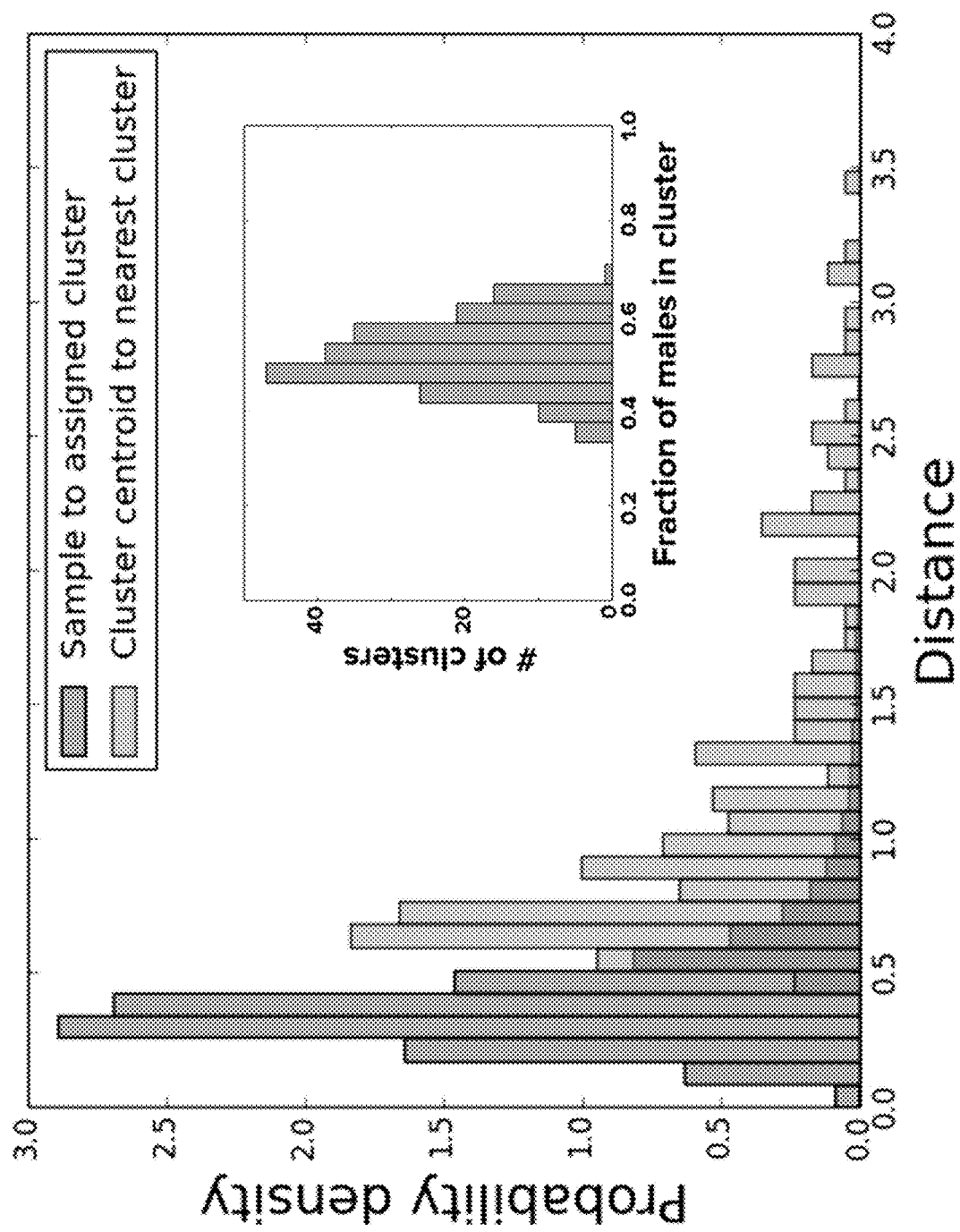
FIG. 16 illustrates a histogram of probability densities of distances between samples and cluster centroids of clusters to which they are assigned and distances between nearest cluster centroids.

FIG. 16 shows a histogram of probability densities of distances between samples and cluster centroids of clusters to which they are assigned and distances between nearest cluster centroids. As shown in FIG. 16, for the population of test maternal samples, the distance between a sample and its nearest centroid was generally less than the distance between centroids of the clusters themselves, suggesting that the cluster centroids were well distributed across the 3D population. Further, clusters had similar representation of males and females, indicating that allosome differences were not a dominant feature or artifact during clustering.

Example 7: ROC Comparison

Figure 17:
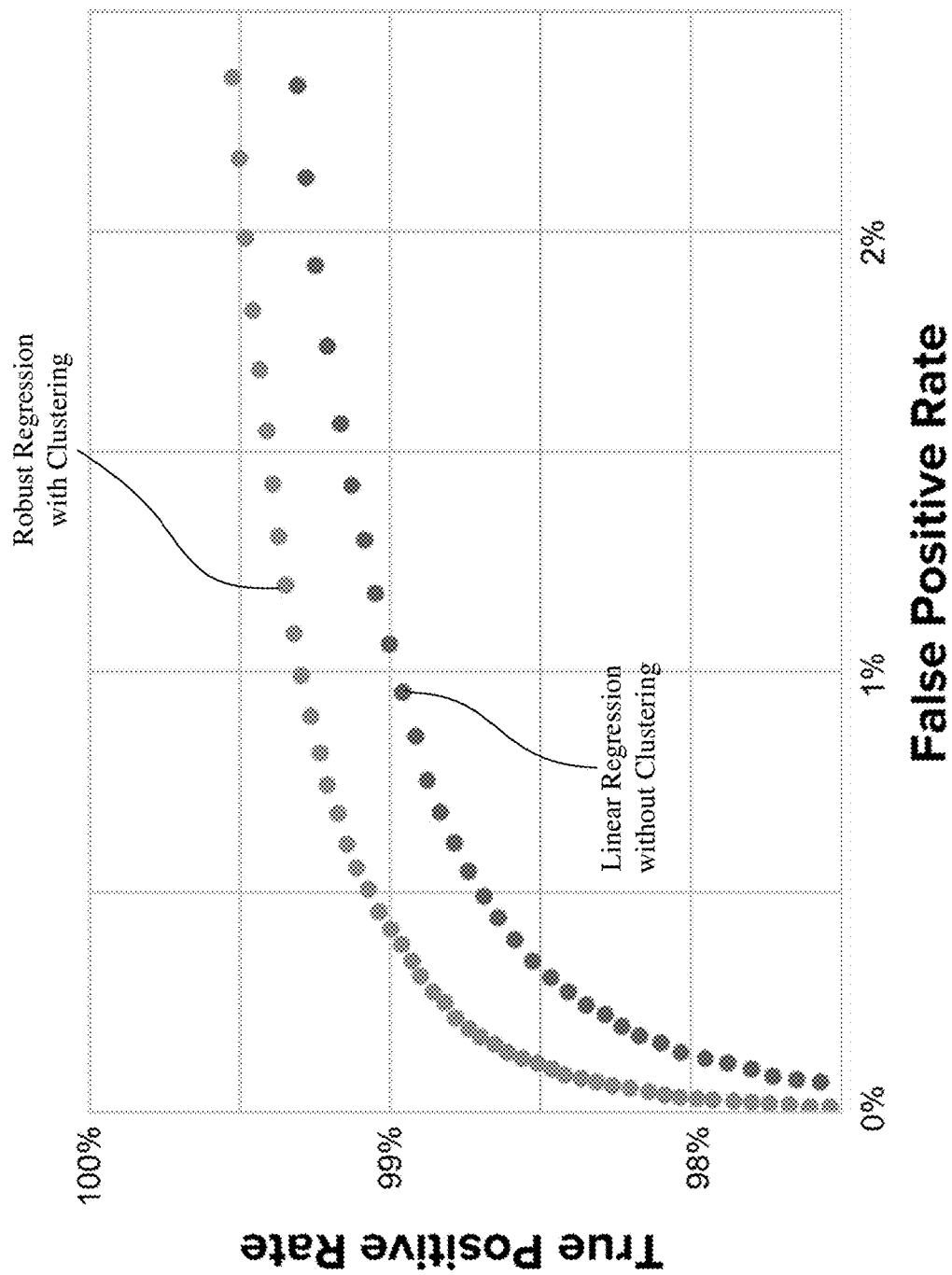
FIG. 17 illustrates receiver operating characteristic curves generated for classifications of fetal aneuploidy in chromosome 21 using different noninvasive prenatal testing methodologies.

FIG. 17 shows receiver operating characteristic (ROC) curves generated for classifications of fetal aneuploidy (i.e., trisomy 21) in chromosome 21 using different noninvasive prenatal testing methodologies. Using a Markov Chain Monte Carlo (MCMC)-based analysis of a Bayesian graphical model of fetal aneuploidies and noninvasive prenatal testing as described herein, posterior Z-score distributions of negative and positive samples were deduced. Scanning different Z-score threshold values for emitting positive or negative calls produced true- and false-positive rates, yielding the ROC curves shown in FIG. 17. The sensitivity (i.e., true-positive rate) was plotted versus 1−specificity (i.e., false-positive rate). As shown in FIG. 17, the ROC curves demonstrate that the noninvasive prenatal testing using clustering and robust regression performed significantly better than the noninvasive prenatal testing performed without the use of clustering and robust regression, resulting in increased sensitivity and specificity at each Z-score threshold value corresponding to a substantial reduction in the expected false-negative rate for chromosome 21. A substantial increased sensitivity and specificity at each Z-score threshold value corresponding to a substantial reduction in the expected false-negative rate for chromosomes 13 and 18 was also observed.

What is claimed is:

1. A method for non-invasively determining a chromosomal abnormality in a test chromosome of a fetus by analyzing a test maternal sample of a woman carrying said fetus, wherein the test maternal sample comprises fetal cell-free deoxyribonucleic acid (DNA) and maternal cell-free DNA, the method comprising:

training, by a computing system, a robust regression model using a set of measured dosages of a plurality of chromosomes or portions thereof of a plurality of reference maternal samples, the robust regression model trained to generate a respective expected dosage distribution of a respective chromosome of an input sample;

obtaining, by the computing system, an initial number of sequencing reads from the test maternal sample, wherein the initial number corresponds to an initial depth assay, and the initial number is at least 6 million;

aligning, by the computing system, the sequencing reads from an interrogated region of the test maternal sample;

binning, by the computing system, the aligned sequencing reads from the interrogated region of the test maternal sample in a plurality of bins such that each of the plurality of bins is at least 1 kilobase in length;

determining, by the computing system, a number of sequencing reads for each of the plurality of bins;

measuring, by the computing system, a dosage of the test chromosome or the portion thereof in the test maternal sample based on the number of sequencing reads in a set of bins corresponding to the test chromosome or the portion thereof;

determining, by the computing system, a depth-scaled variation value correlated to the initial number of sequencing reads obtained from the test maternal sample based at least on a plurality of reference samples assayed at a sequencing depth or a range of sequencing depths corresponding to the initial number of sequencing reads;

determining, by the computing system, an additional depth-scaled variation value correlated to a higher number of sequencing reads that is higher than the initial number of sequencing reads obtained from the test maternal sample based at least on a plurality of reference samples assayed at a higher sequencing depth or a range of sequencing depths corresponding to the higher number of sequencing reads;

executing, by the computing system, the robust regression model using the test chromosome or the portion thereof to generate an expected dosage of the test chromosome or the portion thereof;

determining, by the computing system, an initial value of statistical significance for the test chromosome or the portion thereof in the test maternal sample based on the measured dosage of the test chromosome or the portion thereof, the expected dosage of the test chromosome or the portion thereof, and the depth-scaled variation value;

determining, by the computing system, a predicted value of statistical significance for the test chromosome or the portion thereof in the test maternal sample based at least on the additional depth-scaled variation value correlated to the higher number of sequencing reads that is higher than the initial number of sequencing reads obtained from the test maternal sample;

determining that the absolute value of the initial value of statistical significance is below a predetermined threshold;

performing, in response to determining that the absolute value of the initial value of statistical significance is below the predetermined threshold, a higher depth assay to re-measure the dosage of the test chromosome or the portion thereof in the test maternal sample;

determining a subsequent value of statistical significance for the test chromosome or the portion thereof in the test maternal sample based on the re-measured dosage;

generating, by the computing system, based at least in part on the subsequent value of statistical significance, an indication of whether the test chromosome or the portion thereof in the fetal cell-free DNA of the test maternal sample is abnormal or normal; and providing, by the computing system, a report comprising the indication of whether the test chromosome or the portion thereof is abnormal or normal to inform a decision whether to pursue invasive screening.

2. The method of claim 1, wherein generating the indication comprises determining that the absolute value of the subsequent value of statistical significance is above a second predetermined threshold, and calling the test chromosome or the portion thereof in the fetal cell-free DNA of the test maternal sample to be abnormal in response to determining that the absolute value of the initial value of statistical significance is above the second predetermined threshold.

3. The method of claim 1, wherein the chromosomal abnormality is a microdeletion, and the test chromosome or the portion thereof is a putative microdeletion.

4. The method of claim 1, wherein the chromosomal abnormality is aneuploidy, and the test chromosome or the portion thereof is at least one complete chromosome.

5. The method of claim 1, wherein the dosage of the test chromosome or the portion thereof in the test maternal sample is measured by determining an average number of sequencing reads per bin and a variation of the number of sequencing reads per bin.

6. The method of claim 1, further comprising selecting a plurality of cohort reference maternal samples based on at least one similarity between each of the plurality of cohort reference maternal samples and the test maternal sample.

7. The method of claim 6, wherein the at least one similarity between each of the plurality of cohort reference maternal samples and the test maternal sample comprises at least one of a similarity in guanine-cytosine (GC) biases, binned sequencing depths, and bin count medians between the set of reference maternal samples and the test maternal sample.

8. The method of claim 6, wherein the at least one similarity between each of the plurality of cohort reference maternal samples and the test maternal sample is determined by determining one or more clusters that each include the test maternal sample and at least one of the plurality of cohort reference maternal samples.

9. The method of claim 6, wherein the at least one similarity between each of the plurality of cohort reference maternal samples and the test maternal sample is determined by:

identifying one or more clusters based on at least one characteristic value of the each of each the plurality of cohort reference maternal samples;

determining a centroid of each of the one or more clusters; and determining that the at least one characteristic value of the test maternal sample is within a threshold distance of the centroid of each of the one or more clusters.

10. The method of claim 6, wherein the initial value of statistical significance for the test chromosome or the portion thereof is determined by calculating an expected variation value that is based on:

the depth-scaled variation value; and a cohort-based variation value that is determined based on variation in counts of binned sequencing reads for the test chromosome or the portion thereof of the plurality of cohort reference maternal samples.

11. The method of claim 1, wherein the interrogated region comprises at least a portion of a chromosome other than the test chromosome or the portion thereof.

12. The method of claim 1, wherein the robust regression model is trained at least by:

for each of the plurality of reference maternal samples:
aligning sequencing reads from the interrogated region in the plurality of chromosomes or portions thereof,
binning the aligned sequencing reads from the interrogated region in a plurality of reference bins; and
counting the number of sequencing reads in each bin of the plurality of reference bins; and determining one or more model coefficients based on the number of sequencing reads in each bin for each of the plurality of reference maternal samples.

13. The method of claim 12, wherein the robust regression model utilizes a weight function that varies based on at least one of an average number of sequencing reads per bin and a variation of the number of sequencing reads per bin for the plurality of bins.

14. The method of claim 12, further comprising normalizing the number of sequencing reads in each bin prior to counting the number of sequencing reads in each bin.

15. The method of claim 1, wherein obtaining the initial number of sequencing reads comprises performing, by the computing system, using a sequencing device, an assay on the test maternal sample.

* * * * *